(12) United States Patent
Alfonta et al.

(10) Patent No.: US 11,365,399 B2
(45) Date of Patent: Jun. 21, 2022

(54) RECOMBINANT FLAVIN-ADENINE DINUCLEOTIDE GLUCOSE DEHYDROGENASE AND USES THEREOF

(71) Applicant: B. G. NEGEV TECHNOLOGIES AND APPLICATIONS LTD., AT BEN-GURION UNIVERSITY, Beer Sheva (IL)

(72) Inventors: Lital Alfonta, Omer (IL); Raz Zarivach, Beer Sheva (IL); Jennifer Grushka, Tel Aviv (IL); Itay Algov, Kadima (IL)

(73) Assignee: B. G. NEGEV TECHNOLOGIES AND APPLICATIONS LTD., AT GEN-GURION UNIVERSITY, Beer Sheva (IL)

( * ) Notice: Subject to any disclaimer, the term of this patent is extended or adjusted under 35 U.S.C. 154(b) by 6 days.

(21) Appl. No.: 16/636,013

(22) PCT Filed: Aug. 2, 2018

(86) PCT No.: PCT/IL2018/050863
§ 371 (c)(1),
(2) Date: Feb. 2, 2020

(87) PCT Pub. No.: WO2019/026082
PCT Pub. Date: Feb. 7, 2019

(65) Prior Publication Data
US 2020/0165579 A1 May 28, 2020

(30) Foreign Application Priority Data
Aug. 2, 2017 (IL) .......................................... 253801

(51) Int. Cl.
C12N 15/09 (2006.01)
C12N 9/04 (2006.01)
G01N 27/327 (2006.01)

(52) U.S. Cl.
CPC .......... *C12N 9/0006* (2013.01); *C12Y 101/05* (2013.01); *G01N 27/3271* (2013.01); *C07K 2319/61* (2013.01)

(58) Field of Classification Search
CPC ...... C12N 9/0006; C12N 15/09; C12Q 1/006; C12Y 101/9901
See application file for complete search history.

(56) References Cited

U.S. PATENT DOCUMENTS

| 8,354,112 | B2 | 1/2013 | Sode | |
| 8,716,442 | B2 * | 5/2014 | Takenaka | A61B 5/14532 530/350 |
| 2004/0023330 | A1 | 2/2004 | Sode | |
| 2017/0121751 | A1 * | 5/2017 | Kojima | C12Y 101/9901 |
| 2018/0355022 | A1 * | 12/2018 | Masakari | C07K 19/00 |

FOREIGN PATENT DOCUMENTS

| EP | 2589659 A1 | 5/2013 |
| WO | 2017013495 A2 | 1/2017 |
| WO | 2017094776 A1 | 6/2017 |

OTHER PUBLICATIONS

Inose et al. 2003; Cloning and expression of the gene encoding catalytic subunit of thermostable glucose dehydrogenase from Burkholderia cepacia in *Escherichia coli*. Biochimica et Biophysica Acta 1645: 133-138.*
Siponen et al. 2013; Structural insight into magnetochrome-mediated magnetite biomineralization. Nature. 502: 681-684 plus Methods and extended Data pp. 1-11.*
Algov et al. Sep. 15, 2017; Highly efficient flavin-adenine dinucleotide glucose dehydrogenase fused to a minimal cytochrome C domain. Journal of the American Chemical Society. 139: 17217-17220.*
Inyoung Lee et al, "The electrochemical behavior of a FAD dependent glucose dehydrogenase with direct electron transfer subunit by immobilization on self-assembled monolayers", Bioelectrochemistry, vol. 121, Jun. 2018, pp. 1-6.
H Yoshida et al, "Engineering a chimeric pyrroloquinoline quinone glucose dehydrogenase: improvement of EDTA tolerance, thermal stability and substrate specificity", Protein engineering, Jan. 1999, vol. 12 No. 1, pp. 63-70.
Yamaoka, H., Yamashita, Y., Ferri, S., & Sode, K. (2008), "Site directed mutagenesis studies of FAD-dependent glucose dehydrogenase catalytic subunit of Burkholderia cepacia" Biotechnology letters, 30(11), 1967-1972.
Simone, A. D. "Engineering the genetic code of *Escherichia coli* with methionine analogues and bioorthogonal amino acids for protein immobilization", 2016.
Joseph Wang, "Electrochemical Glucose Biosensors", Chem. Rev. 2008, 108, 2, 814-825.
L.Gorton et al, "Direct electron transfer between heme-containing enzymes and electrodes as basis for third generation biosensors", Analytica Chimica Acta, vol. 400, Issues 1-3, Nov. 22, 1999, pp. 91-108.
Wolfgang Harreither et al, "Recombinantly produced cellobiose dehydrogenase from Corynascus thermophilus for glucose biosensors and biofuel cells", Biotechnol J. Nov. 2012;7(11):1359-66.
Idan Gal et al, "Yeast surface display of dehydrogenases in microbial fuel-cells", Bioelectrochemistry. Dec. 2016; 112:53-60.

(Continued)

*Primary Examiner* — Karen Cochrane Carlson
(74) *Attorney, Agent, or Firm* — The Roy Gross Law Firm, LLC; Roy Gross

(57) ABSTRACT

A recombinant protein, including: (a) alpha subunit of an FAD-GDH; and (b) a minimal cytochrome c peptide is provided. Additionally, an electrode coupled to a recombinant protein, the recombinant protein made of: (a) a cofactor of a redox enzyme; (b) a redox enzyme; (c) a linker moiety configured to link any one of: the cofactor or the enzyme to an electron transfer (ET) domain; and (d) an ET domain, is also provided. Methods for: (a) transferring an electron to an electrode, by coupling the recombinant protein an electrode; and (b) quantifying the amount of an analyte e.g., glucose are also provided.

16 Claims, 11 Drawing Sheets
(2 of 11 Drawing Sheet(s) Filed in Color)
Specification includes a Sequence Listing.

(56) References Cited

OTHER PUBLICATIONS

B M Hallberg et al, "A new scaffold for binding haem in the cytochrome domain of the extracellular flavocytochrome cellobiose dehydrogenase", Structure. Jan. 15, 2000;8(1):79-88.

B M Hallberg et al, "Crystal structure of the flavoprotein domain of the extracellular flavocytochrome cellobiose dehydrogenase", J Mol Biol. Jan. 18, 2002;315(3):421-34.

G Gilardi et al, "Manipulating redox systems: application to nanotechnology", Trends Biotechnol. Nov. 2001; 19(11):468-76.

Junko Okuda et al, "PQQ glucose dehydrogenase with novel electron transfer ability", Biochem Biophys Res Commun Feb. 13, 2004;314(3):793-7.

Gianfranco Gilardi et al, "Molecular Lego: design of molecular assemblies of P450 enzymes for nanobiotechnology", Biosens Bioelectron. Jan. 2002;17(1-2):133-45.

Tomohiko Yamazaki et al, "Construction and Characterization of Direct Electron Transfer-Type Continuous Glucose Monitoring System Employing Thermostable Glucose Dehydrogenase Complex", Oct. 2008, Analytical Letters 41 (13):2363-2373.

I Willner I et al, "Integration of Layered Redox Proteins and Conductive Supports for Bioelectronic Applications", Angew Chem Int Ed Engl. Apr. 2000;39(7):1180-1218.

Hideaki Yamaoka et al, "SPCE Based Glucose Sensor Employing Novel Thermostable Glucose Dehydrogenase, FADGDH: Blood Glucose Measurement with 150nL Sample in One Second", J Diabetes Sci Technol. Jan. 2007; 1(1):28-35.

Yuki Yamashita et al, "Direct electron transfer type disposable sensor strip for glucose sensing employing an engineered FAD glucose dehydrogenase", Enzyme Microb Technol. Feb. 5, 2013;52(2):123-8.

Marina I Siponen et al, "Structural insight into magnetochrome-mediated magnetite biomineralization", Nature. Oct. 31, 2013;502(7473):681-4.

Itay Algov et al, "Highly Efficient Flavin-Adenine Dinucleotide Glucose Dehydrogenase Fused to a Minimal Cytochrome C Domain", J Am Chem Soc. Dec. 6, 2017;139(48):17217-17220.

PCT Search Report for International Application No. PCT/IL2018/050863; dated Oct. 28, 2018 ; 4 pp.

PCT Written Opinion for International Application No. PCT/IL2018/050863; dated Oct. 28, 2018 ; 6 pp.

PCT Preliminary Report for International Application No. PCT/IL2018/050863; dated Feb. 4, 2020 ; 7 pp.

* cited by examiner

RECOMBINANT FLAVIN-ADENINE DINUCLEOTIDE GLUCOSE DEHYDROGENASE AND USES THEREOF

CROSS-REFERENCE TO RELATED APPLICATIONS

This application is a National Phase of PCT Patent Application No. PCT/IL2018/050863 having International filing date of Aug. 2, 2018 titled "A RECOMBINANT FLAVIN-ADENINE DINUCLEOTIDE GLUCOSE DEHYDROGENASE AND USES THEREOF", which claims the benefit of priority from Israeli Patent Application No. 253801 filed on Aug. 2, 2017. The contents of the above applications are all incorporated by reference as if fully set forth herein in their entirety.

FIELD OF INVENTION

The present invention relates to recombinant proteins, methods of using the same such as for direct electron transfer in bio-electrochemical applications.

BACKGROUND OF THE INVENTION

Redox enzymes are proteins that participate in biocatalytic processes which involve electron transfer (ET). Depending on their redox potential, enzyme mediated redox reactions may be used in anodes and cathodes of biofuel cells as well as in biosensing applications. For the utilization of most redox enzymes in such devices, a mediator molecule should be used to mediate the ET between the enzyme and the electrode. The use of an external redox mediator results in a potential loss as well as in low power outputs.

Redox mediator molecules introduce two major challenges to the system: the first is having a middle point potential value that affords an efficient electron transfer from an enzyme to the electrode, which results in insufficient energy production. The other, is the need for diffusion of the mediator molecule through solution towards the electrode which might cause an additional loss of energy.

SUMMARY OF THE INVENTION

The present invention relates to a recombinant protein having superior FAD-GDH (flavin-adenine dinucleotide glucose dehydrogenase) activity and methods of using the same.

According to an aspect of some embodiments of the present invention there is provided a recombinant protein, comprising: (a) alpha subunit of an FAD-GDH; and (b) a minimal c-type cytochrome peptide.

In some embodiments, the minimal c-type cytochrome peptide comprises 11 to 30 amino acids.

In some embodiments, the alpha subunit of an FAD-GDH is a *Burkholderia cepacian* alpha subunit of an FAD-GDH.

In some embodiments, the alpha subunit of an FAD-GDH is derived from a thermostable enzyme, an oxygen independent enzyme, or both. In some embodiments, the minimal cytochrome peptide is a cytochrome domain MCR-2 from a MamP protein.

In some embodiments, the minimal cytochrome peptide is a magnetotactic bacterius minimal cytochrome peptide.

In some embodiments, the protein has a molecular weight in the range of 63 to 65 kDa.

In some embodiments, the recombinant protein is bound to a porphyrin comprising a metal.

In some embodiments, the recombinant protein is bound to a compound of formula I:

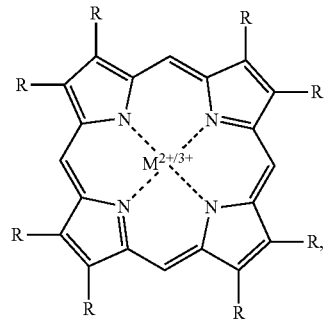

wherein the R is any electron donor, the compound of formula I is bound to a metal.

In some embodiments, the metal is a trivalent metal or a divalent metal.

In some embodiments, the recombinant protein has both peroxidase activity and oxidative activity.

In some embodiments, the recombinant protein comprises an amino acid sequence selected from the group consisting SED ID NOs: 8 to 13.

In some embodiments, there is provided a composition comprising the recombinant protein disclosed herein in an embodiment thereof, and the gamma subunit of an FAD-GDH.

In some embodiments, there is provided a composition comprising the recombinant protein disclosed herein in an embodiment thereof, and the gamma subunit of an FAD-GDH as two separate unbound proteins.

In some embodiments, there is provided a DNA molecule comprising a nucleotide sequence encoding the disclosed recombinant protein in an embodiment thereof with or without the gamma subunit of an FAD-GDH.

In some embodiments, the DNA molecule comprises the nucleic acid sequence selected from the group consisting SEQ ID NOs: 5-7 and 10.

In some embodiments, there is provided an expression vector comprising the DNA molecule disclosed herein in an embodiment thereof.

In some embodiments, there is provided a cell comprising the DNA molecule disclosed herein in an embodiment thereof, and the recombinant protein disclosed herein in an embodiment thereof, or both.

In some embodiments, the cell is a prokaryotic cell.

In some embodiments, there is provided the recombinant protein disclosed herein in an embodiment thereof, coupled to an electrode. In some embodiments, the coupled is covalently bound.

In some embodiments, the recombinant protein is coupled to an electrode via a mediator molecule comprising non-canonical amino acid (ncAA) residue.

According to another aspect, there is provided an electrode coupled to a recombinant protein, the recombinant protein comprising:

(a) a cofactor of a redox enzyme; (b) a redox enzyme; (c) a linker moiety configured to link any one of: the cofactor or the enzyme to an electron transfer (ET) domain; and (d) an ET domain, configured to transfer electrons between the electrode and the cofactor; wherein a distance between the ET domain and the electrode is in the range of 0 to 14 Å.

In some embodiments, the recombinant protein is in the form of formula: (a)-(b)-(c)-(d).

In some embodiments, the cofactor is selected from the group consisting of: FAD, NAD$^+$, and NADP$^+$.

In some embodiments, the redox enzyme is selected from an oxidase, a dehydrogenase, and a malic enzyme.

In some embodiments, the redox enzyme has a redox potential of less than 50 mV vs. Ag/AgCl.

In some embodiments, the ET domain comprises a minimal c-type cytochrome peptide.

In some embodiments, the electrode comprises a material selected from gold, graphite, and glassy carbon electrode (GCE).

In some embodiments, the ET is attached to the electrode.

In some embodiments, the ET is covalently attached to the electrode to the electrode via a mediator molecule. In some embodiments, the mediator molecule comprises one or more non-canonical amino acids.

In some embodiments, the one or more non-canonical amino acids comprise Propargyl-lysine (PrK).

In some embodiments, the mediator molecule comprises polycyclic aromatic system.

In some embodiments, there is provided a device comprising the electrode.

In some embodiments, the device is for biosensing glucose in a medium.

According to another aspect, there is provided a method for transferring an electron to an electrode, comprising coupling the disclosed recombinant protein in an embodiment thereof to an electrode, thereby transferring an electron to the electrode.

In some embodiments, the coupling is in the absence of a mediator molecule.

According to another aspect, there is provided a method for quantifying the amount of a reporter in a sample having a first detectable range of light absorbance in an oxidized state a second range of light absorbance in a non-oxidized state, comprising:
(a) contacting the disclosed recombinant protein in an embodiment thereof with the reporter in a non-oxidized state; and
(b) measuring the amount of the reporter in an oxidized state, thereby quantifying the amount of a reporter in a sample.

In some embodiments, the first detectable range of light absorbance is detectable in visible light and the second range of light absorbance is non-detectable in visible light.

In some embodiments, the reporter is 2,6-Dichloroindophenol.

In some embodiments, the 2,6-Dichloroindophenol is coupled to glucose.

In another aspect, there is provided a method for determining an analyte in a liquid medium, the analyte being capable to undergo a biocatalytic oxidation or reduction reaction in the presence of an oxidizer or a reducer, respectively, the method comprising:
(i) providing the disclosed device in an embodiment thereof;
(ii) contacting the device with the liquid medium;
(iii) measuring the electric signal generated between the cathode and the anode, the electric signal being indicative of the presence and/or the concentration of the analyte; and
(iv) determining the analyte based on the electric signal.

In some embodiments, the analyte comprises glucose.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

DETAILED DESCRIPTION OF THE INVENTION

Figure 1:
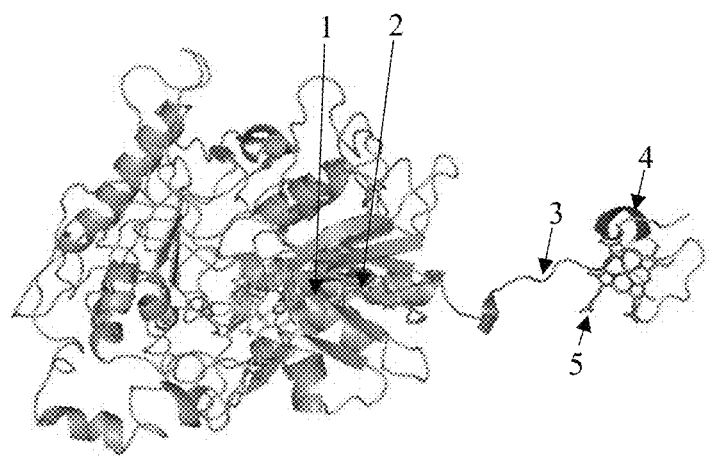
FIG. 1 is a 3D model of Flavin-adenine dinucleotide dependent glucose dehydrogenase FAD-GDH-MCD (FGM) based on the structure of GDH, predicted by homology to formate oxidase using Swiss-model (3q9t) and on the structure of MCD from MamP crystal structure (4jj0). FAD-GDH from *Burkholderia cepacia* is presented with its FAD binding motif (orange, "1") and the FAD co-factor MCD model (light orange, "2") and the linker (grey, "3") were cut from mamP known 3D structure and include the Heme binding motif (red, "4") and heme molecule (pink, "5"). Heme and FAD molecules were attached to the protein model manually using PyMOL.

Provided herein is a recombinant flavin-adenine dinucleotide glucose dehydrogenase (FAD-GDH) enzyme, polynucleotides sequences encoding same, useful for direct electron transfer such as in bio-electrochemical applications, including, but not limited to, glucose monitoring.

As provided in some embodiments of the present invention, fusing the enzyme with a minimal cytochrome domain (MCD), instead of large cytochrome, allows to shorten the enzyme-electrode distance and improve the direct electron transfer (DET) capabilities of the enzyme. As demonstrated hereinbelow under a non-limiting example, the fusion enzyme communicated with an electrode directly, without the use of a mediator molecule. Direct electron transfer between the redox enzyme and an electrode resulted in enhancement of chemical detection.

As demonstrated hereinbelow, the disclosed recombinant enzyme showed a substantially reduced redox potential, e.g., from +400 mV to 0 mV, thereby improving enzyme selectivity in various electrochemical applications including glucose sensing and monitoring as well as an electromotive force in a bio-electrochemical power device.

Before explaining further embodiments of the invention in detail, it is to be understood that the invention is not necessarily limited in its application to the details set forth in the following description or exemplified by the Examples. The invention is capable of other embodiments or of being practiced or carried out in various ways.

The present invention provides, in some embodiments, a recombinant protein comprising: (a) an alpha subunit of an FAD-GDH; and (b) a minimal cytochrome peptide.

In one embodiment, the alpha subunit of the FAD-GDH is derived or recovered from a prokaryotic cell. In one embodiment, the alpha subunit of the FAD-GDH is derived or recovered from a bacterial cell. In one embodiment, the alpha subunit of the FAD-GDH is $Burkholderia$ $cepacian$ alpha subunit of FAD-GDH. In one embodiment, the alpha subunit of the FAD-GDH of the present invention is derived from a thermostable enzyme, an oxygen independent enzyme, or both.

The term "thermostable enzyme" refers to an enzyme that is relatively stable to heat. The thermostable enzymes can withstand the high temperature incubation used to remove the modifier groups, typically, but not exclusively, greater than 50° C., without suffering an irreversible loss of activity.

In one embodiment, the recombinant protein further comprises the gamma subunit of an FAD-GDH. In one embodiment, the invention provides a composition comprising or consisting the recombinant protein with or without the gamma subunit of an FAD-GDH. In one embodiment, the invention provides a composition comprising or consisting the recombinant protein and the gamma subunit of an FAD-GDH. In one embodiment, the invention provides a composition comprising or consisting at least two different proteins: (a) the recombinant protein; and (b) the gamma subunit of an FAD-GDH. In one embodiment, the at least two different proteins are unbound. In some embodiments, the gamma subunit is from the same FAD-GDH as the alpha subunit. In some embodiments, the gamma subunit is from a different FAD-GDH as the alpha subunit. In some embodiments, the gamma subunit is from the same or different FAD-GDH as the alpha subunit.

In one embodiment, the recombinant protein further comprises a minimal cytochrome peptide. In one embodiment, the minimal cytochrome peptide is a natural peptide. In one embodiment, the minimal cytochrome peptide comprises a non-natural peptide.

In one embodiment, the recombinant protein is devoid of the gamma subunit of the FAD-GDH. In one embodiment, the minimal cytochrome peptide comprises a c-type cytochrome domain. In one embodiment, the minimal cytochrome peptide does not comprise a b-type cytochrome domain. In one embodiment, the minimal cytochrome peptide comprises a c-type cytochrome domain MCR-2 from a MamP protein. In one embodiment, the minimal cytochrome peptide comprises a magnetotactic bacterium minimal cytochrome peptide. In one embodiment, the minimal cytochrome peptide is a magnetotactic bacterius minimal cytochrome peptide.

In one embodiment, the minimal cytochrome peptide is a peptide comprising or consisting of 11 to 30 amino acids. In one embodiment, the minimal cytochrome peptide is a peptide comprising or consisting of 11 to 24 amino acids. In some embodiments, the minimal domain is a naturally occurring cytochrome. In some embodiments, the minimal domain is a synthetic cytochrome.

In one embodiment, the minimal cytochrome peptide is a cytochrome peptide (e.g., c-type cytochrome) comprising or consisting of 11, 12, 13, 14, 15, 16, 17, 18, 19, 20, 21, 22, 23, 24, 25, 26, 27, 28, 29, or 30 amino acids, including any range therebetween. In some embodiments, the peptide comprises cytochrome functionality. In some embodiments, the peptide comprises ET functionality.

In one embodiment, the minimal cytochrome peptide is linked to the amino terminus of the alpha subunit of an FAD-GDH. In one embodiment, the minimal cytochrome peptide is linked to the carboxy terminus of the alpha subunit of an FAD-GDH. In one embodiment, the minimal cytochrome peptide is linked to the amino terminus of the gamma subunit of an FAD-GDH. In one embodiment, the minimal cytochrome peptide is linked to the carboxy terminus of the gamma subunit of an FAD-GDH.

In one embodiment, the minimal cytochrome peptide is linked to the subunit of an FAD-GDH directly or indirectly. In one embodiment, the minimal cytochrome peptide is linked to the carboxy terminus of the subunit of an FAD-GDH directly or indirectly.

In one embodiment, the recombinant protein, further comprises a linker. In one embodiment, the recombinant protein, further comprises a peptide linker. In one embodiment, the minimal cytochrome peptide is linked to the carboxy terminus or the amino terminus of the alpha subunit of an FAD-GDH via a peptide linker. In one embodiment, the minimal cytochrome peptide is linked to the carboxy terminus or the amino terminus of the gamma subunit of an FAD-GDH via a peptide linker.

In one embodiment, the minimal cytochrome peptide is linked to the amino or carboxy terminus of the subunit via a linker comprising or consisting 5 to 20 amino acids. In one embodiment, the minimal cytochrome peptide is linked to the amino or carboxy terminus of the subunit via a linker comprising or consisting 8 to 18 amino acids. In one embodiment, the minimal cytochrome peptide is linked to the amino or carboxy terminus of the subunit via a linker comprising or consisting 12 to 15 amino acids. In one embodiment, the minimal cytochrome peptide is linked to the amino or carboxy terminus of the subunit via a linker comprising or consisting 5 to 15 amino acids. In some embodiments, the linker is between 1 and 10, 1 and 9, 1 and 8, 1 and 7, 2 and 10, 2 and 9, 2 and 8, 2 and 7, 3 and 10, 3 and 9, 2 and 8 or 2 and 7 amino acids in length.

In some embodiments, the linker comprises 30% to 60% glycine. In some embodiments, the linker comprises 30% to 60% serine. In some embodiments, the linker is hydrophilic. In some embodiments, the linker does not cause steric hinderance. In some embodiments, the linker is a flexible linker. In some embodiments, the linker does not interfere with maturation of the porphyrin binding MCD. In some embodiments, the linker does not interfere with enzymatic activity of the other subunits. In some embodiments, the linker is not so short that the other subunit interferes with maturation of the porphyrin binding MCD. In some embodiments, the linker retains the subunits in close enough proximity to allow electron transfer. In some embodiments, the linker has a length of up to 20 Å, up to 25 Å, or up to 30 Å. In some embodiments, the linker has a length of greater than or equal to 5 Å, 10 Å, 12 Å, 15 Å or 17 Å. Non-limiting exemplary linker is a peptide comprising GSGYGSG (SEQ ID NO: 27). In some embodiments, the linker comprises or consists of SEQ ID NO: 24. In some embodiments, the linker comprises or consists a non-peptide backbone.

In one embodiment, the linker is encoded by a DNA sequence comprising or consisting the nucleotide sequence: GAATTCGGTTCTGGTTATGGCTCTGGTCCGCCGG-GTCCG (SEQ ID NO: 4). It will be understood by a skilled artisan that synonymous substitutions may be made to this sequence.

In one embodiment, the linker is encoded by a DNA sequence comprising or consisting of a nucleotide sequence synonymous with SEQ ID NO: 4).

Without being bound by any particular mechanism it is assumed that a short linker containing glycine renders the linker with a desired flexibility. Further, and without being bound by any particular mechanism it is assumed that a short linker containing serine renders the linker with a desired hydrophilicity.

Further, a shorter linker (e.g. shorter than to 5 Å) could prevent proper maturation of the porphyrin binding MCD (due to its close proximity to GDH); on the other hand, a longer linker (e.g., longer than 30 Å) could prevent efficient ET between the two domains.

In one embodiment, the recombinant protein further comprises a short tag peptide (3 to 20 amino acids long). In one embodiment, the short tag peptide is his tag. In some embodiments, the tag is a 6× his tag. Protein tags are well known in the art and any tag that does not interfere with the function (redox and ET) of the recombinant protein may be used. In some embodiments, the short tag is between 1 and 30, 1 and 25, 1 and 20, 1 and 15, 1 and 10, 2 and 30, 2 and 25, 2 and 20, 2 and 25, 2 and 10, 3 and 30, 3 and 25, 3 and 20, 3 and 15 or 3 and 10 amino acids in length. Each possibility represents a separate embodiment of the invention.

In one embodiment, the recombinant protein has a molecular weight in the range of 58 to 75 kDa. In one embodiment, the recombinant protein has a molecular weight in the range of 60 to 70 kDa. In one embodiment, the recombinant protein has a molecular weight in the range of 63 to 65 kDa. In one embodiment, the recombinant protein has a molecular weight in the range of 62 to 68 kDa. In one embodiment, the recombinant protein has a molecular weight in the range of 63 to 65 kDa.

In some embodiments, the amino acid sequence of the recombinant protein comprises or consists of the following sequence:

```
MADTDTQKADVVVVGSGVAGAIVAHQLAMAGKSVILLEAGPRMPRWEIVE

RFRNQVDKTDFMAPYPSSAWAPHPEYGPPNDYLILKGEHKFNSQYIRAVG

GTTWHWAASAWRFIPNDFKMKTVYGVGRDWPIQYDDIEHYYQRAEEELGV

WGPGPEEDLYSPRKEPYPMPPLPLSFNEQTIKSALNGYDPKFHVVTEPVA

RNSRPYDGRPTCCGNNNCMPICPIGAMYNGIVHVEKAEQAGAKLIDSAVV

YKLETGPDKRITAAVYKDKTGADHRVEGKYFVIAANGIETPKILLMSANR

DFPNGVANSSDMVGRNLMDHPGTGVSFYANEKLWPGRGPQEMTSLIGFRD

GPFRANEAAKKIHLSNMSRINQETQKIFKGGKLMKPEELDAQIRDRSARF

VQFDCFHEILPQPENRIVPSKTATDAVGIPRPEITYAIDDYVKRGAVHTR

EVYATAAKVLGGTEVVFNDEFAPNNHITGATIMGADARDSVVDKDCRAFD

HPNLFISSSSTMPTVGTVNVTLTIAAL (SEQ ID NO: 8, shortened).
```

Hereinthroughout, in some embodiments, by "shortened" or "partial" it is meant to refer to without e.g., tag peptide, and/or a linker.

In some embodiments, the amino acid sequence of the recombinant protein comprises or consists of the following sequence:

MADTDTQKADVVVVGSGVAGAIVAHQLAMAGKSVILLEAGPRMPRWEIVE
RFRNQVDKTDFMAPYPSSAWAPHPEYGPPNDYLILKGEHKFNSQYIRAVG
GTTWHWAASAWRFIPNDFKMKTVYGVGRDWPIQYDDIEHYYQRAEEELGV
WGPGPEEDLYSPRKEPYPMPPLPLSFNEQTIKSALNGYDPKFHVVTEPVA
RNSRPYDGRPTCCGNNNCMPICPIGAMYNGIVHVEKAEQAGAKLIDSAVV
YKLETGPDKRITAAVYKDKTGADHRVEGKYFVIAANGIETPKILLMSANR
DFPNGVANSSDMVGRNLMDHPGTGVSFYANEKLWPGRGPQEMTSLIGFRD
GPFRANEAAKKIHLSNMSRINQETQKIFKGGKLMKPEELDAQIRDRSARF
VQFDCFHEILPQPENRIVPSKTATDAVGIPRPEITYAIDDYVKRGAVHTR
EVYATAAKVLGGTEVVFNDEFAPNNHITGATIMGADARDSVVDKDCRAFD
HPNLFISSSSTMPTVGTVNVTLTIAALALRMSDTLKKEVIRAGATMPHRD
RGPCGACHAIIQ (SEQ ID NO: 9, full).

In some embodiments, the amino acid sequence of the recombinant protein comprises or consists of the following sequence:

MADTDTQKADVVVVGSGVAGAIVAHQLAMAGKSVILLEAGPRMPRWEIVE
RFRNQVDKTDFMAPYPSSAWAPHPEYGPPNDYLILKGERKENSQYIRAVG
GTTWHWAASAWRFIPNDFKMKTVYGVGRDWPIQYDDIEHYYQRAEEELGV
WGPGPEEDLYSPRKEPYPMPPLPLSFNEQTIKSALNGYDPKFHVVTEPVA
RNSRPYDGRPTCCGNNNCMPICPIGAMYNGIVHVEKAEQAGAKLIDSAVV
YKLETGPDKRITAAVYKDKTGADHRVEGKYFVIAANGIETPKILLMSANR
DFPNGVANSSDMVGRNLMDHPGTGVSFYANEKLWPGRGPQEMTSLIGFRD
GPFRANEAAKKIHLSNMSRINQETQKIFKGGKLMKPEELDAQIRDRSARF
VQFDCFHEILPQPENRIVPSKTATDAVGIPRPEITYAIDDYVKRGAVHTR
EVYATAAKVLGGTEVVFNDEFAPNNHITGATIMGADARDSVVDKDCRAFD
HPNLFISSSSTMPTVGTVNVTLTIAALALRMSDTLKKEVEFGSGYGSGPP
GPIRAGATMPHRDRGPCGACHAIIQGSGSGHHHHHH (SEQ ID NO: 10, full).

In some embodiments, the amino acid sequence of the recombinant protein comprises or consists of the following sequence:

MADTDTQKADVVVVGSGVAGAIVAHQLAMAGKSVILLEAGPRMPRWEIVE
RFRNQVDKTDFMAPYPSSAWAPHPEYGPPNDYLILKGEHKFNSQYIRAVG
GTTWHWAASAWRFIPNDFKMKTVYGVGRDWPIQYDDIEHYYQRAEEELGV
WGPGPEEDLYSPRKEPYPMPPLPLSFNEQTIKSALNGYDPKFHVVTEPVA
RNSRPYDGRPTCCGNNNCMPICPIGAMYNGIVHVEKAEQAGAKLIDSAVV
YKLETGPDKRITAAVYKDKTGADHRVEGKYFVIAANGIETPKILLMSANR
DFPNGVANSSDMVGRNLMDHPGTGVSFYANEKLWPGRGPQEMTSLIGFRD
GPFRANEAAKKIHLSNMSRINQETQKIFKGGKLMKPEELDAQIRDRSARF
VQFDCFHEILPQPENRIVPSKTATDAVGIPRPEITYAIDDYVKRGAVHTR
EVYATAAKVLGGTEVVFNDEFAPNNHITGATIMGADARDSVVDKDCRAFD
HPNLFISSSSTMPTVGTVNVTLTIAALALRMSDTLKKEVEFGSGYGSGPP
GPIRAGATMPHRDRGPCGACHAIIQ (SEQ ID NO: 11, partial).

An Electrode

In some embodiments, there is provided an electrode carrying or coupled to a recombinant protein comprising A, B, C, and D, wherein:

A is a cofactor of a redox enzyme;
B is a redox enzyme;
C is a linker moiety; and
D is an electron transfer (ET) domain that is configured to transfer electrons between the electrode and A. In some embodiment the ET comprises a cytochrome.

In one embodiment, the A, B, C, and D are linked to each other under the following order: A-B-C-D.

In some embodiments, the cofactor, when not bound to a linker moiety, comprises at least one pair of hydroxyl groups.

In one embodiment, there is provided a device comprising the electrode.

In one embodiment, the electrode comprises a material selected from, without being limited thereto, graphite and glassy carbon electrode (GCE).

In one embodiment, the electrode is made of or coated by an electrically conducting substance, such as, without being limited thereto gold, platinum, silver, conducting glass such as indium tin oxide (ITO).

In one embodiment, by "chemically attach to" it is meant to refer to being attached via a covalent bond. As used herein, the term "coupled" refers to a physical attachment, such that the two are bonded together. In some embodiments, the bond is a covalent bond. In some embodiments, the bond is a synthetic bond. In some embodiments, the bond is a chemical bond.

In another embodiment, by "chemically attach to" it is meant to refer to being attached to ("wiring") the electrode via a synthetic linker (also referred "electrode linker" or "mediator molecule" or "mediator") being configured to link the recombinant protein to an electrode.

In one embodiment, the wiring can be obtained by a non-specific process, by using a chemical modification and conductive matrices such as, without limitation, graphene oxide and multi-walled carbon nanotubes.

In one embodiment, the wiring is a site-specific wiring, performed e.g., by inserting at least one non-canonical amino acid in a desired site of one of the groups (A to D) that, optionally, covalently links to a moiety that binds to an electrode as described herein.

Without being bound by any particular mechanism, it is assumed that the recombinant protein disclosed herein (e.g., in the form of A-B-C-D) allows direct electron transfer (DET) via a domain that affords DET, resulting in a "built in" redox mediator.

In some embodiments, in order to achieve an efficient DET, the distance between the enzyme's active site and the electrode is as short as a few Angstroms (e.g., 1 to 20 Å). In some embodiments, the distance is between 0-20, 0-19, 0-18, 0-17, 0-16, 0-15, 0-14, 0-13, 0-12, 0-11, 0-10, 1-20, 1-19, 1-18, 1- 17, 1-16, 1-15, 1-14, 1-13, 1-12, 1-11, 1-10, 2-20, 2-19, 2-18, 2-17, 2-16, 2-15, 2-14, 2-13, 2-12, 2-11, 3-10, 3-20, 3-19, 3-18, 3-17, 3-16, 3-15, 3-14, 3-13, 3-12, 3-11, or 3-10 Å. Each possibility represents a separate embodiment of the invention.

In some embodiments, when linked to the enzyme, the ET domain is minimal so as not to introduce additional insulation to the system by a complex proteinaceous matrix. In some embodiments, the ET domain is linked by a flexible linker. As described herein, the flexibility allows avoiding interruption of the catalytic redox activity. In some embodiments, the minimal domain is not more than 10, 12, 15, 17, 20, 22, 25, 27, 30, 32, 35, 37, 40, 42, 45, 47 or 50 amino acids. Each possibility represents a separate embodiment of the invention.

Embodiments of "minimal domain" are described hereinabove e.g., for the c-type cytochrome.

In some embodiments, the cofactor is selected from, without being limited thereto, FAD, $NAD^+$, and $NADP^+$.

In one embodiment, the redox enzyme refers to an enzyme that can catalyze a redox reaction.

In one embodiment, the redox enzyme may be selected from, without being limited thereto, oxidase, dehydrogenase, and malic enzyme (e.g., malate dehydrogenase). In some embodiments, the redox enzyme is selected from an oxidase, a dehydrogenase, a reductase, a peroxidase, a glyoxalase, a hydroxylase and a malic enzyme. In some embodiments, the redox enzyme is sugar dehydrogenase. In some embodiments, the sugar is glucose. In some embodiments, enzyme is alcohol dehydrogenase.

In one embodiment, the redox enzyme in the immobilized group is characterized by a redox potential of less than 50 mV. In one embodiment, the redox enzyme in the immobilized group is characterized by a redox potential of 50 mV, 40 mV, 30 mV, 20 mV, 10 mV, 0 V, −10 mV, −20 mV, −30 mV, −40 mV, −50 mV, −60 mV, −70 mV, −80 mV, −90 mV, −100 mV, −110 mV, −120 mV, −130 mV, −140 mV, −150 mV, −160 mV, −170 mV, −180 mV, −190 mV, or −200 mV (induced potential vs. Ag/AgCl) including any value and range therebetween.

In one embodiment, the dehydrogenase is selected from, without being limited thereto, alcohol dehydrogenase, glutamic acid dehydrogenase, cholesterol dehydrogenase, aldehyde dehydrogenase, glucose dehydrogenase, fructose dehydrogenase, sorbitol dehydrogenase, lactate dehydrogenase, and glycerol dehydrogenase.

In one embodiment, the linker moiety comprises a peptide. In one embodiment, the peptide comprises serine. In one embodiment, the linker moiety comprises a short peptide e.g. having 5 to 20 amino acids, or 5 to 15 amino acids, e.g., 5, 6, 7, 8, 9, 10, 11, 12, 13, 14, or 15 amino acids, including any range therebetween. In some embodiments, the linker is selected from any embodiments of a linker described hereinabove. In some embodiments, the linker moiety is a flexible linker. In some embodiments, the linker moiety is hydrophilic. In some embodiments, the linker moiety is synthetic. In some embodiments, the linker moiety is not from cellobiose dehydrogenase. In some embodiments, the linker moiety is not from pyranose dehydrogenase. In some embodiments, the linker moiety does not interfere with enzyme function and/or DET.

A non-limiting example of a linker is a peptide comprising GSGYGSG (SEQ ID NO: 27).

In one embodiment, the linker is characterized by a length of: 5 to 40, or 20 to 30 Å, e.g., 5, 10, 15, 20, 25, 30, 35, or 40 Å, including any value and range therebetween.

In one embodiment, the electron transfer domain comprises a cytochrome, e.g., MCD.

Embodiments of the cytochrome are described hereinabove. In some embodiments, the electron transfer domain comprises a cytochrome c. In some embodiments, the electron transfer domain does not comprise a cytochrome b. In some embodiments, the recombinant protein is not a naturally occurring protein.

In one embodiment, the device is a biosensor.

As used herein and in the art, biosensors are analytical devices that combine a biological material (e.g., tissues, microorganisms, enzymes, antibodies, nucleic acids etc.) or a biologically-derived material with a physicochemical transducer or transducing microsystem.

In one embodiment, the device comprises or is configured to attach to an electronic circuitry for energizing the electrode and measuring the response.

In some embodiments, the biosensor is for measuring the concentration of a sugar in a medium.

In some embodiments, the biosensor is for measuring the concentration of glucose in a medium. In some embodiments, the biosensor is for measuring the concentration of alcohol in a medium.

In some embodiments the medium is a bodily fluid. In some embodiments, the bodily fluid is selected from at least one of: blood, serum, gastric fluid, intestinal fluid, saliva, bile, tumor fluid, urine, breast milk, interstitial fluid, and stool. In some embodiments, the biosensor is capable of measuring whole blood, serum or plasma glucose without dilution or sample processing, which can evaluate the current status of glucose or an individual suffering from diabetes. In some embodiments, the bodily fluid is undiluted. In some embodiments, the bodily fluid is diluted with a buffer.

In some embodiments, the biosensor comprises an anode compartment and a cathode compartment, the compartments being in fluid communication, wherein the anode compartment comprises an anode electrode and a substrate; and wherein the cathode compartment comprises a cathode electrode, the anode electrode and cathode electrode in electrical communication.

In some embodiments, the electrode disclosed herein is the anode.

According to an aspect, the present invention provides a method for determining an analyte in a liquid medium, the analyte being capable to undergo a biocatalytic oxidation or reduction reaction in the presence of an oxidizer or a reducer, respectively, the method comprising:
(i) providing the disclosed device in an embodiment thereof;
(ii) contacting the device with the liquid medium;
(iii) measuring the electric signal generated between the cathode and the anode, the electric signal being indicative of the presence and/or the concentration of the analyte; and
(iv) determining the analyte based on the electric signal.

In some embodiments, the method is for determining the presence of the analyte in the medium. In some embodiments, the method is for determining the concentration of the analyte in the medium. When the liquid medium is, for example, a body fluid e.g. blood, lymph fluid or cerebrospinal fluid, and the method may be carried out in an invasive manner, the method comprises inserting the biosensor into the body and bringing it into contact with the body fluid and determining the analyte in the body fluid within the body. Alternatively, body fluids or any other analyte may be tested non-invasively, and in such cases the method may comprise adding a buffer to the fluid. In some embodiments, the buffer has pH 4 to 8. In some embodiments, the buffer has pH 5 (±1).

In some embodiments, the contacting is in vivo. In some embodiments, the contacting is ex vivo. In some embodiments, a detected electrical signal indicates the analyte is present. In some embodiments, the greater the electrical signal the greater the concentration of analyte. In some embodiments, the electrical signal is compared to a predetermined standard that indicates the concentration of the analyte based on the electrical signal.

Non-limiting examples of analytes are sugar molecules e.g., galactose, lactose, maltose and xylose glucose, fructose, maltose; lactate; bilirubin; alcohols or amino acids.

In some embodiments, provided herein is a method for transferring an electron to an electrode, comprising coupling the disclosed recombinant protein in an embodiment thereof to an electrode, thereby transferring an electron to an electrode. In one embodiment, coupling is in the absence of a mediator molecule.

In some embodiments, the amino acid sequence of the recombinant protein comprises or consists of the following sequence:

MADTDTQKADVVVVGSGVAGAIVAHQLAMAGKSVILLEAGF$X_1$MPRWE

IVERFRNQVDKTDFMAPYPSSAWAPHPEYGPPNDYLILKGEHKFNSQY

IRAVGGTTWHWAASAWRFIPNDFKMKTVYGVGRDWPIQYDDIEHYYQR

AEEELGVWGPGPEEDLYSPRKEPYPMPPLPLSFNEQTIKSALNGYDPK

FHVVTEPVARNSRPYDGRPTCCGNNNCMPICPIGAMYNGIVHVEKAEQ

AGAKLID$X_2$AVVYKLETGPDKRITAAVYKDKTGADHRVEGKYFVIAAN

GIETPKILLMSANRDFPNGVANSSDMVGRNLMDHPGTGVSFYANEKLW

PGRGPQEMTSLIGFRDGPFRANEAAKKIHLSNMSRINQETQKIFKGGK

LMKPEELDAQIF$X_3$RSARFVQFDCFHEILPQPENRIVPSKTATDAVGI

PRPEITYAIDDYVKRGAVHTREVYATAAKVLGGTEVVFNDEFAPNNHI

TGATIMGADARDSVVDKDCRAFDHPNLFISSSSTMPTVGTVNVTLTIA

ALALRMSDTLKKEVEFGSGYGSGPPGPIRAGA$X_4$M $X_5$HRDRGPCGAC

HAIIQGSGSGHHHHHH (SEQ ID NO: 12, full).

In some embodiments, the amino acid sequence of the recombinant protein comprises or consists of the following sequence:

MADTDTQKADVVVVGSGVAGAIVAHQLAMAGKSVILLEAGF$X_1$MPRWE

IVERFRNQVDKTDFMAPYPSSAWAPHPEYGPPNDYLILKGEHKFNSQY

IRAVGGTTWHWAASAWRFIPNDFKMKTVYGVGRDWPIQYDDIEHYYQR

AEEELGVWGPGPEEDLYSPRKEPYPMPPLPLSFNEQTIKSALNGYDPK

FHVVTEPVARNSRPYDGRPTCCGNNNCMPICPIGAMYNGIVHVEKAEQ

AGAKLID$X_2$AVVYKLETGPDKRITAAVYKDKTGADHRVEGKYFVIAAN

GIETPKILLMSANRDFPNGVANSSDMVGRNLMDHPGTGVSFYANEKLW

PGRGPQEMTSLIGFRDGPFRANEAAKKIHLSNMSRINQETQKIFKGGK

LMKPEELDAQIF$X_3$RSARFVQFDCFHEILPQPENRIVPSKTATDAVGI

PRPEITYAIDDYVKRGAVHTREVYATAAKVLGGTEVVFNDEFAPNNHI

TGATIMGADARDSVVDKDCRAFDHPNLFISSSSTMPTVGTVNVTLTIA

ALALRMSDTLKKEVEFGSGYGSGPPGPIRAGA$X_4$M $X_5$HRDRGPCGAC

HAIIQ (SEQ ID NO: 13, partial).

In some embodiments, $X_1$ is R. In some embodiments, $X_2$ is S. In some embodiments, $X_3$ is D. In some embodiments, $X_4$ is T. In some embodiments, $X_5$ is P.

In some embodiments, one or more amino acids selected from $X_1$ to $X_5$ comprise at least one non-canonical amino acid (ncAA) residue.

Exemplary embodiments of SEQ ID NO: 12-13 are presented in the Examples section below (e.g., SEQ ID NOs: 19-23).

The term "non-canonical amino acid residue" refers to amino acid residues in D- or L-form that are not among the 20 canonical amino acids generally incorporated into naturally occurring proteins, for example, β-amino acids, homoamino acids, cyclic amino acids and amino acids with derivatized side chains.

Non-canonical amino acid residues may be incorporated into a peptide within the scope of the invention by employing known techniques of protein engineering that use recombinantly expressing cells.

In some embodiments one or more from $X_1$ to $X_5$ are present in proximity to the protein domain selected from, without being limited thereto: FAD binding domain, or MCD. In some embodiments one or more from $X_1$ to $X_5$ are present in a site that is distant from either FAD domain or MCD.

In some embodiments, by "proximity" it is meant to refer to a distance of 10 to 25 Å, e.g., 10, 15, 20, or 25 Å, including any value and range therebetween.

In some embodiments, by "distant" it is meant to refer to a distance of 30 to 100 Å, e.g., 10, 15, 20, 25, 30, 35, 40, 45, 50, 55, 60, 65, 70, 75, 80, 85, 90, 95, or 100 Å.

In some embodiments, the ncAA is a clickable ncAA.

By "clickable ncAA" it is meant to refer to ncAA attachable to another group or moiety by biorthogonal chemical mechanism.

In exemplary embodiments, the ncAA comprises Propargyl-lysine (PrK).

In some embodiments, the ncAA has attached thereto an electrode linker (mediator) configured to couple the recombinant protein to an electrode.

In some embodiments, the linker comprises an aromatic group.

In some embodiments, the aromatic group comprises polycyclic aromatic hydrocarbon system.

In some embodiments, by "polycyclic aromatic hydrocarbon system" it is meant to refer to a system comprising e.g., 3, 4, 5, or 6, fused benzene rings, which, in some embodiments, is in the form in a flat aromatic system.

In some embodiments, the aromatic group is selected from, without being limited thereto, pyrene, perylene, benzopyrene, oxoperylene, rubrene, perylene bisimide, styrene, anthracene, tetracene, pentacene, or any derivative thereof.

In exemplary embodiments, the aromatic group comprises pyrene or a derivative thereof.

In some embodiments, the linker further comprises an azide group.

In some embodiments, the azide group allows to bind to the PrK, for example, via an alkyne group, e.g., by "click" chemistry.

In some embodiments, the aromatic system (e.g., pyrene group) is present in one pole of the linker, and the azide group is present at the other pole of the mediator.

In some embodiments, the two groups (e.g., azide group and the aromatic group) are connected to each other by an alkyl oxide, for example, and without being limited thereto, tri-ethylene oxide, di-ethylene oxide or mono-ethylene oxide. In some embodiments, the mediator is characterized by a length of 3 to 9 or 4 to 8 Å, for example 3, 4, 5, 6, 7, 8, or 9 Å, including any value and range therebetween.

The Porphyrin

In one embodiment, the recombinant protein (e.g., the cytochrome domain) is bound to a porphyrin comprising a metal. In one embodiment, the recombinant protein is bound to a compound of formula I:

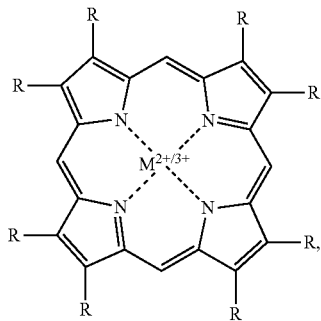

wherein R is any electron donor, or a compound as further described herein, wherein the compound of formula I is bound to a metal. In one embodiment, the recombinant protein but not the gamma subunit is bound to a porphyrin as described herein.

In one embodiment, R represents, independently and in each occurrence, a substituent selected from the group consisting of: alkyl, cycloalkyl, aryl, heteroalicyclic, heteroaryl, alkoxy, hydroxy, phosphonate, thiohydroxy, thioalkoxy, aryloxy, thioaryloxy, amino, nitro, halo, trihalomethyl, cyano, amide, amine, alkanoamine, carboxy, sulfonyl, sulfoxy, sulfinyl, and sulfonamide, or is absent. In one embodiment, R represents, independently and in each occurrence, hydrogen.

In one embodiment, R represents —($C_1$-$C_6$)alkyl. In some embodiments, R represents —($C_1$-$C_6$)alkoxy. In some embodiments, R represents —($C_1$-$C_6$)alkylthio. In some embodiments, R represents —($C_1$-$C_6$)alkylsulfinyl. In some embodiments, R represents —($C_1$-$C_6$)alkylsulfonyl. In some embodiments, R represents —[(C1-C6)alkyl]NH. In some embodiments, R represents —[(C1-C6)alkyl]COOH.

In one embodiment, the term "alkyl" comprises an aliphatic hydrocarbon including straight chain and branched chain groups. Preferably, the alkyl group has 21 to 100 carbon atoms, and more preferably 21-50 carbon atoms. Whenever a numerical range; e.g., "21-100", is stated herein, it implies that the group, in this case the alkyl group, may contain 21 carbon atoms, 22 carbon atoms, 23 carbon atoms, etc., up to and including 100 carbon atoms.

In one embodiment, the term "long alkyl" comprises an alkyl having at least 20 carbon atoms in its main chain (the longest path of continuous covalently attached atoms). A short alkyl therefore has 20 or less main-chain carbons. In one embodiment, an alkyl can be substituted or unsubstituted. In one embodiment, the term "alkyl", as used herein, also encompasses saturated or unsaturated hydrocarbon, hence this term further encompasses alkenyl and alkynyl.

In one embodiment, the term "alkenyl" describes an unsaturated alkyl, as defined herein, having at least two carbon atoms and at least one carbon-carbon double bond. The alkenyl may be substituted or unsubstituted by one or more substituents, as described hereinabove. In one embodiment, the term "alkynyl", as defined herein, is an unsaturated alkyl having at least two carbon atoms and at least one carbon-carbon triple bond. The alkynyl may be substituted or unsubstituted by one or more substituents.

In one embodiment, the term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted.

In one embodiment, the term "aryl" describes an all-carbon monocyclic or fused-ring polycyclic (i.e., rings which share adjacent pairs of carbon atoms) groups having a completely conjugated pi-electron system. In one embodiment, an aryl group may be substituted or unsubstituted.

In one embodiment, the term alkoxy" describes both an —O-alkyl and an —O-cycloalkyl group. In one embodiment, the term "aryloxy" describes an —O-aryl. In one embodiment, the term alkyl, cycloalkyl and aryl groups in the general formulas herein may be substituted by one or more substituents, whereby each substituent group can independently be, for example, halide, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule.

In one embodiment, "halide", "halogen" or "halo" describes fluorine, chlorine, bromine or iodine. In one embodiment, "haloalkyl" describes an alkyl group as defined herein, further substituted by one or more halide(s). In one embodiment, "haloalkoxy" describes an alkoxy group as defined herein, further substituted by one or more halide(s). In one embodiment, the term "hydroxyl" or "hydroxy" describes a —OH group. In one embodiment, the term "thiohydroxy" or "thiol" describes a —SH group. In one embodiment, the term "thioalkoxy" describes both an —S-alkyl group, and a —S-cycloalkyl group. In one embodiment, the term "thioaryloxy" describes both an —S-aryl and a —S-heteroaryl group. In one embodiment, the term "amine" describes a —NR'R" group, with R' and R". In one embodiment, the term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

In one embodiment, the term "heteroalicyclic" or "heterocyclyl" describes a monocyclic or fused ring group having in the ring(s) one or more atoms such as nitrogen, oxygen and sulfur. The rings may also have one or more double bonds. In one embodiment, the rings do not have a completely conjugated pi-electron system. Representative examples are piperidine, piperazine, tetrahydrofurane, tetrahydropyrane, morpholino and the like.

In one embodiment, the term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon).

In one embodiment, the term "carbonyl" describes a —C(=O)—R' group, where R' is as defined hereinabove. In one embodiment, the above-terms also encompass thio-derivatives thereof (thiocarboxy and thiocarbonyl).

In one embodiment, the term "thiocarbonyl" describes a —C(=S)—R' group, where R' is as defined hereinabove. In one embodiment, the term "thiocarboxy" group describes a —C(=S)—OR' group, where R' is as defined herein. In one embodiment, the term sulfinyl" group describes an —S(=O)—R' group, where R' is as defined herein. In one embodiment, the term sulfonyl" or "sulfonate" group describes an —S(=O)$_2$—R' group, where R' is as defined herein. In one embodiment, the term "carbamyl" or "carbamate" group describes an —OC(=O)—NR'R" group, where R' is as defined herein and R" is as defined for R'.

In one embodiment, the term "nitro" group refers to a —NO$_2$ group. In one embodiment, the term "cyano" or "nitrile" group refers to a —C≡N group. In one embodiment, the term azide" refers to a —N$_3$ group. In one embodiment, the term "sulfonamide" refers to a —S(=O)$_2$—NR'R" group, with R' and R" as defined herein.

In one embodiment, the term "phosphonyl" or "phosphonate" describes an —O—P(=O)(OR')$_2$ group, with R' as defined hereinabove. In one embodiment, the term "phosphinyl" describes a —PR'R" group, with R' and R" as defined hereinabove.

In one embodiment, the term "alkaryl" describes an alkyl, as defined herein, which substituted by an aryl, as described herein. In one embodiment, alkaryl is benzyl.

In one embodiment, the term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

In one embodiment, the terms "halo" and "halide", which are referred to herein interchangeably, describe an atom of a halogen, that is fluorine, chlorine, bromine or iodine, also referred to herein as fluoride, chloride, bromide and iodide. In one embodiment, the term "haloalkyl" describes an alkyl group as defined above, further substituted by one or more halide(s).

In one embodiment, the metal is a trivalent metal or a divalent metal.

In one embodiment, the recombinant protein as described herein comprises both peroxidase activity and oxidative activity. In one embodiment, the recombinant protein bound to a porphyrin comprising a metal comprises both peroxidase activity and oxidative activity. In one embodiment, the recombinant protein bound to a porphyrin comprising a metal comprises both peroxidase activity and oxidase activity.

In one embodiment, the recombinant protein is characterized by Michaelis-Menten constant $K_M^{app}$pp value which is at least 2, 3, 4 or 5, or more, higher compared to plain GDH, as measured under the same condition (e.g., glucose concentration) of glucose oxidation.

In one embodiment, the recombinant protein is characterized by higher selectivity towards glucose oxidation as compared to other sugar's molecules. In one embodiment, the means that the rate of glucose oxidation is higher by at least 10%, by at least 20%, by at least 30%, by at least 40%, or by at least 50% than a other sugar molecule.

As used herein, the terms "peptide", "polypeptide" and "protein" are used interchangeably to refer to a polymer of amino acid residues. In some embodiment, the peptides, polypeptides and proteins described herein have modifications rendering them more stable while in the body or more capable of penetrating into cells. In some embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

As used herein, the term "recombinant protein" refers to protein which is coded for by a recombinant DNA, and is thus not naturally occurring. The term "recombinant DNA" refers to DNA molecules formed by laboratory methods of genetic recombination. Generally, this recombinant DNA is in the form of a vector used to express the recombinant protein in a cell. In one embodiment, the recombinant protein is provided within a single composition or kit with the gamma subunit FAD-GDH. In one embodiment, the recombinant protein with the gamma subunit FAD-GDH are provided within a single composition or kit as two separate proteins (unbound).

In some embodiments, the recombinant protein is a hybrid protein. In some embodiments, the recombinant protein is a chimeric protein. In some embodiments, the c-type cytochrome peptide is from a different protein than the alpha subunit. In some embodiments, the c-type cytochrome peptide is not from FAD-GDH. In some embodiments, the c-type cytochrome peptide is not from GDH. In some embodiments, the nucleic acid sequence encoding the alpha subunit and the sequence encoding the c-type cytochrome peptide are operably linked, such that a full-length protein is produced following translation and/or transcription. The term "operably linked" is intended to mean that the two nucleotide sequences of interest are linked to each other in a manner that allows for expression of the nucleotide sequence (e.g. in an in vitro transcription/translation system or in a host cell when the vector is introduced into the host cell).

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid" which refers to a circular double stranded DNA loop into which additional DNA segments can be inserted, such as by standard molecular cloning techniques. Another type of vector, wherein virally-derived DNA or RNA sequences are present in the virus (e.g. retroviruses, replication defective retroviruses, adenoviruses, replication defective adenoviruses, and adeno-associated viruses). Viral vectors also include polynucleotides carried by a virus for transfecting into host cells. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". Common expression vectors of utility in recombinant DNA techniques are often in the form of plasmids.

Recombinant expression vectors can comprise a nucleic acid coding for the protein of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

A vector or a plasmid is an artificial composite. A vector or a plasmid as described herein is man-made. A vector or a plasmid as described herein is not a product of nature.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

General methods in molecular and cellular biochemistry, such as may be useful for carrying out DNA and protein recombination, as well as other techniques described herein, can be found in such standard textbooks as Molecular Cloning: A Laboratory Manual, 3rd Ed. (Sambrook et al., HaRBor Laboratory Press 2001); Short Protocols in Molecular Biology, 4th Ed (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998).

It should be well understood to one skilled in the art that a recombinant protein is produced by expressing the recombinant DNA in a cell and then purifying the protein. The cells expressing the DNA are cultured under effective conditions, which allow for the expression of high amounts of recombinant polypeptide. Such effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

Purification of a recombinant protein involves standard laboratory techniques for extracting a recombinant protein that is essentially free from contaminating cellular components, such as carbohydrate, lipid, or other proteinaceous impurities associated with the peptide in nature. Purification can be carried out using a tag that is part of the recombinant protein or thought immuno-purification with antibodies directed to the recombinant protein. Kits are commercially available for such purifications and will be familiar to one skilled in the art. Typically, a preparation of purified peptide contains the peptide in a highly-purified form, i.e., at least about 80% pure, at least about 90% pure, at least about 95% pure, greater than 95% pure, or greater than 99% pure.

In some embodiments, the protein comprises an amino acid sequence with at least 60%, at least 65%, at least 70%, at least 75%, at least 80%, at least 85%, at least 90%, at least 95%, at least 99% homology to the amino acid sequence set forth below in SEQ ID NO: 1. In some embodiments, the amino acid sequence with at least 70% homology to SEQ ID NO: 1 is the amino acid sequence set forth in SEQ ID NO: 6.

Mutations and deletions in a recombinant protein are created by introducing the mutation or deletion into the recombinant DNA. Methods of site-directed mutagenesis, and routine DNA recombination can be found in such standard textbooks as are enumerated above. Mutagenesis of one amino acid to another may require mutation of 1, 2, or 3 of the bases that make up the codon corresponding to the amino acid to be changed.

In some embodiments, provided herein a method for quantifying the amount of a reporter in a sample having a first detectable range of light absorbance in an oxidized state a second range of light absorbance in a non-oxidized state and, comprising: contacting the recombinant protein with the reporter in a non-oxidized state; and measuring the amount of the reporter in an oxidized state, thereby quantifying the amount of a reporter in a sample. In some embodiments, coupled is directly bound. In another embodiment, first detectable range of light absorbance is detectable in visible light and the second range of light absorbance is non-detectable in visible light. In some embodiments, the reporter is 2,6-Dichloroindophenol. In some embodiments, the reporter is coupled to glucose. In some embodiments, 2,6-Dichloroindopheno is coupled to glucose.

DNA Sequences

In one embodiment, provided herein is a DNA molecule encoding the recombinant protein. In one embodiment, provided herein is a DNA molecule comprising: a transcription regulatory element, a translation regulatory element or both; operably linked to a nucleotide sequence encoding the recombinant protein. In one embodiment, the invention provides a DNA molecule encoding both the recombinant protein and the gamma subunit of an FAD-GDH. In one embodiment, the invention provides a single DNA molecule encoding both the recombinant protein and the gamma subunit of an FAD-GDH as two separate proteins.

In one embodiment, provided herein is a DNA molecule comprising a nucleic acid sequence encoding the recombinant protein. In one embodiment, provided herein is a DNA molecule comprising a nucleic acid sequence encoding the recombinant protein and the gamma subunit of an FAD-GDH. In one embodiment, provided herein is a DNA molecule comprising the nucleic acid sequence selected from the group consisting SEQ ID NOs: 5-7. In one embodiment, the invention provides a plasmid or a vector (such as an expression vector) comprising a nucleic acid sequence encoding the recombinant protein. In one embodiment, provided herein is a cell comprising a DNA molecule, a plasmid or a vector as described herein. In one embodiment, the cell is a prokaryotic cell. In one embodiment, the cell is a bacterial cell.

In one embodiment, the alpha subunit of the FAD-GDH is encoded by a DNA sequence comprising or consisting of the nucleotide sequence:

```
                                              (SEQ ID NO: 1)
ATGGCGGATACGGATACCCAGAAAGCGGACGTGGTCGTGGTTGGATCCGG

CGTGGCAGGCGCAATCGTGGCTCATCAACTGGCAATGGCAGGTAAAAGCG

TGATCCTGCTGGAAGCTGGTCCGCGTATGCCGCGTTGGGAAATTGTTGAA

CGTTTCCGCAATCAAGTCGATAAAACCGACTTTATGGCACCGTATCCGAG

CAGCGCATGGGCACCGCATCCGGAATATGGTCCGCCGAATGATTACCTGA

TCCTGAAAGGCGAACACAAATTTAACTCACAGTACATTCGTGCAGTGGGC

GGCACCACGTGGCATTGGGCAGCCTCGGCATGGCGCTTCATCCCGAACGA

TTTTAAAATGAAAACCGTGTATGGCGTTGGTCGTGACTGGCCGATTCAGT

ACGATGACATCGAACATTATTACCAACGCGCGGAAGAAGAACTGGGCGTG

TGGGGTCCGGGCCCGGAAGAAGACCTGTATTCACCGCGTAAAGAACCGTA

CCCGATGCCGCCGCTGCCGCTGAGTTTCAATGAACAAACCATTAAATCCG

CTCTGAACGGCTATGATCCGAAATTTCACGTGGTTACGGAACCGGTGGCC

CGTAATTCGCGCCCGTACGACGGTCGCCCGACCTGCTGTGGCAACAATAA

CTGCATGCCGATTTGTCCGATCGGTGCAATGTATAACGGCATCGTCCATG

TGGAAAAAGCTGAACAGGCAGGTGCTAAACTGATTGATAGTGCGGTCGTG

TACAAACTGGAAACGGGCCCGGACAAACGTATTACCGCAGCTGTTTATAA

AGATAAAACGGGTGCGGACCATCGCGTCGAAGGCAAATACTTCGTGATTG

CGGCCAATGGTATCGAAACCCCGAAAATTCTGCTGATGAGCGCGAACCGT

GATTTTCCGAATGGTGTGGCCAACAGTTCCGATATGGTTGGCCGCAATCT

GATGGACCATCCGGGCACCGGCGTGAGCTTTTATGCAAACGAAAAACTGT

GGCCGGGTCGTGGTCCGCAGGAAATGACCTCTCTGATCGGTTTCCGTGAT

GGCCCGTTTCGCGCGAATGAAGCAGCGAAGAAAATTCATCTGTCAAATAT

GTCGCGTATCAACCAGGAAACCCAAAAAATCTTTAAAGGCGGTAAACTGA

TGAAACCGGAAGAACTGGATGCGCAGATCCGTGACCGCAGTGCCCGCTTT

GTTCAATTCGATTGCTTTCACGAAATCCTGCCGCAGCCGGAAAATCGTAT

TGTCCCGTCCAAAACCGCAACGGACGCAGTGGGTATTCCGCGTCCGGAAA

TTACGTATGCGATCGATGACTACGTCAAACGTGGCGCAGTGCATACGCGC

GAAGTTTATGCTACCGCGGCCAAAGTGCTGGGCGGCACCGAAGTGGTCTT

CAACGATGAATTTGCGCCGAATAACCACATCACCGGTGCCACGATTATGG

GCGCGGATGCCCGTGACTCAGTGGTTGATAAAGACTGTCGCGCCTTCGAT

CATCCGAACCTGTTTATTAGCAGCAGCAGCACCATGCCGACGGTTGGCAC

CGTTAACGTCACCCTGACGATTGCAGCTCTGGCACTGCGTATGTCTGATA

CGCTGAAAAAAGAAGTC.
```

In one embodiment, the recombinant protein is encoded by a DNA molecule comprising a coding nucleotide sequence encoding the alpha subunit of the FAD-GDH.

In one embodiment, the alpha subunit of the FAD-GDH is encoded by a DNA sequence of 1200 to 1700 nucleotides. In one embodiment, the alpha subunit of the FAD-GDH is encoded by a DNA sequence of 1200 to 1650 nucleotides. In one embodiment, the alpha subunit of the FAD-GDH is encoded by a DNA sequence of 1300 to 1650 nucleotides. In one embodiment, the alpha subunit of the FAD-GDH is encoded by a DNA sequence of 1400 to 1700 nucleotides. In one embodiment, the alpha subunit of the FAD-GDH is encoded by a DNA sequence of 1500 to 1700 nucleotides. In one embodiment, the alpha subunit of the FAD-GDH is encoded by a DNA sequence of 1500 to 1650 nucleotides. In one embodiment, the alpha subunit of the FAD-GDH is encoded by a DNA sequence of 1550 to 1640 nucleotides. In one embodiment, the alpha subunit of the FAD-GDH is encoded by a DNA sequence of 1600 to 1650 nucleotides.

In one embodiment, the alpha subunit of the FAD-GDH is a mutant of alpha FAD-GDH or a mutant of SEQ ID NO: 1. Active mutants of alpha FAD-GDH or SEQ ID NO: 1 are readily available to one of skill in the art. By the term active mutant, as used in conjunction with an FAD-GDH, is meant a mutated form of the naturally occurring FAD-GDH. FAD-GDH mutant or variants will typically but not exclusively have at least 70%, e.g., 80%, 85%, 90% to 95% or more, and for example 98% or more amino acid sequence identity to the amino acid sequence of the reference FAD-GDH molecule.

In one embodiment, the DNA sequence of a mutant of FAD-GDH or a mutant of SEQ ID NO: 1 is at least 70% identical to SEQ ID NO: 1. In one embodiment, the DNA sequence of a mutant of FAD-GDH or a mutant of SEQ ID NO: 1 is at least 75% identical to SEQ ID NO: 1. In one embodiment, the DNA sequence of a mutant of FAD-GDH or a mutant of SEQ ID NO: 1 is at least 80% identical to SEQ ID NO: 1. In one embodiment, the DNA sequence of a mutant of FAD-GDH or a mutant of SEQ ID NO: 1 is at least 85% identical to SEQ ID NO: 1. In one embodiment, the DNA sequence of a mutant of FAD-GDH or a mutant of SEQ ID NO: 1 is at least 90% identical to SEQ ID NO: 1. In one embodiment, the DNA sequence of a mutant of FAD-GDH or a mutant of SEQ ID NO: 1 is at least 95% identical to SEQ ID NO: 1. In one embodiment, the DNA sequence of a mutant of FAD-GDH or a mutant of SEQ ID NO: 1 is at least 97% identical to SEQ ID NO: 1.

In one embodiment, the gamma subunit of the FAD-GDH is encoded by a DNA sequence comprising or consisting of the nucleotide sequence:

```
                                              (SEQ ID NO: 2)
ATGGCTCACAATGACAACACCCCGCACTCCCGCCGTACCGGCGATGCGGC

CGTGACCGGTATTACGCGTCGCCAGTGGCTGCAAGGCGCGCTGGCCCTGA

CCGCAGCTGGCCTGACGGGTTCCCTGGCCCTGCGCGCACTGGCTGATGAT

CCGGGCACCGCACCGCTGGATACCTTTATGACGCTGAGCGAAGCTCTGAC

GGGCAAAAAAGGTCTGTCTCGTGTTCTGGGCCAGCGTTTTCTGCAAGCGC

TGCAAAAAGGTTCATTCAAAACCGCGGATTCGCTGCCGCAGCTGGCGGGC

GCCCTGGCAAGCGGTTCTCTGAACCCGGACCAAGAAGCTCTGGCGCTGAA

AATCCTGGAAGCATGGTATCTGGGCATTGTTGATAATGTGGTTATCACCT
```

```
ACGAAGAAGCCCTGATGTTTAGTGTCGTGTCCGACACGCTGGTCATTCCG

AGCTATTGCCCGAACAAACCGGGTTTCTGGGCCGAAAAACCGATCGAACG

TCAGGCATAA.
```

In one embodiment, the gamma subunit of the FAD-GDH is translated into a discrete protein. In one embodiment, the gamma subunit of the FAD-GDH is encoded by a DNA sequence of 400 to 700 nucleotides. In one embodiment, the gamma subunit of the FAD-GDH is encoded by a DNA sequence of 450 to 650 nucleotides. In one embodiment, the gamma subunit of the FAD-GDH is encoded by a DNA sequence of 450 to 550 nucleotides. In one embodiment, the gamma subunit of the FAD-GDH is encoded by a DNA sequence of 480 to 530 nucleotides. In one embodiment, the gamma subunit of the FAD-GDH is encoded by a DNA sequence of 500 to 540 nucleotides. In one embodiment, the gamma subunit of the FAD-GDH is encoded by a DNA sequence of 500 to 530 nucleotides.

In one embodiment, the gamma subunit of the FAD-GDH is a mutant of gamma FAD-GDH or a mutant of SEQ ID NO: 2. In one embodiment, active mutants of gamma FAD-GDH or SEQ ID NO: 2 are readily available to one of skill in the art.

In one embodiment, the DNA sequence of a mutant of FAD-GDH or a mutant of SEQ ID NO: 2 is at least 70% identical to SEQ ID NO: 2. In one embodiment, the DNA sequence of a mutant of FAD-GDH or a mutant of SEQ ID NO: 2 is at least 75% identical to SEQ ID NO: 2. In one embodiment, the DNA sequence of a mutant of FAD-GDH or a mutant of SEQ ID NO: 2 is at least 80% identical to SEQ ID NO: 2. In one embodiment, the DNA sequence of a mutant of FAD-GDH or a mutant of SEQ ID NO: 2 is at least 85% identical to SEQ ID NO: 2. In one embodiment, the DNA sequence of a mutant of FAD-GDH or a mutant of SEQ ID NO: 2 is at least 90% identical to SEQ ID NO: 2. In one embodiment, the DNA sequence of a mutant of FAD-GDH or a mutant of SEQ ID NO: 2 is at least 95% identical to SEQ ID NO: 2. In one embodiment, the DNA sequence of a mutant of FAD-GDH or a mutant of SEQ ID NO: 2 is at least 97% identical to SEQ ID NO: 2.

In one embodiment, the minimal cytochrome peptide is encoded by a DNA sequence comprising or consisting of the nucleotide sequence:

```
                                          (SEQ ID NO: 3)
ATTCGTGCAGGTGCTACCATGCCGCATCGTGATCGTGGTCCGTGCGGTGC

ATGTCACGCTATTATCCAG.
```

In one embodiment, the recombinant protein is encoded by a DNA sequence comprising or consisting of the nucleotide sequence:

```
CTCACAATGACAACACCCCGCACTCCCGCCGTACCGGCGATGCGGCCGTG

ACCGGTATTACGCGTCGCCAGTGGCTGCAAGGCGCGCTGGCCCTGACCGC

AGCTGGCCTGACGGGTTCCCTGGCCCTGCGCGCACTGGCTGATGATCCGG

GCACCGCACCGCTGGATACCTTTATGACGCTGAGCGAAGCTCTGACGGGC

AAAAAAGGTCTGTCTCGTGTTCTGGGCCAGCGTTTTCTGCAAGCGCTGCA

AAAAGGTTCATTCAAAACCGCGGATTCGCTGCCGCAGCTGGCGGGCGCCC

TGGCAAGCGGTTCTCTGAACCCGGACCAAGAAGCTCTGGCGCTGAAAATC

CTGGAAGCATGGTATCTGGGCATTGTTGATAATGTGGTTATCACCTACGA

AGAAGCCCTGATGTTTAGTGTCGTGTCCGACACGCTGGTCATTCCGAGCT

ATTGCCCGAACAAACCGGGTTTCTGGGCCGAAAAACCGATCGAACGTCAG

GCATAATGGCGGATACGGATACCCAGAAAGCGGACGTGGTCGTGGTTGGA

TCCGGCGTGGCAGGCGCAATCGTGGCTCATCAACTGGCAATGGCAGGTAA

AAGCGTGATCCTGCTGGAAGCTGGTCCGCGTATGCCGCGTTGGGAAATTG

TTGAACGTTTCCGCAATCAAGTCGATAAAACCGACTTTATGGCACCGTAT

CCGAGCAGCGCATGGGCACCGCATCCGGAATATGGTCCGCCGAATGATTA

CCTGATCCTGAAAGGCGAACACAAATTTAACTCACAGTACATTCGTGCAG

TGGGCGGCACCACGTGGCATTGGGCAGCCTCGGCATGGCGCTTCATCCCG

AACGATTTTAAAATGAAAACCGTGTATGGCGTTGGTCGTGACTGGCCGAT

TCAGTACGATGACATCGAACATTATTACCAACGCGCGGAAGAAGAACTGG

GCGTGTGGGGTCCGGGCCCGGAAGAAGACCTGTATTCACCGCGTAAAGAA

CCGTACCCGATGCCGCCGCTGCCGCTGAGTTTCAATGAACAAACCATTAA

ATCCGCTCTGAACGGCTATGATCCGAAATTTCACGTGGTTACGGAACCGG

TGGCCCGTAATTCGCGCCCGTACGACGGTCGCCCGACCTGCTGTGGCAAC

AATAACTGCATGCCGATTTGTCCGATCGGTGCAATGTATAACGGCATCGT

CCATGTGGAAAAAGCTGAACAGGCAGGTGCTAAACTGATTGATAGTGCGG

TCGTGTACAAACTGGAAACGGGCCCGGACAAACGTATTACCGCAGCTGTT

TATAAAGATAAAACGGGTGCGGACCATCGCGTCGAAGGCAAATACTTCGT

GATTGCGGCCAATGGTATCGAAACCCCGAAAATTCTGCTGATGAGCGCGA

ACCGTGATTTTCCGAATGGTGTGGCCAACAGTTCCGATATGGTTGGCCGC

AATCTGATGGACCATCCGGGCACCGGCGTGAGCTTTTATGCAAACGAAAA

ACTGTGGCCGGGTCGTGGTCCGCAGGAAATGACCTCTCTGATCGGTTTCC

GTGATGGCCCGTTTCGCGCGAATGAAGCAGCGAAGAAAATTCATCTGTCA

AATATGTCGCGTATCAACCAGGAAACCCAAAAAATCTTTAAAGGCGGTAA

ACTGATGAAACCGGAAGAACTGGATGCGCAGATCCGTGACCGCAGTGCCC

GCTTTGTTCAATTCGATTGCTTTCACGAAATCCTGCCGCAGCCGGAAAAT

CGTATTGTCCCGTCCAAAACCGCAACGGACGCAGTGGGTATTCCGCGTCC

GGAAATTACGTATGCGATCGATGACTACGTCAAACGTGGCGCAGTGCATA

CGCGCGAAGTTTATGCTACCGCGGCCAAAGTGCTGGGCGGCACCGAAGTG

GTCTTCAACGATGAATTTGCGCCGAATAACCACATCACCGGTGCCACGAT

TATGGGCGCGGATGCCCGTGACTCAGTGGTTGATAAAGACTGTCGCGCCT

TCGATCATCCGAACCTGTTTATTAGCAGCAGCAGCACCATGCCGACGGTT

GGCACCGTTAACGTCACCCTGACGATTGCAGCTCTGGCACTGCGTATGTC

TGATACGCTGAAAAAGAAGTCATTCGTGCAGGTGCTACCATGCCGCATC

GTGATCGTGGTCCGTGCGGTGCATGTCACGCTATTATCCAG (SEQ ID

NO: 5 without linker, his and restriction sites).
```

In one embodiment, the recombinant protein is encoded by a DNA sequence comprising or consisting of the nucleotide sequence:

CTCACAATGACAACACCCCGCACTCCCGCCGTACCGGCGATGCGGCCGTG
ACCGGTATTACGCGTCGCCAGTGGCTGCAAGGCGCGCTGGCCCTGACCGC
AGCTGGCCTGACGGGTTCCCTGGCCCTGCGCGCACTGGCTGATGATCCGG
GCACCGCACCGCTGGATACCTTTATGACGCTGAGCGAAGCTCTGACGGGC
AAAAAAGGTCTGTCTCGTGTTCTGGGCCAGCGTTTTCTGCAAGCGCTGCA
AAAAGGTTCATTCAAAACCGCGGATTCGCTGCCGCAGCTGGCGGGCGCCC
TGGCAAGCGGTTCTCTGAACCCGGACCAAGAAGCTCTGGCGCTGAAAATC
CTGGAAGCATGGTATCTGGGCATTGTTGATAATGTGGTTATCACCTACGA
AGAAGCCCTGATGTTTAGTGTCGTGTCCGACACGCTGGTCATTCCGAGCT
ATTGCCCGAACAAACCGGGTTTCTGGGCCGAAAAACCGATCGAACGTCAG
GCATAATGGCGGATACGGATACCCAGAAAGCGGACGTGGTCGTGGTTGGA
TCCGGCGTGGCAGGCGCAATCGTGGCTCATCAACTGGCAATGGCAGGTAA
AAGCGTGATCCTGCTGGAAGCTGGTCCGCGTATGCCGCGTTGGGAAATTG
TTGAACGTTTCCGCAATCAAGTCGATAAAACCGACTTTATGGCACCGTAT
CCGAGCAGCGCATGGGCACCGCATCCGGAATATGGTCCGCCGAATGATTA
CCTGATCCTGAAAGGCGAACACAAATTTAACTCACAGTACATTCGTGCAG
TGGGCGGCACCACGTGGCATTGGGCAGCCTCGGCATGGCGCTTCATCCCG
AACGATTTTAAAATGAAAACCGTGTATGGCGTTGGTCGTGACTGGCCGAT
TCAGTACGATGACATCGAACATTATTACCAACGCGCGGAAGAAGAACTGG
GCGTGTGGGTCCGGGCCCGGAAGAAGACCTGTATTCACCGCGTAAAGAA
CCGTACCCGATGCCGCCGCTGCCGCTGAGTTTCAATGAACAAACCATTAA
ATCCGCTCTGAACGGCTATGATCCGAAATTTCACGTGGTTACGGAACCGG
TGGCCCGTAATTCGCGCCCGTACGACGGTCGCCCGACCTGCTGTGGCAAC
AATAACTGCATGCCGATTTGTCCGATCGGTGCAATGTATAACGGCATCGT
CCATGTGGAAAAAGCTGAACAGGCAGGTGCTAAACTGATTGATAGTGCGG
TCGTGTACAAACTGGAAACGGGCCCGGACAAACGTATTACCGCAGCTGTT
TATAAAGATAAAACGGGTGCGGACCATCGCGTCGAAGGCAAATACTTCGT
GATTGCGGCCAATGGTATCGAAACCCCGAAAATTCTGCTGATGAGCGCGA
ACCGTGATTTTCCGAATGGTGTGGCCAACAGTTCCGATATGGTTGGCCGC
AATCTGATGGACCATCCGGGCACCGGCGTGAGCTTTTATGCAAACGAAAA
ACTGTGGCCGGGTCGTGGTCCGCAGGAAATGACCTCTCTGATCGGTTTCC
GTGATGGCCCGTTTCGCGCGAATGAAGCAGCGAAGAAATTCATCTGTCA
AATATGTCGCGTATCAACCAGGAAACCCAAAAAATCTTTAAAGGCGGTAA
ACTGATGAAACCGGAAGAACTGGATGCGCAGATCCGTGACCGCAGTGCCC
GCTTTGTTCAATTCGATTGCTTTCACGAAATCCTGCCGCAGCCGGAAAAT
CGTATTGTCCCGTCCAAAACCGCAACGGACGCAGTGGGTATTCCGCGTCC
GGAAATTACGTATGCGATCGATGACTACGTCAAACGTGGCGCAGTGCATA
CGCGCGAAGTTTATGCTACCGCGGCCAAAGTGCTGGGCGGCACCGAAGTG
GTCTTCAACGATGAATTTGCGCCGAATAACCACATCACCGGTGCCACGAT
TATGGGCGCGGATGCCCGTGACTCAGTGGTTGATAAAGACTGTCGCGCCT
TCGATCATCCGAACCTGTTTATTAGCAGCAGCAGCACCATGCCGACGGTT

GGCACCGTTAACGTCACCCTGACGATTGCAGCTCTGGCACTGCGTATGTC
TGATACGCTGAAAAAAGAAGTCGAATTCGGTTCTGGTTATGGCTCTGGTC
CGCCGGGTCCGATTCGTGCAGGTGCTACCATGCCGCATCGTGATCGTGGT
CCGTGCGGTGCATGTCACGCTATTATCCAG (SEQ ID NO: 6 with linker and without his and restriction sites).

In one embodiment, the recombinant protein is encoded by a DNA sequence comprising or consisting of the nucleotide sequence: CCATGG CCATGGCTCACAATGACAACACCCCGCACTCCCGCCGTACCGGCGATGCG
GCCGTGACCGGTATTACGCGTCGCCAGTGGCTGCAAGGCGCGCTGGCCCT
GACCGCAGCTGGCCTGACGGGTTCCCTGGCCCTGCGCGCACTGGCTGATG
ATCCGGGCACCGCACCGCTGGATACCTTTATGACGCTGAGCGAAGCTCTG
ACGGGCAAAAAAGGTCTGTCTCGTGTTCTGGGCCAGCGTTTTCTGCAAGC
GCTGCAAAAAGGTTCATTCAAAACCGCGGATTCGCTGCCGCAGCTGGCGG
GCGCCCTGGCAAGCGGTTCTCTGAACCCGGACCAAGAAGCTCTGGCGCTG
AAAATCCTGGAAGCATGGTATCTGGGCATTGTTGATAATGTGGTTATCAC
CTACGAAGAAGCCCTGATGTTTAGTGTCGTGTCCGACACGCTGGTCATTC
CGAGCTATTGCCCGAACAAACCGGGTTTCTGGGCCGAAAAACCGATCGAA
CGTCAGGCATAATGGCGGATACGGATACCCAGAAAGCGGACGTGGTCGTG
GTTGGATCCGGCGTGGCAGGCGCAATCGTGGCTCATCAACTGGCAATGGC
AGGTAAAAGCGTGATCCTGCTGGAAGCTGGTCCGCGTATGCCGCGTTGGG
AAATTGTTGAACGTTTCCGCAATCAAGTCGATAAAACCGACTTTATGGCA
CCGTATCCGAGCAGCGCATGGGCACCGCATCCGGAATATGGTCCGCCGAA
TGATTACCTGATCCTGAAAGGCGAACACAAATTTAACTCACAGTACATTC
GTGCAGTGGGCGGCACCACGTGGCATTGGGCAGCCTCGGCATGGCGCTTC
ATCCCGAACGATTTTAAAATGAAAACCGTGTATGGCGTTGGTCGTGACTG
GCCGATTCAGTACGATGACATCGAACATTATTACCAACGCGCGGAAGAAG
AACTGGGCGTGTGGGTCCGGGCCCGGAAGAAGACCTGTATTCACCGCGT
AAAGAACCGTACCCGATGCCGCCGCTGCCGCTGAGTTTCAATGAACAAAC
CATTAAATCCGCTCTGAACGGCTATGATCCGAAATTTCACGTGGTTACGG
AACCGGTGGCCCGTAATTCGCGCCCGTACGACGGTCGCCCGACCTGCTGT
GGCAACAATAACTGCATGCCGATTTGTCCGATCGGTGCAATGTATAACGG
CATCGTCCATGTGGAAAAAGCTGAACAGGCAGGTGCTAAACTGATTGATA
GTGCGGTCGTGTACAAACTGGAAACGGGCCCGGACAAACGTATTACCGCA
GCTGTTTATAAAGATAAAACGGGTGCGGACCATCGCGTCGAAGGCAAATA
CTTCGTGATTGCGGCCAATGGTATCGAAACCCCGAAAATTCTGCTGATGA
GCGCGAACCGTGATTTTCCGAATGGTGTGGCCAACAGTTCCGATATGGTT
GGCCGCAATCTGATGGACCATCCGGGCACCGGCGTGAGCTTTTATGCAAA
CGAAAAACTGTGGCCGGGTCGTGGTCCGCAGGAAATGACCTCTCTGATCG
GTTTCCGTGATGGCCCGTTTCGCGCGAATGAAGCAGCGAAGAAATTCAT

```
-continued
CTGTCAAATATGTCGCGTATCAACCAGGAAACCCAAAAAATCTTTAAAGG

CGGTAAACTGATGAAACCGGAAGAACTGGATGCGCAGATCCGTGACCGCA

GTGCCCGCTTTGTTCAATTCGATTGCTTTCACGAAATCCTGCCGCAGCCG

GAAAATCGTATTGTCCCGTCCAAAACCGCAACGGACGCAGTGGGTATTCC

GCGTCCGGAAATTACGTATGCGATCGATGACTACGTCAAACGTGGCGCAG

TGCATACGCGCGAAGTTTATGCTACCGCGGCCAAAGTGCTGGGCGGCACC

GAAGTGGTCTTCAACGATGAATTTGCGCCGAATAACCACATCACCGGTGC

CACGATTATGGGCGCGGATGCCCGTGACTCAGTGGTTGATAAAGACTGTC

GCGCCTTCGATCATCCGAACCTGTTTATTAGCAGCAGCAGCACCATGCCG

ACGGTTGGCACCGTTAACGTCACCCTGACGATTGCAGCTCTGGCACTGCG

TATGTCTGATACGCTGAAAAAAGAAGTCGAATTCGGTTCTGGTTATGGCT

CTGGTCCGCCGGGTCCGATTCGTGCAGGTGCTACCATGCCGCATCGTGAT

CGTGGTCCGTGCGGTGCATGTCACGCTATTATCCAGGGCAGTGGTTCCGG

CCATCACCATCACCATCACTAAAAGCTT (SEQ ID NO: 7 with linker, his and restriction sites).
```

In one embodiment, the recombinant protein with or without the gamma subunit as described herein is encoded by a DNA sequence of 1500 to 3000 nucleotides. In one embodiment, the recombinant protein with or without the gamma subunit as described herein is encoded by a DNA sequence of 1600 to 2600 nucleotides. In one embodiment, the recombinant protein with or without the gamma subunit as described herein is encoded by a DNA sequence of 1800 to 2500 nucleotides. In one embodiment, the recombinant protein is encoded by a DNA sequence of 2000 to 2400 nucleotides.

In one embodiment, the recombinant protein is 350 to 700 amino acids long. In one embodiment, the recombinant protein is 220 to 600 amino acids long. In one embodiment, the recombinant protein is 250 to 550 amino acids long. In one embodiment, the recombinant protein is 450 to 850 amino acids long. In one embodiment, the recombinant protein is 470 to 750 amino acids long. In one embodiment, the recombinant protein is 500 to 700 amino acids long. In one embodiment, the recombinant protein is 710 to 780 amino acids long. In one embodiment, the recombinant protein is 500 to 600 amino acids long. In one embodiment, the recombinant protein is 520 to 580 amino acids long. In one embodiment, the recombinant protein is 350 to 550 amino acids long.

In one embodiment, a DNA sequence encoding the recombinant protein and the gamma subunit protein as described herein of SEQ ID NOs: 5 and 6 further comprises a Methionine codon (the initiation codon nucleotide sequence) 5' to SEQ ID NOs: 5 and/or 6. In one embodiment, a DNA sequence encoding the recombinant protein of SEQ ID NOs: 5 and 6 further comprises a Methionine codon (the initiation codon nucleotide sequence) 5' to SEQ ID NOs: 5 and/or 6. In one embodiment, a DNA sequence encoding the recombinant protein of SEQ ID NOs: 5 and 6 further comprises at its 5' end, a short DNA sequence comprising any 1-10 nucleotides sequence. In one embodiment, a DNA sequence encoding the recombinant protein of SEQ ID NOs: 5 and 6 further comprises at its 5' end, a short DNA sequence comprising 1-10 nucleotides sequence. In one embodiment, the 1-10 nucleotides sequence comprises the Methionine codon.

In one embodiment, a DNA sequence or molecule as described herein comprising a coding sequence encoding the recombinant protein, further encodes the gamma subunit protein as described herein (as a separate protein).

In one embodiment, the DNA sequence encoding the recombinant protein of the invention is any DNA molecule encoding the amino acid sequence encoded by anyone of SEQ ID NOs: 5-7 or the amino acid sequence of anyone of SEQ ID NOs: 8-11. In one embodiment, the DNA sequence encoding the recombinant protein with or without the gamma subunit as described herein is at least 70% identical to anyone of SEQ ID NOs: 5-7. In one embodiment, the DNA sequence encoding the recombinant protein with or without the gamma subunit as described herein is at least 75% identical to anyone of SEQ ID NOs: 5-7. In one embodiment, the DNA sequence encoding the recombinant protein with or without the gamma subunit as described herein is at least 80% identical to anyone of SEQ ID NOs: 5-7. In one embodiment, the DNA sequence encoding the recombinant protein with or without the gamma subunit as described herein is at least 85% identical to anyone of SEQ ID NOs: 5-7. In one embodiment, the DNA sequence encoding the recombinant protein with or without the gamma subunit as described herein is at least 90% identical to anyone of SEQ ID NOs: 5-7. In one embodiment, the DNA sequence encoding the recombinant protein with or without the gamma subunit as described herein is at least 95% identical to anyone of SEQ ID NOs: 5-7. In one embodiment, the DNA sequence encoding the recombinant protein with or without the gamma subunit as described herein is at least 95% identical to anyone of SEQ ID NOs: 5-7.

In some embodiments, a DNA molecule of the invention or a DNA sequence described herein comprises or consists any sequence encoding the recombinant protein including (but not limited to) the recombinant protein comprising or consisting anyone of SEQ ID NOs: 8-11. In some embodiments, a DNA molecule of the invention or a DNA sequence described herein comprises or consists any sequence encoding the recombinant protein and the gamma subunit, as described herein, including (but not limited to) the amino acid sequences set forth in anyone of SEQ ID NOs: 8-11. In one embodiment, the recombinant protein and/or the gamma subunit, as described herein is/are translated based on the DNA sequences provided herein. In one embodiment, the recombinant protein has an amino acid sequence that is at least 70%, 80%, 90%, 95%, or 97% identical to: (a) a recombinant protein translated from the DNA sequences provided herein or (b) anyone of SEQ ID NOs: 8-11.

In some embodiments, the protein of the invention comprises a tag. In some embodiments, the DNA encoding the proteins of the invention comprises sequence encoding the tag. In some embodiments, the tag is selected from an n-terminal tag, a c-terminal tag and an internal tag. A skilled artisan will appreciate that the tag should be positioned so as not to interfere with the function of the recombinant protein. Thus, the tag will not interfere with the redox activity or the DET activity. In some embodiments, the tag is a c-terminal tag. In some embodiments, the tag is a His tag. In some embodiments, the tag is a 6× His tag. In some embodiments, the His tag comprises or consists of the amino acid sequence HHHHHH (SEQ ID NO: 28). In some embodiments, the DNA encoding the His tag comprises the sequence CAT-CACCATCACCATCAC (SEQ ID NO: 24) (e.g., in addition to SEQ ID NO: 19-23). A skilled artisan will appreciate that any sequence which encodes the tag may be used. Protein tags are well known in the art and include, but are not limited to, HA tags, His tags, GFP tags, Myc tags, biotin tags, FLAG tags, streptavidin tags, and many, many others. Tagging may be useful for purification of the protein, and the tag may be cleaved before the enzyme is used. In some embodiment, the tag is small. In some embodiments, the tag is equal to or smaller than 40, 35, 30, 25, 20, 15, 10, 7, or 5 amino acids. Each possibility represents a separate embodiment of the invention. A smaller tag may be advantageous in that it is less likely to interfere with DET.

In some embodiments, the tag is connected to the recombinant protein by a linker. The linker may be a linker such as has been described hereinabove. In some embodiments, the linker comprises or consists of the sequence GSGSG (SEQ ID NO: 29). In some embodiments, the DNA sequence that encodes the linker comprises or consists of the sequence GGCAGTGGTTCCGGC (SEQ ID NO: 25) (e.g., in addition to SEQ ID NO: 19-23). A skilled artisan will appreciate that any sequence which encodes the linker may be used. In some embodiments, the linker is produced by the restriction site introduced into the DNA to produce the recombinant protein. Indeed, there may be a linker produced by restriction site insertion between any of the different parts of the recombinant protein.

General

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, and material arts.

As used herein, the term "treating" includes abrogating, substantially inhibiting, slowing or reversing the progression of a condition, of aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Examples

Reference is now made to the following examples which, together with the above descriptions, illustrate the invention in a non-limiting fashion.

Plasmid Construction

Figure 6:
FIG. 6 is a map of expressed FGM. For the GDH, MCD sequence has been removed.

FAD-GDH γ subunit as well as its catalytic α subunit were cloned into pTrcHis6A2 vector between NcoI and HindIII restriction sites. The partial FAD-GDH gene was followed by a short flexible polypeptide linker (13 amino-acids long) and the MCR2 (minimal cytochrome domain—MCD) DNA sequence with 6xHis tag at the sequence's C-terminal, as shown in FIG. 6 in a map of the new fusion protein. For the WT GDH the same construct was used, but without the MCD sequence. Full DNA construct:

(SEQ ID NO: 26)
```
CCATGGCTCACAATGACAACACCCCGCACTCCCGCCGTACCGGCGATGCG
GCCGTGACCGGTATTACGCGTCGCCAGTGGCTGCAAGGCGCGCTGGCCCT
GACCGCAGCTGGCCTGACGGGTTCCCTGGCCCTGCGCGCACTGGCTGATG
ATCCGGGCACCGCACCGCTGGATACCTTTATGACGCTGAGCGAAGCTCTG
ACGGGCAAAAAAGGTCTGTCTCGTGTTCTGGGCCAGCGTTTTCTGCAAGC
GCTGCAAAAAGGTTCATTCAAAACCGCGGATTCGCTGCCGCAGCTGGCGG
GCGCCCTGGCAAGCGGTTCTCTGAACCCGGACCAAGAAGCTCTGGCGCTG
AAAATCCTGGAAGCATGGTATCTGGGCATTGTTGATAATGTGGTTATCAC
CTACGAAGAAGCCCTGATGTTTAGTGTCGTGTCCGACACGCTGGTCATTC
CGAGCTATTGCCCGAACAAACCGGGTTTCTGGGCCGAAAAACCGATCGAA
CGTCAGGCATAATGGCGGATACGGATACCCAGAAAGCGGACGTGGTCGTG
GTTGGATCCGGCGTGGCAGGCGCAATCGTGGCTCATCAACTGGCAATGGC
AGGTAAAAGCGTGATCCTGCTGGAAGCTGGTCCGCGTATGCCGCGTTGGG
AAATTGTTGAACGTTTCCGCAATCAAGTCGATAAAACCGACTTTATGGCA
CCGTATCCGAGCAGCGCATGGGCACCGCATCCGGAATATGGTCCGCCGAA
TGATTACCTGATCCTGAAAGGCGAACACAAATTTAACTCACAGTACATTC
GTGCAGTGGGCGGCACCACGTGGCATTGGGCAGCCTCGGCATGGCGCTTC
ATCCCGAACGATTTTAAAATGAAAACCGTGTATGGCGTTGGTCGTGACTG
GCCGATTCAGTACGATGACATCGAACATTATTACCAACGCGCGGAAGAAG
AACTGGGCGTGTGGGGTCCGGGCCCGGAAGAAGACCTGTATTCACCGCGT
AAAGAACCGTACCCGATGCCGCCGCTGCCGCTGAGTTTCAATGAACAAAC
CATTAAATCCGCTCTGAACGGCTATGATCCGAAATTTCACGTGGTTACGG
AACCGGTGGCCCGTAATTCGCGCCCGTACGACGGTCGCCCGACCTGCTGT
GGCAACAATAACTGCATGCCGATTTGTCCGATCGGTGCAATGTATAACGG
CATCGTCCATGTGGAAAAAGCTGAACAGGCAGGTGCTAAACTGATTGATA
GTGCGGTCGTGTACAAACTGGAAACGGGCCCGGACAAACGTATTACCGCA
GCTGTTTATAAAGATAAAACGGGTGCGGACCATCGCGTCGAAGGCAAATA
CTTCGTGATTGCGGCCAATGGTATCGAAACCCCGAAAATTCTGCTGATGA
GCGCGAACCGTGATTTTCCGAATGGTGTGGCCAACAGTTCCGATATGGTT
GGCCGCAATCTGATGGACCATCCGGGCACCGGCGTGAGCTTTTATGCAAA
CGAAAAACTGTGGCCGGGTCGTGGTCCGCAGGAAATGACCTCTCTGATCG
GTTTCCGTGATGGCCCGTTTCGCGCGAATGAAGCAGCGAAGAAAATTCAT
CTGTCAAATATGTCGCGTATCAACCAGGAAACCCAAAAAATCTTTAAAGG
CGGTAAACTGATGAAACCGGAAGAACTGGATGCGCAGATCCGTGACCGCA
GTGCCCGCTTTGTTCAATTCGATTGCTTTCACGAAATCCTGCCGCAGCCG
GAAAATCGTATTGTCCCGTCCAAAACCGCAACGGACGCAGTGGGTATTCC
GCGTCCGGAAATTACGTATGCGATCGATGACTACGTCAAACGTGGCGCAG
TGCATACGCGCGAAGTTTATGCTACCGCGGCCAAAGTGCTGGGCGGCACC
GAAGTGGTCTTCAACGATGAATTTGCGCCGAATAACCACATCACCGGTGC
CACGATTATGGGCGCGGATGCCCGTGACTCAGTGGTTGATAAAGACTGTC
```
-continued
```
GCGCCTTCGATCATCCGAACCTGTTTATTAGCAGCAGCAGCACCATGCCG
ACGGTTGGCACCGTTAACGTCACCCTGACGATTGCAGCTCTGGCACTGCG
TATGTCTGATACGCTGAAAAAAGAAGTCGAATTCGGTTCTGGTTATGGCT
CTGGTCCGCCGGGTCCGATTCGTGCAGGTGCTACCATGCCGCATCGTGAT
CGTGGTCCGTGCGGTGCATGTCACGCTATTATCCAGGGCAGTGGTTCCGG
CCATCACCATCACCATCACTAAAAGCTT.
```

The first 6 nucleotides and the last 6 nucleotides are NcoI and HindIII restriction sites. The Gamma subunit is expressed as a separate protein encoded from nucleotide 3 to nucleotide 512 of the DNA molecule described herein. The Alpha subunit is from nucleotide 512 to nucleotide 2128. The flexible linker is from nucleotide 2129 to nucleotide 2167. The carboxy terminal MCD linker is from nucleotide 2168 to nucleotide 2238. 6 times His-Tag from nucleotide 2239 to nucleotide 2269.

Enzyme Expression and Purification

The complete pTrcHis6A2-FAD-GDH-MCD plasmid was transformed into E. coli BL21 cells for the expression of the fusion protein (FAD-GDH-MCD). Bacteria were cultured in an auto-induction medium (Formedium™, Hunstanton, England) with 0.5% glycerol (Bio-Lab ltd., Jerusalem, Israel) and 10 µg/mL carbenicillin (Apollo, Manchester, England) and grown in 37° C., with shaking at 250 rpm, for 6 hours after which cells were transferred to 27° C. for 18 additional hours.

The cells were then centrifuged at 6000 rpm for 10 minutes, the pallet was resuspended using 20 mL 50 mM Tris-base buffer (TB, Fisher scientific, Geel, Belgium) pH=7.0, centrifuged, weighted, and resuspended using lysis buffer (300 mM KCl, 50 mM $KH_2PO_4$, 10 mM imidazole pH=7.0) in a 1:3 (weight:buffer volume) ratio. Protease inhibitors, lysozyme and supernuclease were added to the suspension in 1:500, 1:400, and 1:5000 ratios, respectively. The cells were lysed using sonication needle followed by 15 minutes of 50° C. incubation and centrifugation (11,500 rpm for 25 minutes). The supernatant was filtered using 0.22 µm filter.

The fusion enzyme was purified using IMAC purification system (Bio-Rad, Profinia, Hercules, Calif., USA) according to manufacturer instructions.

FAD-GDH Activity Assay

To assess FGM's D-glucose oxidation activity, glucose oxidation was measured in the presence of 0.6 mM 2,6-Dichloroindophenol (DCIP, Sigma-Aldrich, Rehovot, Israel), 0.6 mM phenazine methyl sulfate (PMS, Tokyo chemical industry, Tokyo, Japan), different concentrations of D-glucose and 0.2 mM FGM, all dissolved in 50 mM TB pH=7.0. Assay was performed in 37° C. using a 96-well plate reader (BioTek instruments, Winoosky, Vt., USA) with shaking between measurements, monitoring the decrease in the DCIP absorbance $\lambda=610$ nm every 15 seconds over 25 min of activity.

Heme Activity Measurements

To verify the attachment of a porphyrin to the MCD domain, heme activity was measured using 1 mM dimethoxybenzidine (DMB, Alfa Aesar, Heysham, England), 1 mM hydrogen peroxide (Sigma-Aldrich, Rehovot, Israel), and 0.2 mM of the enzyme. Measurements were performed at 37° C. using a 96-wells plate reader, monitoring the increase in DMB absorbance $\lambda=455$ nm every 15 seconds over 30 min of activity.

Peroxidase Activity Interference Measurements

To verify that FGM does not transfer electrons to oxygen, producing hydrogen peroxide, that interferes with the FAD-GDH activity assay, peroxidase activity test was performed in the absence of hydrogen peroxide. 0.17 mM DMB and 172 mM glucose were mixed with 8 µL of 0.1 mg/mL Horseradish peroxidase (HRP, Sigma-Aldrich, Rehovot, Israel) to generate a reaction mix. 8 µL of concentrated FGM or glucose oxidase (GOx) were added to the reaction mix right before measurement. Measurements were performed at 37° C. using a plate reader, monitoring the increase in DMB absorbance $\lambda=500$ nm every 15 seconds over 25 min of activity (FIG. 3C).

Electrode Preparation

Glassy carbon electrodes (GCE, 3 mm in diameter; ALS, Tokyo, Japan) were polished using 0.05 µm alumina slurry on polishing pad for two minutes, then transferred to a 20 mL glass with 10 mL double-distilled water (DDW) and sonicated for five minutes in a sonication bath. The electrodes were then dried under nitrogen gas. 10 µL of enzyme solution in wanted concentrations was dropped on the electrode surface. The electrodes were incubated in 4° C. overnight to generate an enzyme film on the GCE. Electrode's surfaces were then covered with 12-14 kDa dialysis membrane (Membrane Filtration Products, Seguin, Tex., USA) and tightened using an O-ring rubber to prevent diffusion of the enzyme to the solution.

Electrochemical Measurements

Figure 7A:
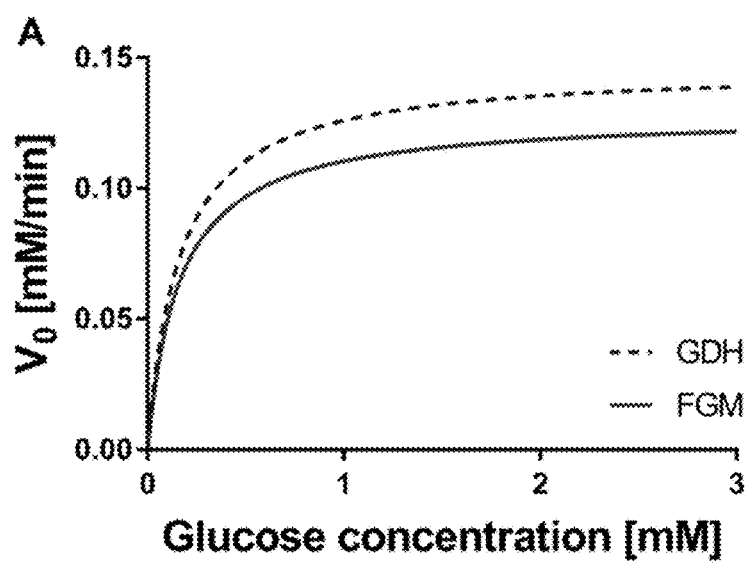
FIGS. 7A-C are graphs showing: Michaelis-Menten (FIG. 7A) and Lineweaver-Burk (FIG. 7B) plots of biochemical FAD-GDH activity for both, FGM and GDH. Linear trend line equations were calculated to be y=1.2x+6.7 for GDH and y=1.2x+7.7 for FGM and chronoamperometric measurements of glucose catalytic oxidation by FGM and GDH at an applied potential of 0.0 mV (FIG. 7C).
Figure 7B:
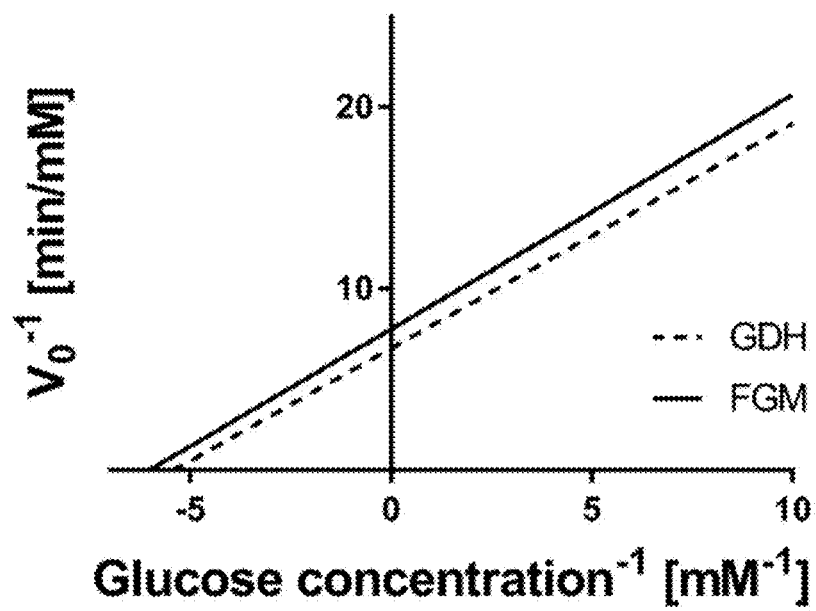
Figure 7C:
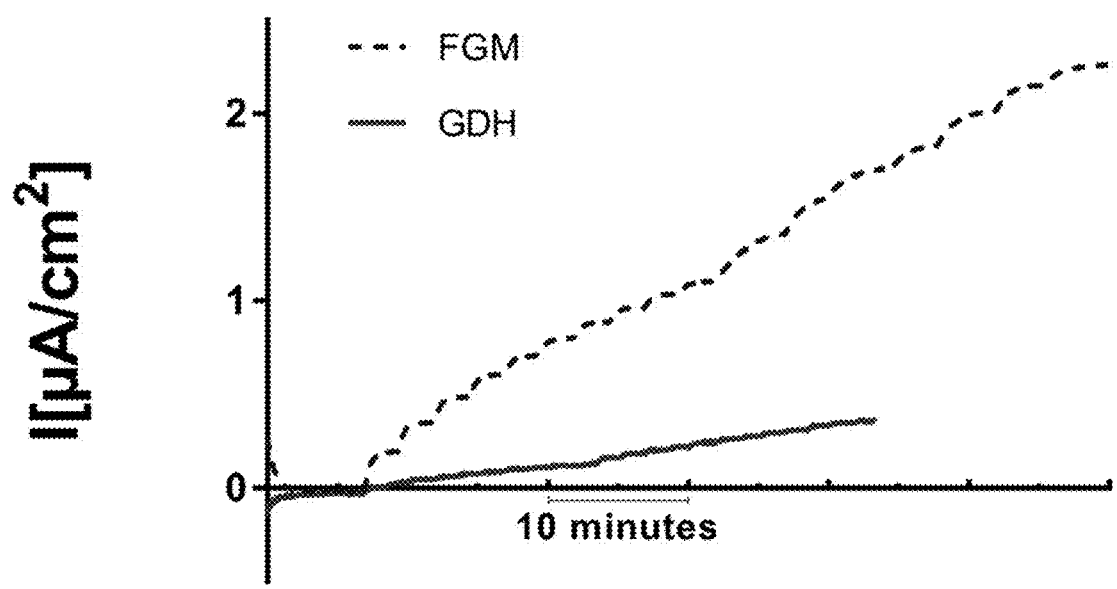

Cyclic voltammetric measurements were performed using a PalmSense2 potentiostat (Palm Instruments, Houten, The Netherlands) using a standard three electrodes system with 0.9 mm graphite rod as an auxiliary electrode, 3M KCl saturated Ag/AgCl reference electrode (ALS, Tokyo, Japan) and GCE as the working electrode in 0.15M phosphate-citrate buffer pH=5.0. Chronoamperometric measurements (FIG. 7) were performed under the same conditions with the application of 0 mV vs. Ag/AgCl with the addition of varying concentrations of glucose or potential interfering molecules. Square wave voltammetry (SWV) measurements were performed under the same conditions.

FGM Selectivity Test

Figure 8A:
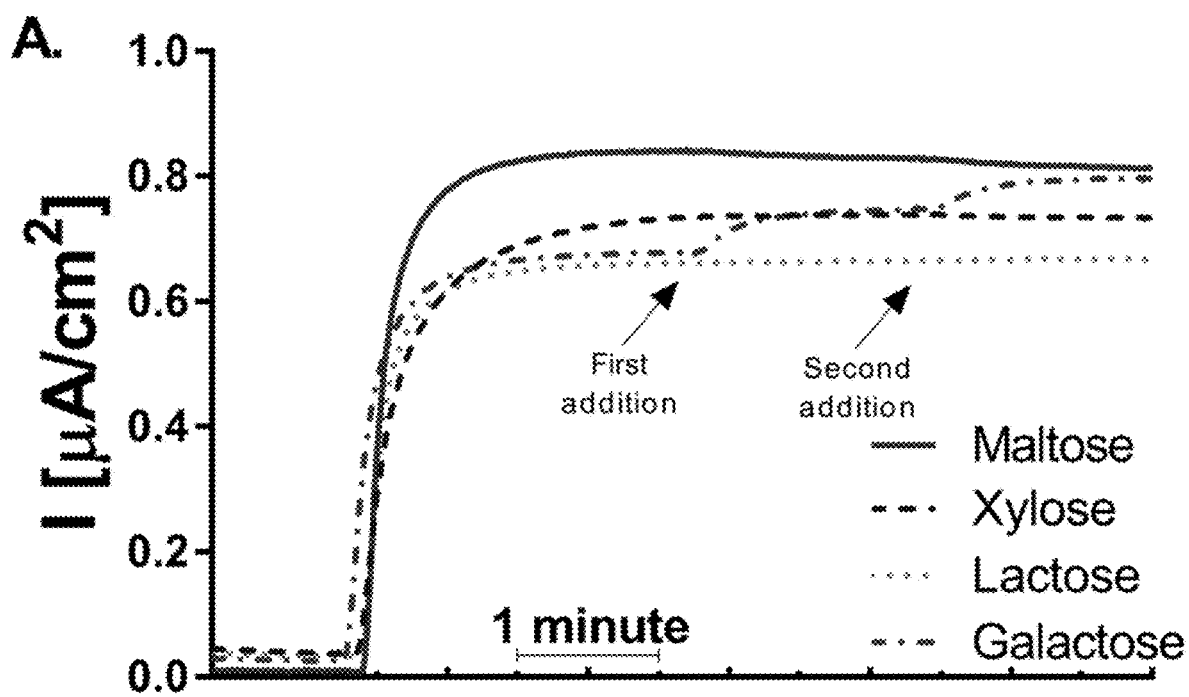
FIGS. 8A-8C are graphs showing GCE/FGM selectivity test that was performed by adding 3.6 mM glucose followed by two sequential additions of sugars in their relevant physiological concentration—1.67 and 3.3 mM galactose –.–), 0.3 and 0.6 mM lactose ( . . . ), 2.9 and 5.8 mM maltose (red -) and 1.67 and 3.3 mM xylose ( --- ) (FIG. 8A); other molecules interference was tested by adding 3.6 mM glucose followed by two additions of 0.17 mM ascorbic acid and 0.2 mM acetaminophen at an applied potential of 0.0 mV (FIG. 8B); and 300 mV vs. Ag/AgC (FIG. 8C).
Figure 8B:
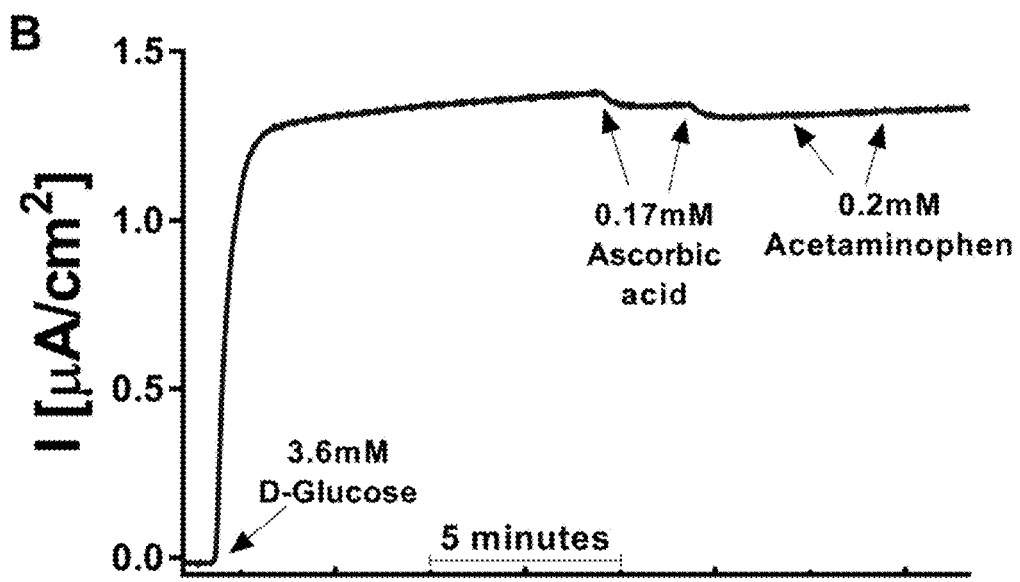
Figure 8C:
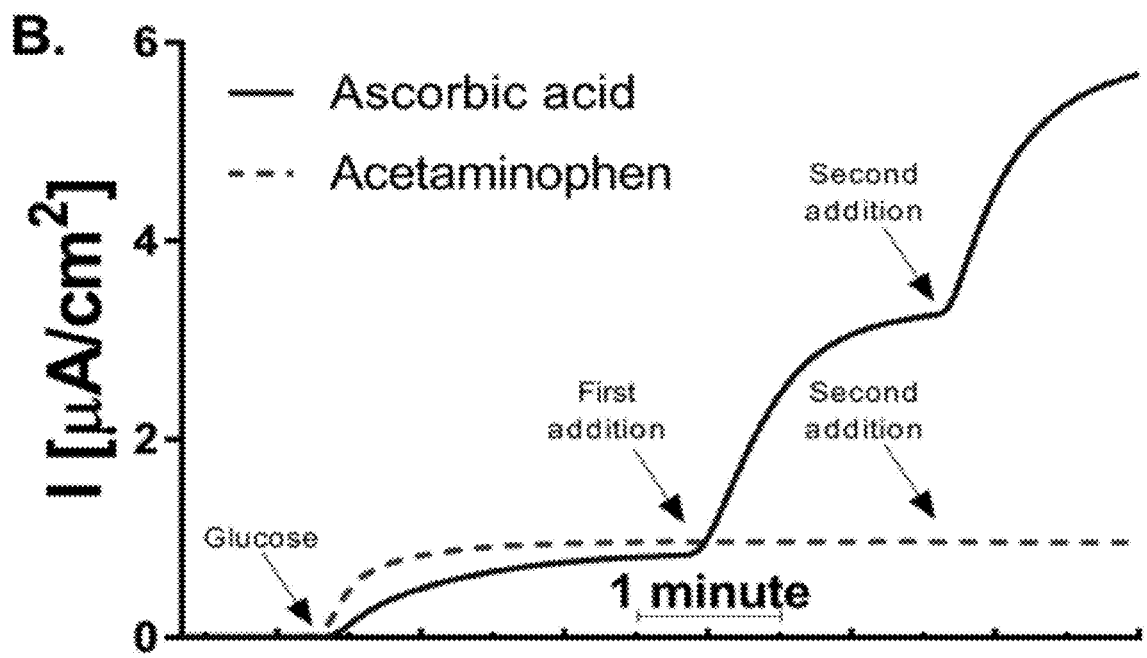

The interference of different sugars and molecules on glucose biosensing by GCE/FGM was measured using chronoamperometry (see selectivity FIGS. 8A-C). Measurements were performed in 0.15 M phosphate-citrate buffer pH=5.0 with the application of 0 mV vs. Ag/AgCl reference electrode. FGM selectivity was tested by adding 3.6 mM of glucose followed by two sequential additions of one of the different sugars or molecules in their relevant physiological concentrations. The sugars used for this test were D-galactose, lactose, D-maltose and D-xylose and the molecules were ascorbic acid and acetaminophen (all from Sigma-Aldrich, Rehovot, Israel). Selectivity test have revealed a small interference caused by galactose while other sugars did not interfere with the measurement. This result indicates high selectivity towards glucose and low/no reaction with other sugars that can be found in human blood samples, which is very important for biosensing accuracy. GCE\FGM showed low sensitivity to ascorbic acid and no sensitivity to acetaminophen.

The Biocatalytic Recombinant Protein

In the present study, a fusion enzyme was designed in a combination of a biocatalytic function from a redox enzyme domain that was fused to a natural minimal ET domain via a short polypeptide linker as shown in FIG. 1. As the catalytic domain, the a subunit of an FAD-GDH from *Burkholderia cepacia* was used. As a minimal ET unit, the c-type cytochrome domain MCR-2 from a MamP protein which originates from a magnetotactic bacteria magnetoovoid bacterium MO-127 was chosen. MamP is part of the magnetosome, a unique organelle that is found in magnetotactic bacteria that allows magneto taxis to occur in these bacteria. MCR-2 is one of the shortest natural c-type cytochromes known today (23 amino-acids long), thus can be used to achieve DET.

In order for FAD-GDH-MCD (FGM) fused enzyme to mature properly in the host cell, FAD-GDH α subunit should correctly fold. The Enzyme's γ subunit aids in the maturation of the a subunit and locates it in the periplasm. Within the bacterial periplasmatic environment, the maturation of c-type cytochromes (heme binding cytochromes) occurs with the help of a specific gene cluster called ccmA-H29. In that manner, the holo-enzyme is being transferred to the periplasm and there the MCD's maturation process occurs.

Figure 2A:
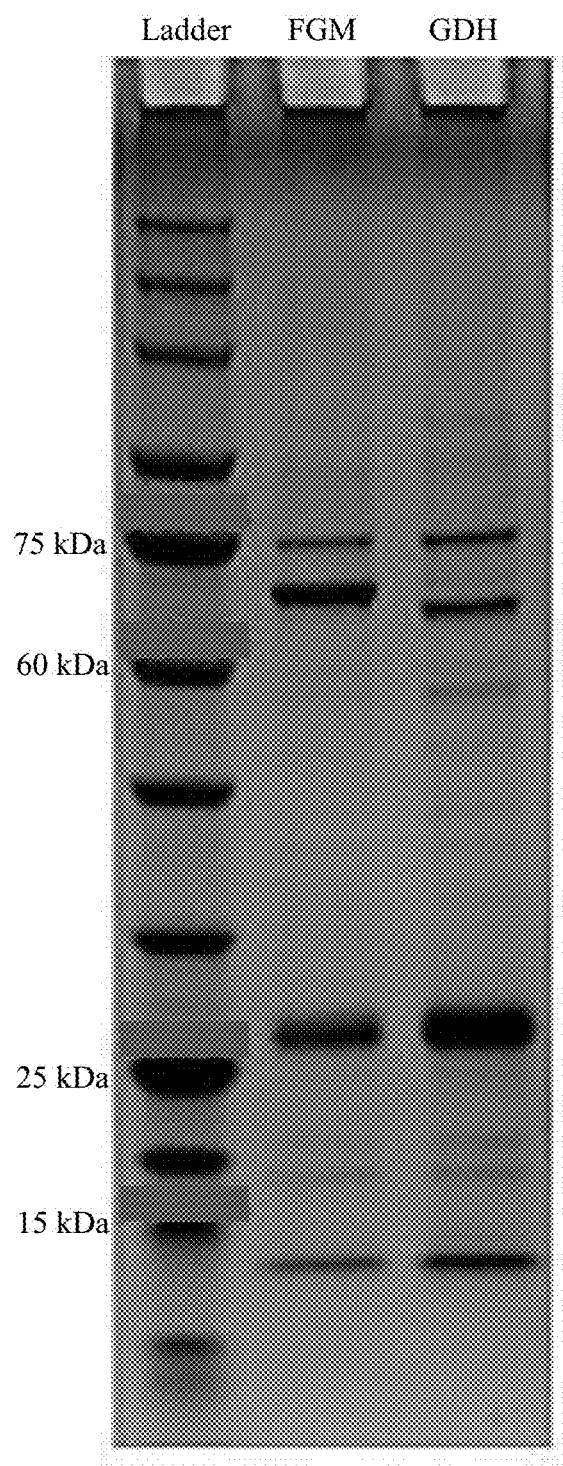
FIGS. 2A-2B present gel micrographs: Coomassie stained sodium dodecyl sulfate-polyacrylamide gel electrophoresis (SDS-PAGE) analysis of FGM and GDH elution fractions resulting from IMAC purification. FGM and GDH catalytic sub-units are shown between 60 to 75 kDa. Band at ca. 13 kDa in both lanes correlates to FAD-GDH γ subunit (FIG. 2A); and in-gel heme staining showing the presence of a heme molecule in FGM compared to its absence in GDH (FIG. 2B, left panel) and Anti 6×his-tag Western blot verifying the full-length protein expression.
Figure 2B:
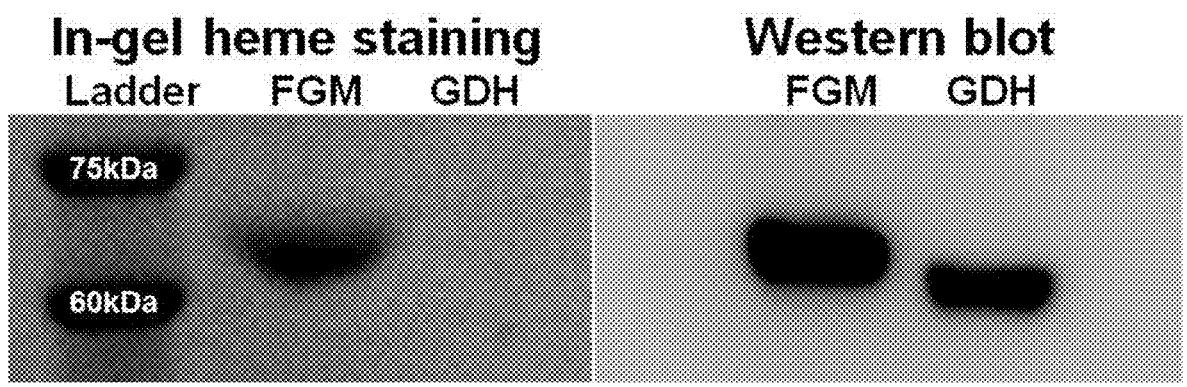

Fusion enzyme's engineered DNA sequence was cloned into pTrcHis6A2 expression vector and was transformed into *E. coli* BL21. FGM was overexpressed in the bacterial expression system and then purified by utilizing immobilized metal affinity chromatography (IMAC) purification system (FIG. 2A). In-gel heme staining was performed to verify the presence of the heme compared to GDH and Anti his-tag Western blot analysis was performed in order to verify the full-length enzyme's expression (FIG. 2B, right panel). As shown in FIG. 2B, both FGM and GDH enzymes were expressed and their respective bands appeared in the expected size—ca. 64 kDa and 62 kDa for FGM and GDH, respectively. In-gel heme staining revealed a band for FGM only, indicating the presence of a porphyrin containing iron bound to FGM.

Figure 3A:
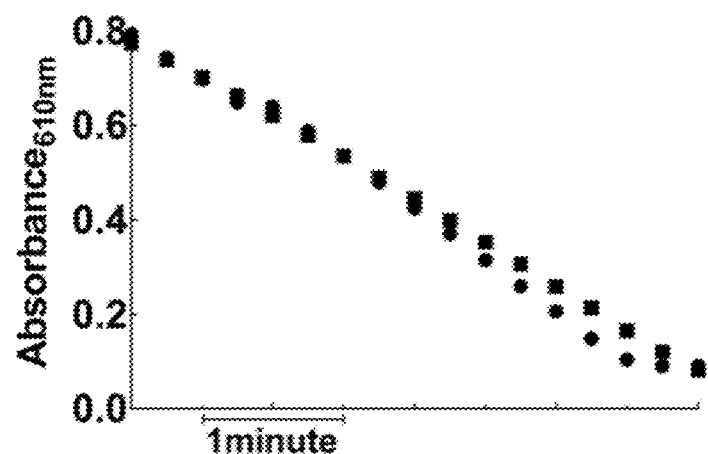
FIGS. 3A-3D are graphs showing: 2,6-dichloroindophenol (DCIP) reduction assay comparing the oxidation of D-glucose by both FGM (■) and GDH (●) (FIG. 3A) and Heme activity measurements verifying the presence of a porphyrin in FGM compared to GDH. Measurements were performed in 37° C., 50 mM Tris buffer, pH=7.0 (FIG. 3B); Peroxidase activity interference test; FGM was compared to Glucose oxidase (GOx) which is oxygen sensitive; No hydrogen peroxide was detected upon glucose oxidation by FGM while GOx, as a positive control, showed hydrogen peroxide production and its subsequent reduction by HRP is visible (FIG. 3C); and absorbance spectrum of FGM and GDH showing peak in absorbance at 408 nm for FGM and no peak for GDH (FIG. 3D).

FGM catalytic redox activity and heme peroxidase activity were measured biochemically and compared to GDH as shown in FIG. 3A. FGM has oxidized D-glucose as was measured by FAD-GDH activity assay in 50 mM Tris-base (pH 7.0), 0.6 mM 2,6-Dichloroindophenol (DCIP) and 0.6 mM phenazine methyl sulfate (PMS) in 37° C. Absorbance (lambda=610 nm) was monitored using a plate reader while the oxidized DCIP (blue color) was being reduced by FGM to its reduced form (colorless). FGM has also shown peroxidase activity, measured by heme activity assay in 1 mM 3,3'-Dimethoxybenzidine (DMB) and 1 mM of hydrogen peroxide. Absorbance in 455 nm was monitored while the DMB oxidation occurs by the MCD, resulted in an oxidized DMB (red color). Heme activity assay results indicate that FGM indeed binds a heme group while no heme molecules are bound by GDH.

Figure 3B:
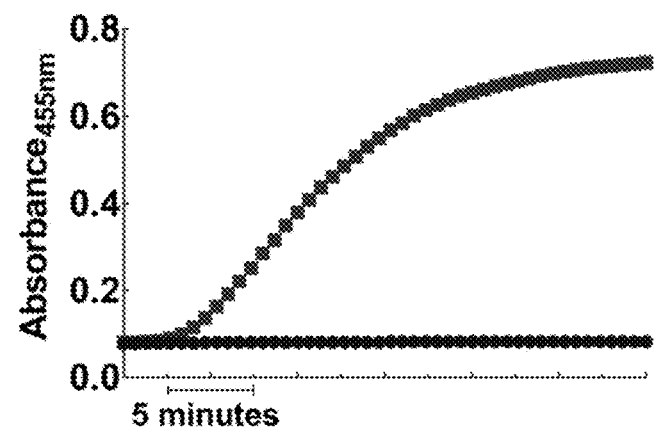
Figure 3C:
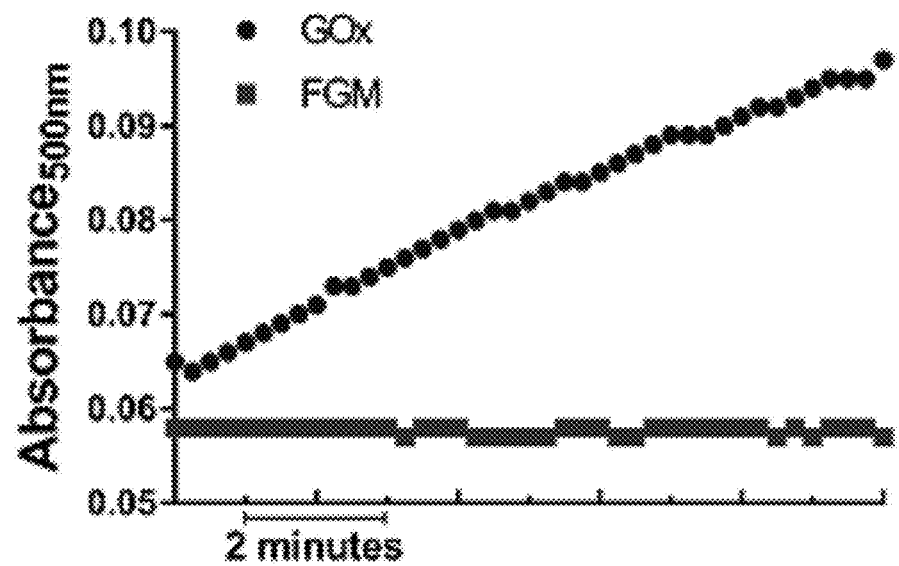
Figure 3D:
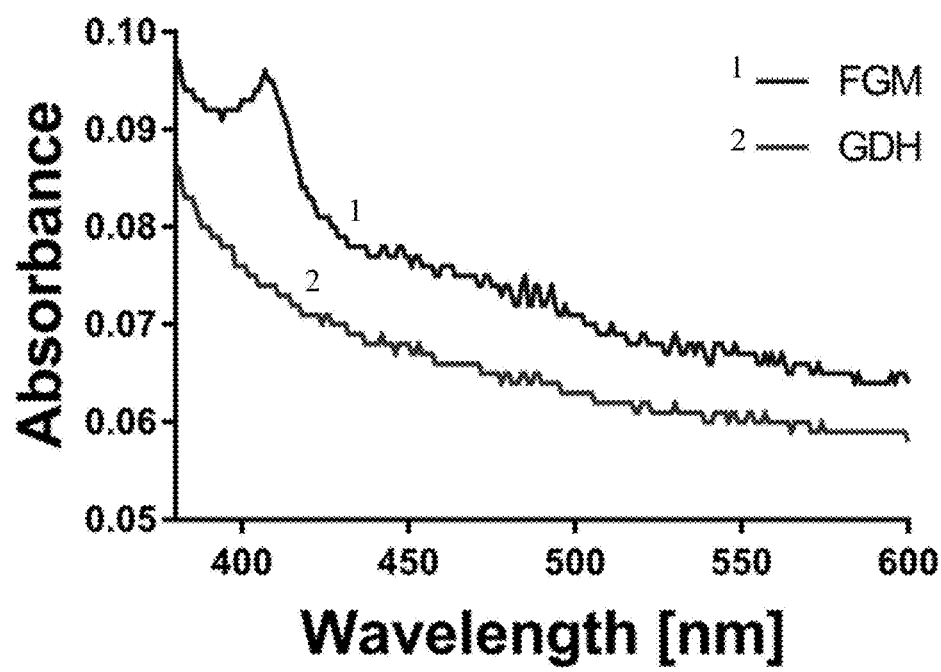

Absorbance measurements of protein sample spectrum revealed a peak in absorbance at 408 nm for FGM and no peak for GDH, indicating presence of heme c in FGM (FIG. 3B). 408 nm/A280 nm ratio was calculated to be 0.4 for FGM expressed in the presence of pEC86 plasmid, compared to 0.2 for FGM expressed in the absence of this plasmid, indicating more efficient heme maturation in the presence of the helper plasmid.

The apparent kinetic and thermodynamic parameters of FGM were calculated using FAD-GDH biochemical activity assay in 37° C. (Table 1). FGM and GDH concentrations were first determined spectrophotometrically using a standard Bradford assay. Michaelis-Menten curves were transformed to Lineweaver-Burk curves in order to determine the kinetic and thermodynamic parameters of the enzyme. One enzyme activity unit was defined as amount of enzyme oxidizing 1 µM of substrate per minute. The molar absorption coefficient of DCIP was calculated to be 4.7 $cm^{-1}mM^{-1}$.

By using the biochemical activity assay and DCIP molar absorption coefficient, FGM and GDH specific activity were calculated to be 16 mU.

Lineweaver-Burk plots (FIGS. 7A-B) were used to calculate kinetic and thermodynamic parameters of the enzyme. $K_M^{app}$ values were 157±5 µM and 174±9 µM for FGM and GDH, respectively, showing different affinity of the enzymes toward the substrate. GDH's $K_M^{app}$ value is lower than reported values but yet in the same order of magnitude of some. $K_M^{app}$ value was ca. 3 times higher for FGM compared to GDH, indicating faster oxidation of D-glucose by FGM. FGM also showed more than 3 times higher catalytic efficiency (k) compared to GDH (Table 1). Next, the electrochemical activity of the enzymes was measured to determine whether the addition of the minimal cytochrome domain improves enzyme-electrode ET.

Figure 5A:
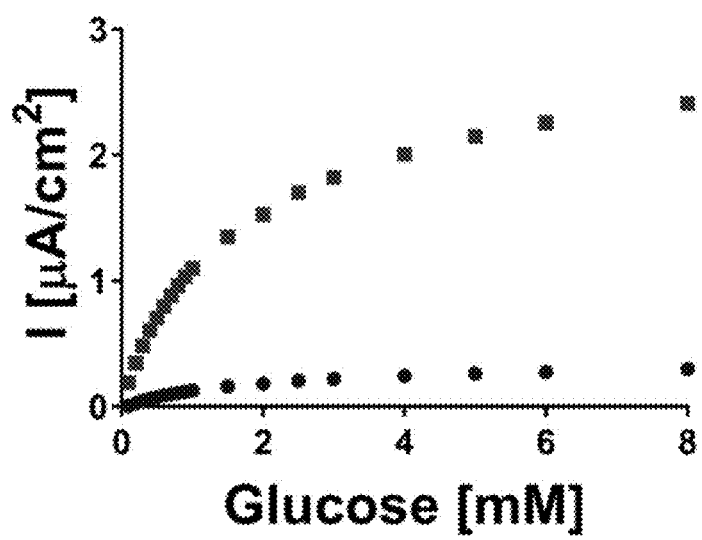
FIGS. 5A-5B present graphs showing steady state currents from chronoamperometry measurements of GCE/GDH (●) and GCE/FGM (■) using different glucose concentrations (FIG. 5A); and Lineweaver-Burk plots of electrochemical activity for both, FGM and GDH. Linear trend line equations were calculated to be y=123x+42.3 for GDH and y=10.1x+7.1 for FGM (FIG. 5B).
Figure 5B:
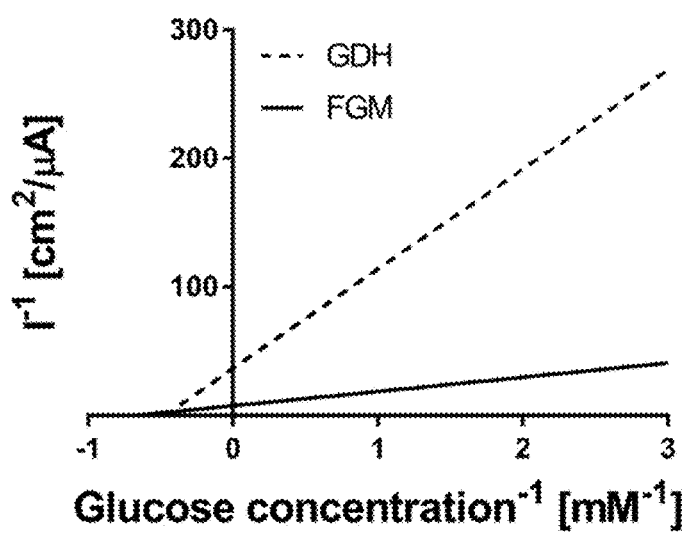

Chronoamperometric measurements (FIG. 7C) were performed to determine the apparent kinetic parameters of FGM compared to GDH. Using a standard 3 electrode electrochemical cell, the current was measured vs. successive glucose additions. A potential of 0V was applied during the measurements. The current for each glucose concentration was determined and is presented in FIG. 5A. As described above, using the linear part of the transient curves and Linewaver-Burk transformation—the electrochemical kinetic constants were calculated (FIG. 5B).

TABLE 1

Apparent biochemical kinetic parameters of FGM and GDH

|  | $k_{cat}^{app}$ (s$^{-1}$) | $K_M^{app}$ (µM) | $k_{cat}^{app}/K_M^{app}$ (s$^{-1}$·mM$^{-1}$) |
|---|---|---|---|
| GDH | 1.7 ± 0.1 | 174 ± 9 | 9.6 ± 0 |
| FGM | 5.2 ± 0.1 | 157 ± 5 | 33 ± 0 |

For the electrochemical measurements, a standard 3 electrode electrochemical cell with 0.9 mm graphite rod as the auxiliary electrode were used, 3M KCl saturated Ag/AgCl reference electrode and 3 mm diameter glassy carbon electrode (GCE) as the working electrode. 10 µL of ca. 30 µg/mL FGM or GDH enzyme solution were dropped on the GCE surface and dried in 4° C. overnight. The electrodes surface was then covered with 12-14 kDa dialysis membrane tightened to the surface with an O-ring to keep the enzyme close to the electrode surface during measurements and to avoid enzyme diffusion to the surrounding buffer. Cyclic voltammetry (CV) measurements were performed to compare the enzyme-electrode communication of FGM to that of GDH.

Optimal pH value for electrochemical measurements was tested by measuring the catalytic current in pH values of 3.6-7.0 and found to be 5.0.

Figure 4A:
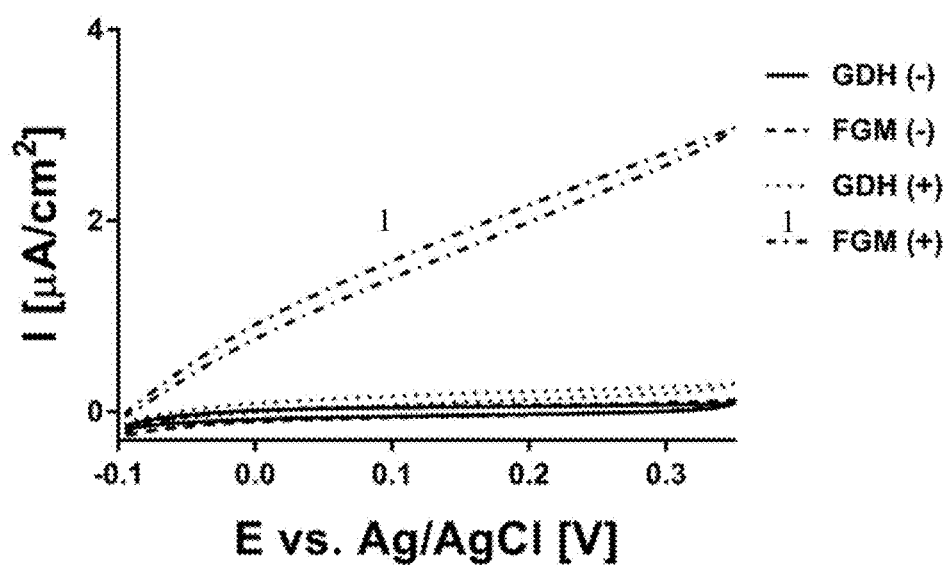
FIGS. 4A-4C present graphs showing cyclic voltammograms of GCE/GDH and GCE/FGM with (+) and without (−) 5 mM glucose. The measurements were performed in 150 mM phosphate-citrate buffer, pH=5.0 at room temperature vs Ag/AgCl as a reference electrode at a scan rate of 5 mV s$^{-1}$ (FIG. 4A) and 100 mV s$^{-1}$ (FIG. 4B), and square-wave voltammetry (SWV)s of GCE/GDH and GCE/FGM. Measurements performed in 150 mM phosphate-citrate buffer, pH=5.0 vs Ag/AgCl reference electrode with 5 mV steps, amplitude 10 mV and a frequency 5 Hz (FIG. 4C). Background GCE current subtracted from the signal (GCE: glassy carbon electrode).
Figure 4B:
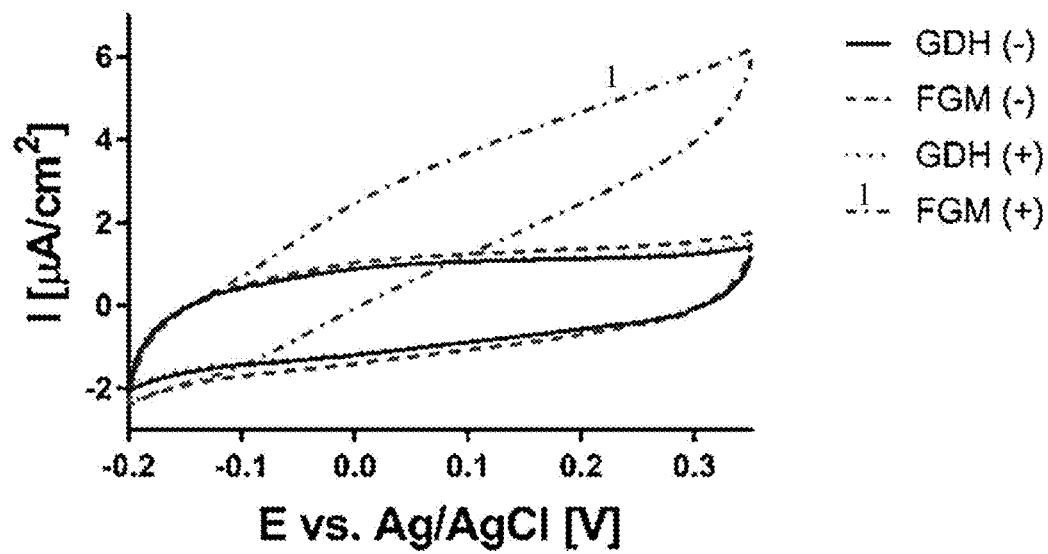

Measurements were performed in phosphate-citrate buffer pH=5.0 at room temperature and a scan rate of 5 mV/sec for both enzymes with and without the addition of 5 mM glucose. It can be seen in FIGS. 4A-B that the CVs of both enzymes before the addition of glucose are almost identical. No clear anodic or cathodic peaks were identified for both enzymes. After the addition of glucose to a final concentration of 5 mM, FGM has demonstrated 10 times higher electrocatalytic current compared to that of GDH with an onset potential of ca. −100 mV for both enzymes (indicating no apparent shift in potentials due to the fusion of MCD). That difference in the ET efficiency is probably due to the addition of the minimal cytochrome domain that mediates the ET from the buried FAD co-factor to GCE.

Figure 4C:
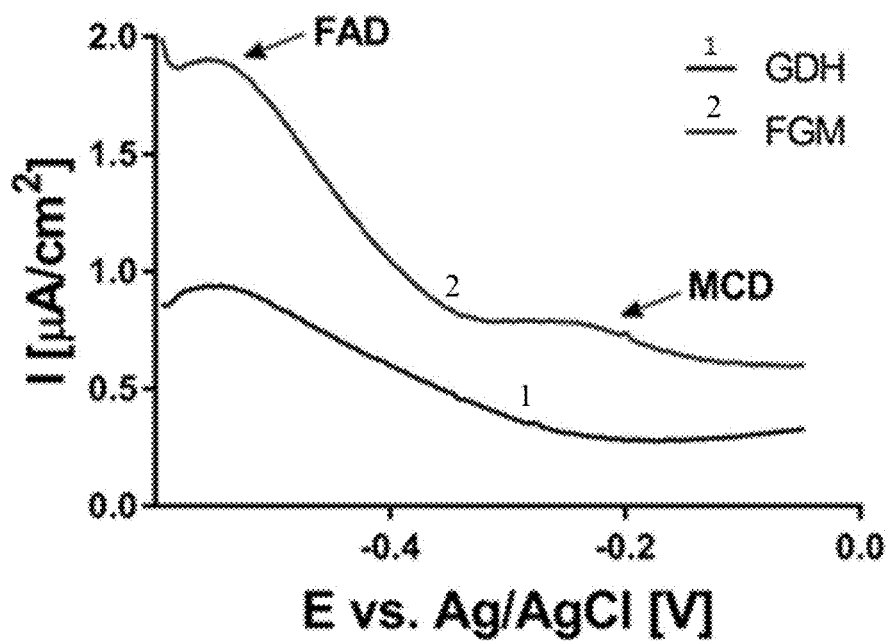

After the addition of glucose to a final concentration of 5 mM, FGM demonstrated a higher electrocatalytic current compared to that of GDH with an onset potential of ca. (−) 150 mV. The fact that no catalytic current was observed at this high scan rate using GDH, but a significant catalytic current evolved using FGM, is an indication of fast ET rates of FGM. That observed ET efficiency is probably due to addition of the minimal cytochrome domain that mediates ET from the buried FAD cofactor to GCE. To identify a peak originating from the MCD domain, square-wave voltammetry (SWV) was performed. As shown in FIG. 4C, the voltammogram of an electrode with FGM revealed a peak around (−) 230 mV, whereas GDH had no observable peak at this potential.

As shown in Table 2, the electrochemical $K_M^{app}$ is 2.84±0.57 mM for GDH and 1.40±0.27 mM for FGM, indicating no significant difference in the affinity towards glucose. The $i_{max}$ value is one order of magnitude higher for FGM compared to GDH −2.04±0.45 µA·cm$^{-2}$ and 0.4±0.17 µA·cm$^{-2}$, respectively. The difference in the $i_{max}$ value is indicative that the DET efficiency is different between the two enzymes where FGM shows five to seven times higher current then GDH for the same glucose concentrations.

TABLE 2

Apparent electrochemical kinetic and thermodynamic parameters of FGM and GDH

|  | $K_M^{app}$ (mM) | $i_{max}$ (µA·cm$^{-2}$) |
|---|---|---|
| GDH | 2.8 ± 0.6 | 0.4 ± 0.2 |
| FGM | 1.4 ± 0.3 | 2.0 ± 0.5 |

Figure 9:
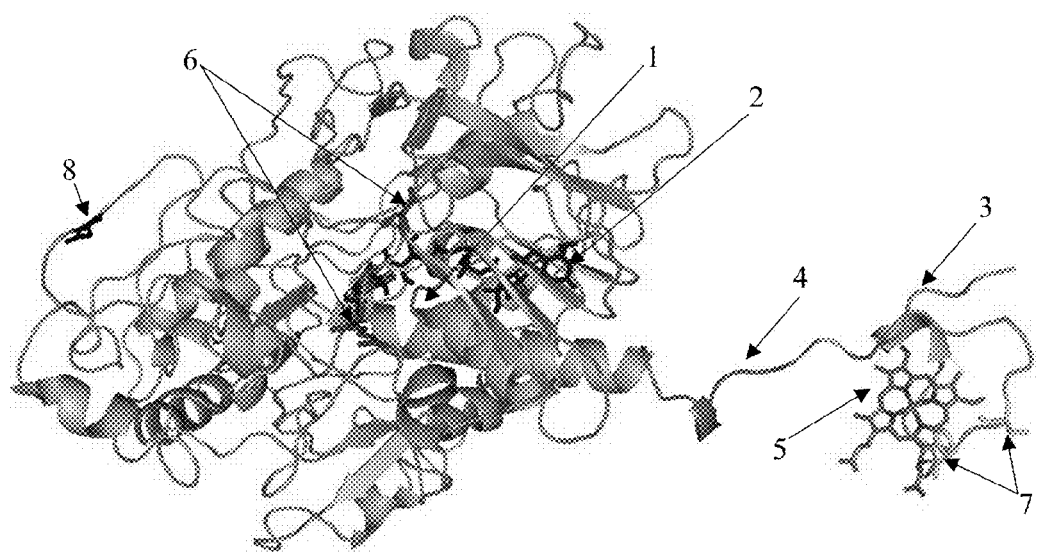
FIG. 9 presents 3D model of FAD-GDH from $B.$ $cepacia$ (green) is presented with its FAD binding motif (orange, "1") and the FAD co-factor (blue, "2"). MCD model (cyan, "3") and the linker (grey, "4") were cut from MamP known 3D structure and include the heme molecule (pink, "5"). The fusion shown in this figure was manually generated using PyMOL software. ncAA possible incorporation sites were colored—proximity to FAD (red, "6"), to MCD (yellow, "7"), distant from both FAD and MCD (black, "8").

*Burkholderia Cepacia* is considered a good candidate for biosensing applications because of its stability in high temperatures and insensitivity to oxygen. By adding a minimal cytochrome domain to FAD-GDH c-terminus an improved DET was provided, showing higher catalytic currents compered to GDH with almost the same affinity to the substrate. When tested electrochemically with 0V induced potential vs Ag/AgCl, FGM showed much higher currents for the same substrate concentrations compared to GDH, which makes it more accurate for glucose biosensing with improved sensitivity than previously reported for GDH.
Non-Canonical Amino Acids (ncAAs) Incorporation into FGM for Site-Specific Wiring to an Electrode:
FGM Electron Transfer Machineries Investigation To incorporate non-canonical amino acids (ncAAs) into FGM, a few constructs containing the amber (TAG) mutation on pTrcHis6A2-FGM plasmid were prepared using standard site-directed mutagenesis PCR protocol. The mutations were chosen with a proximity to the protein different domains—FAD binding domain, MCD and one site that is distant from either FAD domain or MCD. For proximity to FAD binding domain, two sites were found to be possible for ncAA incorporation—R42X and S247X (FIG. 9—red), both ca. 11 Å from FAD binding domain. For proximity to MCD, T558X and P560X (yellow) are possible sites for incorporation, with 10 and 7 Å from MCD, respectively. D395X (black) was found to be far from both FAD and MCD as it is about 37 Å from FAD and 83 Å from MCD.

Mutated plasmids were transformed into super competent *E. coli* DH5a cells and were plated on selective LB-agar plates. Bacterial colonies were isolated and plasmids were purified using miniprep kit followed by sequencing.

Non-Canonical Amino Acids (ncAA) Incorporation into FGM

Plasmids, with amber codon-containing FGM mutants sequences were co-transformed to E. coli BL21 strain containing the pEVOL plasmid expressing Pyrrolysyl orthogonal translation system to incorporate Propargyl-lysine (PrK) into the protein sequence. PrK containing protein was expressed in 20 mL auto-induction medium (AIM) in the presence of 1 mM PrK, lysed using Bugbuster lysis solution and was isolated utilizing IMAC purification method. PrK is an example to a clickable nCAA, all clickable biorthogonal chemical handles can be considered for the site-specific wiring of this enzyme.

Pyrene-Azide Linkers for Enzyme Wiring to Electrode

Figure 10A:
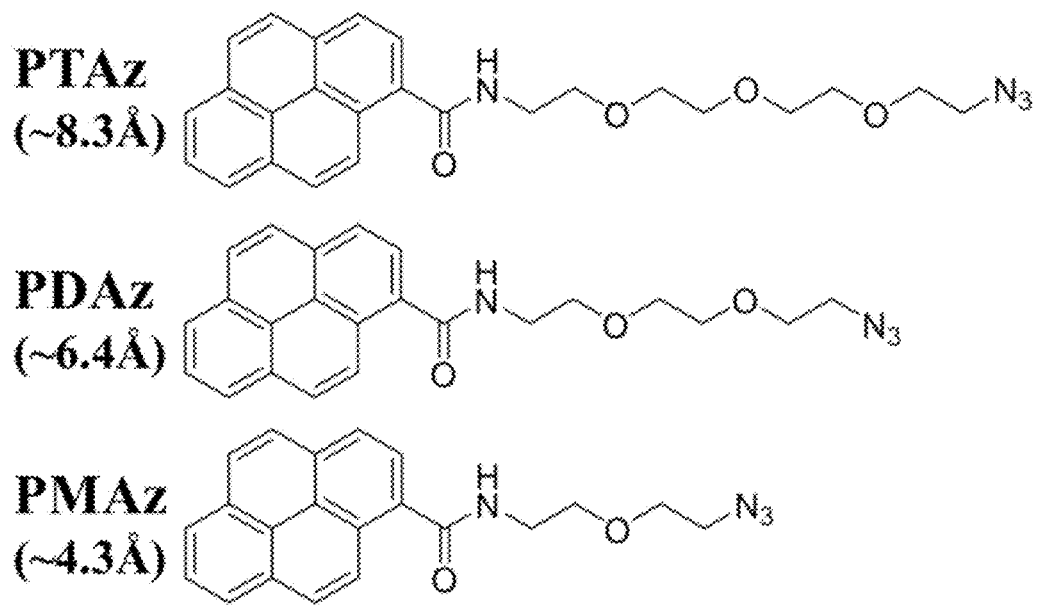
FIGS. 10A-10B present non-limiting pyrene-azide linker structures with different lengths (FIG. 10A) and 5-etramethylrhodamine (TAMRA)-azide chemical structure (FIG. 10B).

In order to wire FGM with site-specifically incorporated PrK to an electrode, a synthetic linker was used. The synthetic linker contained a pyrene group in one pole and an azide group at the other. The two groups were connected by a tri-ethylene oxide, di-ethylene oxide or mono-ethylene oxide, to get three different lengths of 8.3, 6.4 and 4.3 Å, respectively. The pyrene group is a polycyclic aromatic hydrocarbon consisting of four fused benzene rings, results in a flat aromatic system. Due to overlapping of it-bonds between aromatic side chains, the pyrene group can be attached to glassy carbon electrodes surface through π-π stacking. The azide group was used to attach the alkyne group of PrK using "click" chemistry. Exemplary pyrene-azide linker structures with different lengths are presented in FIGS. 10A-B.

Click Reaction:

Copper-catalyzed azide-alkyne cycloaddition (CuAAC) reaction is based on the formation of 1,4-disubstituted 1,2,3-triazoles between a terminal alkyne and an aliphatic azide in the presence of copper. The reaction is a facile, selective, high yielding with mild conditions and with few or no byproducts. It can be performed in room-temperature, what makes it relevant for use in proteins. CuAAC was used to link FGM to a pyrene-azide synthetic linker. Click reaction mix contained tris-KCl buffer (pH=8.2), pyrene-azide linker, $Cu^+$, Tris(3-hydroxypropyltriazolylmethyl)amine (THPTA), FGM with incorporated PrK and sodium-ascorbate (Na-Asc). Reaction mix was incubated in RT for 30-60 min with moderate mixing, centrifuged for 10 min, and the supernatant was collected for further examinations.

ncAA Incorporation Validation

Figure 10B:
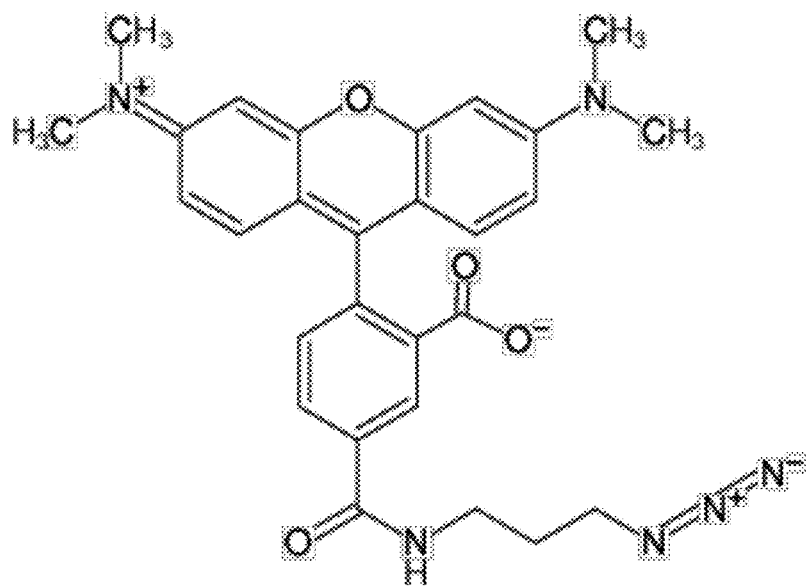

TAMRA-azide is an azide-linked reporter tag that can be used for visualization of alkyne containing proteins (see FIG. 10B). To validate incorporation of PrK into FGM sequence, purified FGM was clicked with the florescent marker TAMRA-azide. Clicked protein sample was loaded on SDS-PAGE and the protein gel was checked for florescence using LAS4000 camera. In addition, anti 6×His-tag antibodies will be used for Western blot analysis. MS-MS analysis was performed on isolated protein to give another validation for PrK incorporation.

Enzyme Site-Specific Wiring to GCE

Ten μL of pyrene-azide clicked to PrK containing FGM was dropped on clean GCE and incubate in RT for 15 min. The pyrene groups from the linker adhere to GCE surface through π-π stacking. GCE was washed using DW to avoid unbound protein showing signal in electrochemical measurements.

Relevant FGM DNA sequences (all sequences are of the FAD-GDH α-subunit+MCD, without the γ-subunit): R42X (SEQ ID NO: 14); S247X (SEQ ID NO: 15); D395X (SEQ ID NO: 16); T558X (SEQ ID NO: 17); P560X (SEQ ID NO: 18).

Relevant FGM protein sequences (all sequences are of the FAD-GDH α-subunit+MCD, without the γ-subunit): R42X (SEQ ID NO: 19); S247X (SEQ ID NO: 20); D395X (SEQ ID NO: 21); T558X (SEQ ID NO: 22); P560X (SEQ ID NO: 23).

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A recombinant protein, comprising: (a) alpha subunit of a flavin adenine dinucleotide-glucose dehydrogenase (FAD-GDH); and (b) a minimal c-type cytochrome peptide.

2. The recombinant protein of claim 1, wherein said alpha subunit of an FAD-GDH is a *Burkholderia cepacian* alpha subunit of an FAD-GDH.

3. The recombinant protein of claim 1, wherein said alpha subunit of said FAD-GDH comprises the amino acid sequence set forth in SEQ ID NO: 8.

4. The recombinant protein of claim 1, wherein said minimal c-type cytochrome peptide is a cytochrome second magnetochrome domain (MCR-2) from magnetosome protein MamP.

5. The recombinant protein of claim 1, comprising the amino acid sequence set forth in SED ID NO: 9.

6. The recombinant protein of claim 1, further being bound to a porphyrin comprising a metal.

7. The recombinant protein of claim 6, wherein said metal is a trivalent metal or a divalent metal.

8. The recombinant protein of claim 1, further being bound to a compound of formula I:

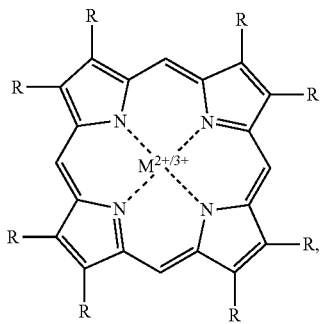

wherein said R is any electron donor, said compound of formula I is bound to a metal.

9. The recombinant protein of claim 1, further comprising a substitution of at least one amino acid residue of said alpha subunit of said FAD-GDH, said minimal c-type cytochrome peptide, or both, with a non-canonical amino acid residue.

10. The recombinant protein of claim 9, being coupled to an electrode via said non-canonical amino acid (ncAA) residue.

11. A composition comprising the recombinant protein of claim 1 and the gamma subunit of an FAD-GDH.

12. A DNA molecule comprising a nucleotide sequence encoding the recombinant protein of claim 1.

13. The DNA molecule of claim 12, comprising the nucleic acid sequence set forth in SEQ ID NO: 5.

14. An expression vector comprising the DNA molecule of claim 12.

15. A cell comprising the DNA molecule of claim 12.

16. A method for transferring an electron to an electrode, comprising coupling the recombinant protein of claim 9 to an electrode, wherein the recombinant protein is further bound to a porphyrin comprising a metal, thereby transferring an electron to said electrode.

* * * * *

SEQUENCE LISTING

```
<160> NUMBER OF SEQ ID NOS: 29

<210> SEQ ID NO 1
<211> LENGTH: 1617
<212> TYPE: DNA
<213> ORGANISM: Artificial
<220> FEATURE:
<223> OTHER INFORMATION: Synthetic

<400> SEQUENCE: 1
atggcggata cggatcccca gaaagcggac gtggtcgtgg ttggatccgg cgtggcaggc      60
gcaatcgtgg ctcatcaact ggcaatggca ggtaaaagcg tgatcctgct ggaagctggt     120
ccgcgtatgc cgcgttggga aattgttgaa cgtttccgca atcaagtcga taaaaccgac     180
tttatggcac cgtatccgag cagcgcatgg gcaccgcatc cggaatatgg tccgccgaat     240
gattacctga tcctgaaagg cgaacacaaa tttaactcac agtacattcg tgcagtgggc     300
ggcaccacgt ggcattgggc agcctcggca tggcgcttca tcccgaacga tttttaaaatg     360 aaaaccgtgt atggcgttgg tcgtgactgg ccgattcagt acgatgacat cgaacattat     420
```

```
taccaacgcg cggaagaaga actgggcgtg tggggtccgg gcccggaaga agacctgtat    480
tcaccgcgta aagaaccgta cccgatgccg ccgctgccgc tgagtttcaa tgaacaaacc    540
attaaatccg ctctgaacgg ctatgatccg aaatttcacg tggttacgga accggtggcc    600
cgtaattcgc gcccgtacga cggtcgcccg acctgctgtg caacaataa ctgcatgccg     660 atttgtccga tcggtgcaat gtataacggc atcgtccatg tggaaaaagc tgaacaggca    720
ggtgctaaac tgattgatag tgcggtcgtg tacaaactgg aaacgggccc ggacaaacgt    780
attaccgcag ctgtttataa agataaaacg ggtgcggacc atcgcgtcga aggcaaatac    840
ttcgtgattg cggccaatgg tatcgaaacc ccgaaaattc tgctgatgag cgcgaaccgt    900
gattttccga atggtgtggc caacagttcc gatatggttg ccgcaatct gatggaccat     960 ccgggcaccg gcgtgagctt ttatgcaaac gaaaaactgt ggccgggtcg tggtccgcag   1020
gaaatgacct ctctgatcgg tttccgtgat ggcccgtttc gcgcgaatga agcagcgaag   1080
aaaattcatc tgtcaaatat gtcgcgtatc aaccaggaaa cccaaaaaat ctttaaaggc   1140
ggtaaactga tgaaaccgga agaactggat gcgcagatcc gtgaccgcag tgcccgcttt   1200
gttcaattcg attgctttca cgaaatcctg ccgcagccgg aaaatcgtat tgtcccgtcc   1260
aaaaccgcaa cggacgcagt gggtattccg cgtccggaaa ttacgtatgc gatcgatgac   1320
tacgtcaaac gtggcgcagt gcatacgcgc gaagtttatg ctaccgcggc caaagtgctg   1380
ggcggcaccg aagtggtctt caacgatgaa tttgcgccga ataaccacat caccggtgcc   1440
acgattatgg gcgcggatgc ccgtgactca gtggttgata agactgtcg cgccttcgat    1500 catccgaacc tgtttattag cagcagcagc accatgccga cggttggcac cgttaacgtc   1560
accctgacga ttgcagctct ggcactgcgt atgtctgata cgctgaaaaa agaagtc      1617
```

<210> SEQ ID NO 2
<211> LENGTH: 510
<212> TYPE: DNA
<213> ORGANISM: Artificial
<220> FEATURE:
<223> OTHER INFORMATION: Synthetic

<400> SEQUENCE: 2

```
atggctcaca atgacaacac cccgcactcc cgccgtaccg gcgatgcggc cgtgaccggt     60
attacgcgtc gccagtggct gcaaggcgcg ctggccctga ccgcagctgg cctgacgggt    120
tccctggccc tgcgcgcact ggctgatgat ccgggcaccg caccgctgga tacctttatg    180
acgctgagcg aagctctgac gggcaaaaaa ggtctgtctc gtgttctggg ccagcgtttt    240
ctgcaagcgc tgcaaaaagg ttcattcaaa accgcggatt cgctgccgca gctggcgggc    300
gccctggcaa gcggttctct gaacccggac caagaagctc tggcgctgaa atcctggaa    360 gcatggtatc tgggcattgt tgataatgtg gttatcacct acgaagaagc cctgatgttt    420
agtgtcgtgt ccgacacgct ggtcattccg agctattgcc cgaacaaacc gggtttctgg    480
gccgaaaaac cgatcgaacg tcaggcataa                                     510
```

<210> SEQ ID NO 3
<211> LENGTH: 69
<212> TYPE: DNA
<213> ORGANISM: Artificial
<220> FEATURE:
<223> OTHER INFORMATION: Synthetic

<400> SEQUENCE: 3

| | |
|---|---|
| attcgtgcag gtgctaccat gccgcatcgt gatcgtggtc cgtgcggtgc atgtcacgct | 60 |
| attatccag | 69 |

<210> SEQ ID NO 4
<211> LENGTH: 39
<212> TYPE: DNA
<213> ORGANISM: Artificial
<220> FEATURE:
<223> OTHER INFORMATION: Synthetic

<400> SEQUENCE: 4

| | |
|---|---|
| gaattcggtt ctggttatgg ctctggtccg ccgggtccg | 39 |

<210> SEQ ID NO 5
<211> LENGTH: 2191
<212> TYPE: DNA
<213> ORGANISM: Artificial
<220> FEATURE:
<223> OTHER INFORMATION: Synthetic

<400> SEQUENCE: 5

| | |
|---|---|
| ctcacaatga caacaccccg cactcccgcc gtaccggcga tgcggccgtg accggtatta | 60 |
| cgcgtcgcca gtggctgcaa ggcgcgctgg ccctgaccgc agctggcctg acgggttccc | 120 |
| tggccctgcg cgcactggct gatgatccgg gcaccgcacc gctggatacc tttatgacgc | 180 |
| tgagcgaagc tctgacgggc aaaaaaggtc tgtctcgtgt tctgggccag cgttttctgc | 240 |
| aagcgctgca aaaaggttca ttcaaaaccg cggattcgct gccgcagctg gcgggcgccc | 300 |
| tggcaagcgg ttctctgaac ccggaccaag aagctctggc gctgaaaatc ctggaagcat | 360 |
| ggtatctggg cattgttgat aatgtggtta tcacctacga agaagccctg atgtttagtg | 420 |
| tcgtgtccga cacgctggtc attccgagct attgcccgaa caaacggggt ttctgggccg | 480 |
| aaaaaccgat cgaacgtcag gcataatggc ggatacggat acccagaaag cggacgtggt | 540 |
| cgtggttgga tccggcgtgg caggcgcaat cgtggctcat caactggcaa tggcaggtaa | 600 |
| aagcgtgatc ctgctggaag ctggtccgcg tatgccgcgt tgggaaattg ttgaacgttt | 660 |
| ccgcaatcaa gtcgataaaa ccgactttat ggcaccgtat ccgagcagcg catgggcacc | 720 |
| gcatccggaa tatggtccgc gaatgattac cctgatcctg aaaggcgaac acaaatttaa | 780 |
| ctcacagtac attcgtgcag tgggcggcac acgtgtgcat tgggcagcct cggcatggcg | 840 |
| cttcatcccg aacgatttta aaatgaaaac cgtgtatggc gttggtcgtg actggccgat | 900 |
| tcagtacgat gacatcgaac attattacca acgcgcggaa gagaactggg cgtgtggggg | 960 |
| tccgggcccg gaagaagacc tgtattcacc gcgtaaagaa ccgtacccga tgccgccgct | 1020 |
| gccgctgagt ttcaatgaac aaaccattaa atccgctctg aacggctatg atccgaaatt | 1080 |
| tcacgtggtt acggaaccgg tggcccgtaa ttcgcgcccg tacgacggtc gcccgacctg | 1140 |
| ctgtggcaac aataactgca tgccgatttg tccgatcggt gcaatgtata acggcatcgt | 1200 |
| ccatgtggaa aaagctgaac aggcaggtgc taaactgatt gatagtgcgg tcgtgtacaa | 1260 |
| actggaaacg ggcccggaca aacgtattac cgcagctgtt tataaagata aacgggtgc | 1320 |
| ggaccatcgc gtcgaaggca atacttcgt gattgcggcc aatggtatcg aaaccccgaa | 1380 |
| aattctgctg atgagcgcga accgtgattt tccgaatggt gtggccaaca gttccgatat | 1440 |
| ggttggccgc aatctgatgg accatccggg caccggcgtg agcttttatg caaacgaaaa | 1500 |
| actgtggccg ggtcgtggtc cgcaggaaat gacctctctg atcggtttcc gtgatggccc | 1560 |
| gtttcgcgcg aatgaagcag cgaagaaaat tcatctgtca aatatgtcgc gtatcaacca | 1620 |

| | |
|---|---|
| ggaaacccaa aaaatcttta aaggcggtaa actgatgaaa ccggaagaac tggatgcgca | 1680 |
| gatccgtgac cgcagtgccc gctttgttca attcgattgc tttcacgaaa tcctgccgca | 1740 |
| gccggaaaat cgtattgtcc cgtccaaaac cgcaacggac gcagtgggta ttccgcgtcc | 1800 |
| ggaaattacg tatgcgatcg atgactacgt caaacgtggc gcagtgcata cgcgcgaagt | 1860 |
| ttatgctacc gcggccaaag tgctgggcgg caccgaagtg gtcttcaacg atgaatttgc | 1920 |
| gccgaataac cacatcaccg gtgccacgat tatgggcgcg gatgcccgtg actcagtggt | 1980 |
| tgataaagac tgtcgcgcct tcgatcatcc gaacctgttt attagcagca gcagcaccat | 2040 |
| gccgacggtt ggcaccgtta acgtcaccct gacgattgca gctctggcac tgcgtatgtc | 2100 |
| tgatacgctg aaaaaagaag tcattcgtgc aggtgctacc atgccgcatc gtgatcgtgg | 2160 |
| tccgtgcggt gcatgtcacg ctattatcca g | 2191 |

<210> SEQ ID NO 6
<211> LENGTH: 2230
<212> TYPE: DNA
<213> ORGANISM: Artificial
<220> FEATURE:
<223> OTHER INFORMATION: Synthetic

<400> SEQUENCE: 6

| | |
|---|---|
| ctcacaatga caacaccccg cactcccgcc gtaccggcga tgcggccgtg accggtatta | 60 |
| cgcgtcgcca gtggctgcaa ggcgcgctgg ccctgaccgc agctggcctg acgggttccc | 120 |
| tggccctgcg cgcactggct gatgatccgg gcaccgcacc gctggatacc tttatgacgc | 180 |
| tgagcgaagc tctgacgggc aaaaaaggtc tgtctcgtgt tctgggccag cgttttctgc | 240 |
| aagcgctgca aaaggttca ttcaaaaccg cggattcgct gccgcagctg gcgggcgccc | 300 |
| tggcaagcgg ttctctgaac ccggaccaag aagctctggc gctgaaaatc tggaagcat | 360 |
| ggtatctggg cattgttgat aatgtggtta tcacctacga agaagccctg atgtttagtg | 420 |
| tcgtgtccga cacgctggtc attccgagct attgcccgaa caaaccgggt ttctgggccg | 480 |
| aaaaaccgat cgaacgtcag gcataatggc ggatacggat acccagaaag cggacgtggt | 540 |
| cgtggttgga tccggcgtgg caggcgcaat cgtggctcat caactggcaa tggcaggtaa | 600 |
| aagcgtgatc ctgctggaag ctggtccgcg tatgccgcgt tgggaaattg ttgaacgttt | 660 |
| ccgcaatcaa gtcgataaaa ccgactttat ggcaccgtat ccgagcagcg catgggcacc | 720 |
| gcatccggaa tatggtccgc cgaatgatta cctgatcctg aaaggcgaac acaaatttaa | 780 |
| ctcacagtac attcgtgcag tgggcggcac cacgtgcat tgggcagcct cggcatggcg | 840 |
| cttcatcccg aacgatttta aaatgaaaac cgtgtatggc gttggtcgtg actggccgat | 900 |
| tcagtacgat gacatcgaac attattacca acgcgcggaa gaagaactgg gcgtgtgggg | 960 |
| tccgggcccg gaagaagacc tgtattcacc gcgtaaagaa ccgtacccga tgccgccgct | 1020 |
| gccgctgagt tcaatgaac aaaccattaa atccgctctg aacggctatg atccgaaatt | 1080 |
| tcacgtggtt acggaaccgg tggcccgtaa ttcgcgcccg tacgacggtc gcccgacctg | 1140 |
| ctgtggcaac aataactgca tgccgatttg tccgatcgt gcaatgtata cggcatcgt | 1200 |
| ccatgtggaa aaagctgaac aggcaggtgc taaactgatt gatagtgcgg tcgtgtacaa | 1260 |
| actggaaacg ggcccggaca acgtattac cgcagctgtt tataaagata aacgggtgc | 1320 |
| ggaccatcgc gtcgaaggca atacttcgt gattgcggcc aatggtatcg aaaccccgaa | 1380 |
| aattctgctg atgagcgcga accgtgattt tccgaatggt gtggccaaca gttccgatat | 1440 |

| | |
|---|---:|
| ggttggccgc aatctgatgg accatccggg caccggcgtg agcttttatg caaacgaaaa | 1500 |
| actgtggccg ggtcgtggtc cgcaggaaat gacctctctg atcggtttcc gtgatggccc | 1560 |
| gtttcgcgcg aatgaagcag cgaagaaaat tcatctgtca aatatgtcgc gtatcaacca | 1620 |
| ggaaacccaa aaatctttta aaggcggtaa actgatgaaa ccggaagaac tggatgcgca | 1680 |
| gatccgtgac cgcagtgccc gctttgttca attcgattgc tttcacgaaa tcctgccgca | 1740 |
| gccggaaaat cgtattgtcc cgtccaaaac cgcaacggac gcagtgggta ttccgcgtcc | 1800 |
| ggaaattacg tatgcgatcg atgactacgt caaacgtggc gcagtgcata cgcgcgaagt | 1860 |
| ttatgctacc gcggccaaag tgctgggcgg caccgaagtg gtcttcaacg atgaatttgc | 1920 |
| gccgaataac cacatcaccg gtgccacgat tatgggcgcg gatgcccgtg actcagtggt | 1980 |
| tgataaagac tgtcgcgcct tcgatcatcc gaacctgttt attagcagca gcagcaccat | 2040 |
| gccgacggtt ggcaccgtta acgtcaccct gacgattgca gctctggcac tgcgtatgtc | 2100 |
| tgatacgctg aaaaaagaag tcgaattcgg ttctggttat ggctctggtc cgccgggtcc | 2160 |
| gattcgtgca ggtgctacca tgccgcatcg tgatcgtggt ccgtgcggtg catgtcacgc | 2220 |
| tattatccag | 2230 |

```
<210> SEQ ID NO 7
<211> LENGTH: 2278
<212> TYPE: DNA
<213> ORGANISM: Artificial
<220> FEATURE:
<223> OTHER INFORMATION: Synthetic

<400> SEQUENCE: 7
```

| | |
|---|---:|
| ccatggctca caatgacaac accccgcact cccgccgtac cggcgatgcg gccgtgaccg | 60 |
| gtattacgcg tcgccagtgg ctgcaaggcg cgctggccct gaccgcagct ggcctgacgg | 120 |
| gttccctggc cctgcgcgca ctggctgatg atccgggcac cgcaccgctg gatacctta | 180 |
| tgacgctgag cgaagctctg acgggcaaaa aaggtctgtc tcgtgttctg ggccagcgtt | 240 |
| ttctgcaagc gctgcaaaaa ggttcattca aaaccgcgga ttcgctgccg cagctggcgg | 300 |
| gcgccctggc aagcggttct ctgaacccgg accaagaagc tctggcgctg aaaatcctgg | 360 |
| aagcatggta tctgggcatt gttgataatg tggttatcac ctacgaagaa gccctgatgt | 420 |
| ttagtgtcgt gtccgacacg ctggtcattc cgagctattg cccgaacaaa ccgggttttct | 480 |
| gggccgaaaa accgatcgaa cgtcaggcat aatggcggat acggataccc agaaagcgga | 540 |
| cgtggtcgtg gttggatccg gcgtggcagg cgcaatcgtg gctcatcaac tggcaatggc | 600 |
| aggtaaaagc gtgatcctgc tggaagctgg tccgcgtatg ccgcgttggg aaattgttga | 660 |
| acgtttccgc aatcaagtcg ataaaaaccga ctttatggca ccgtatccga gcagcgcatg | 720 |
| ggcaccgcat ccggaatatg gtccgccgaa tgattacctg atcctgaaag cgaacacaa | 780 |
| atttaactca cagtacattc gtgcagtggg cggcaccacg tggcattggg cagcctcggc | 840 |
| atggcgcttc atcccgaacg atttaaaat gaaaaccgtg tatggcgttg gtcgtgactg | 900 |
| gccgattcag tacgatgaca tcgaacatta ttaccaacgc gcggaagaag aactgggcgt | 960 |
| gtggggtccg ggcccggaag aagacctgta ttcaccgcgt aaagaaccgt acccgatgcc | 1020 |
| gccgctgccg ctgagtttca tgaacaaac cattaaatcc gctctgaacg ctatgatcc | 1080 |
| gaaatttcac gtggttacgg aaccggtggc ccgtaattcg cgcccgtacg acggtcgccc | 1140 |
| gacctgctgt ggcaacaata actgcatgcc gatttgtccg atcggtgcaa tgtataacgg | 1200 |
| catcgtccat gtggaaaaag ctgaacaggc aggtgctaaa ctgattgata gtgcggtcgt | 1260 |

```
gtacaaactg gaaacgggcc cggacaaacg tattaccgca gctgtttata aagataaaac   1320
gggtgcggac catcgcgtcg aaggcaaata cttcgtgatt gcggccaatg gtatcgaaac   1380
cccgaaaatt ctgctgatga gcgcgaaccg tgattttccg aatggtgtgg ccaacagttc   1440
cgatatggtt ggccgcaatc tgatggacca tccgggcacc ggcgtgagct tttatgcaaa   1500
cgaaaaactg tggccgggtc gtggtccgca ggaaatgacc tctctgatcg gtttccgtga   1560
tggcccgttt cgcgcgaatg aagcagcgaa gaaaattcat ctgtcaaata tgtcgcgtat   1620
caaccaggaa acccaaaaaa tctttaaagg cggtaaactg atgaaaccgg aagaactgga   1680
tgcgcagatc cgtgaccgca gtgcccgctt tgttcaattc gattgctttc acgaaatcct   1740
gccgcagccg gaaatcgta ttgtcccgtc aaaaccgca acggacgcag tgggtattcc   1800
gcgtccggaa attacgtatg cgatcgatga ctacgtcaaa cgtggcgcag tgcatacgcg   1860
cgaagtttat gctaccgcgg ccaaagtgct gggcggcacc gaagtggtct caacgatga   1920 atttgcgccg aataaccaca tcaccggtgc acgattatg ggcgcggatg cccgtgactc   1980
agtggttgat aaagactgtc gcgccttcga tcatccgaac ctgtttatta gcagcagcag   2040
caccatgccg acggttggca ccgttaacgt caccctgacg attgcagctc tggcactgcg   2100
tatgtctgat acgctgaaaa agaagtcga attcggttct ggttatggct ctggtccgcc   2160
gggtccgatt cgtgcaggtg ctaccatgcc gcatcgtgat cgtggtccgt gcggtgcatg   2220
tcacgctatt atccagggca gtggttccgg ccatcaccat caccatcact aaaagctt    2278
```

<210> SEQ ID NO 8
<211> LENGTH: 527
<212> TYPE: PRT
<213> ORGANISM: Artificial
<220> FEATURE:
<223> OTHER INFORMATION: Synthetic

<400> SEQUENCE: 8

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
```

```
            180                 185                 190
His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Tyr Lys Leu Glu Thr Gly
            245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
            325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                    405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
            450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                    485                 490                 495

Arg Ala Phe Asp His Pro Asn Leu Phe Ile Ser Ser Ser Thr Met
                    500                 505                 510

Pro Thr Val Gly Thr Val Asn Val Thr Leu Thr Ile Ala Ala Leu
            515                 520                 525

<210> SEQ ID NO 9
<211> LENGTH: 562
<212> TYPE: PRT
<213> ORGANISM: Artificial
<220> FEATURE:
<223> OTHER INFORMATION: Synthetic

<400> SEQUENCE: 9

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
```

```
                    20                  25                  30
        Ser Val Ile Leu Leu Glu Ala Gly Pro Arg Met Pro Arg Trp Glu Ile
                        35                  40                  45
        Val Glu Arg Phe Arg Asn Gln Val Asp Lys Thr Asp Phe Met Ala Pro
                        50                  55                  60
        Tyr Pro Ser Ser Ala Trp Ala Pro His Pro Glu Tyr Gly Pro Pro Asn
         65                  70                  75                  80
        Asp Tyr Leu Ile Leu Lys Gly Glu His Lys Phe Asn Ser Gln Tyr Ile
                        85                  90                  95
        Arg Ala Val Gly Gly Thr Thr Trp His Trp Ala Ala Ser Ala Trp Arg
                        100                 105                 110
        Phe Ile Pro Asn Asp Phe Lys Met Lys Thr Val Tyr Gly Val Gly Arg
                        115                 120                 125
        Asp Trp Pro Ile Gln Tyr Asp Asp Ile Glu His Tyr Tyr Gln Arg Ala
                        130                 135                 140
        Glu Glu Glu Leu Gly Val Trp Gly Pro Gly Pro Glu Glu Asp Leu Tyr
        145                 150                 155                 160
        Ser Pro Arg Lys Glu Pro Tyr Pro Met Pro Pro Leu Pro Leu Ser Phe
                        165                 170                 175
        Asn Glu Gln Thr Ile Lys Ser Ala Leu Asn Gly Tyr Asp Pro Lys Phe
                        180                 185                 190
        His Val Val Thr Glu Pro Val Ala Arg Asn Ser Arg Pro Tyr Asp Gly
                        195                 200                 205
        Arg Pro Thr Cys Cys Gly Asn Asn Cys Met Pro Ile Cys Pro Ile
                        210                 215                 220
        Gly Ala Met Tyr Asn Gly Ile Val His Val Glu Lys Ala Glu Gln Ala
        225                 230                 235                 240
        Gly Ala Lys Leu Ile Asp Ser Ala Val Val Tyr Lys Leu Glu Thr Gly
                        245                 250                 255
        Pro Asp Lys Arg Ile Thr Ala Ala Val Tyr Lys Asp Lys Thr Gly Ala
                        260                 265                 270
        Asp His Arg Val Glu Gly Lys Tyr Phe Val Ile Ala Ala Asn Gly Ile
                        275                 280                 285
        Glu Thr Pro Lys Ile Leu Leu Met Ser Ala Asn Arg Asp Phe Pro Asn
                        290                 295                 300
        Gly Val Ala Asn Ser Ser Asp Met Val Gly Arg Asn Leu Met Asp His
        305                 310                 315                 320
        Pro Gly Thr Gly Val Ser Phe Tyr Ala Asn Glu Lys Leu Trp Pro Gly
                        325                 330                 335
        Arg Gly Pro Gln Glu Met Thr Ser Leu Ile Gly Phe Arg Asp Gly Pro
                        340                 345                 350
        Phe Arg Ala Asn Glu Ala Ala Lys Lys Ile His Leu Ser Asn Met Ser
                        355                 360                 365
        Arg Ile Asn Gln Glu Thr Gln Lys Ile Phe Lys Gly Gly Lys Leu Met
                        370                 375                 380
        Lys Pro Glu Glu Leu Asp Ala Gln Ile Arg Asp Arg Ser Ala Arg Phe
        385                 390                 395                 400
        Val Gln Phe Asp Cys Phe His Gly Ile Leu Pro Gln Pro Glu Asn Arg
                        405                 410                 415
        Ile Val Pro Ser Lys Thr Ala Thr Asp Ala Val Gly Ile Pro Arg Pro
                        420                 425                 430
        Glu Ile Thr Tyr Ala Ile Asp Asp Tyr Val Lys Arg Gly Ala Val His
                        435                 440                 445
```

-continued

```
Thr Arg Glu Val Tyr Ala Thr Ala Lys Val Leu Gly Gly Thr Glu
    450                 455                 460

Val Val Phe Asn Asp Glu Phe Ala Pro Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Ile Arg Ala Gly Ala
    530                 535                 540

Thr Met Pro His Arg Asp Arg Gly Pro Cys Gly Ala Cys His Ala Ile
545                 550                 555                 560

Ile Gln

<210> SEQ ID NO 10
<211> LENGTH: 586
<212> TYPE: PRT
<213> ORGANISM: Artificial
<220> FEATURE:
<223> OTHER INFORMATION: Synthetic

<400> SEQUENCE: 10

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Ile Glu His Tyr Tyr Gln Arg Ala
130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240
```

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Glu Phe Gly Ser Gly
    530                 535                 540

Tyr Gly Ser Gly Pro Pro Gly Pro Ile Arg Ala Gly Ala Thr Met Pro
545                 550                 555                 560

His Arg Asp Arg Gly Pro Cys Gly Ala Cys His Ala Ile Ile Gln Gly
                565                 570                 575

Ser Gly Ser Gly His His His His His His
            580                 585

<210> SEQ ID NO 11
<211> LENGTH: 575
<212> TYPE: PRT
<213> ORGANISM: Artificial
<220> FEATURE:
<223> OTHER INFORMATION: Synthetic

<400> SEQUENCE: 11

Met Ala Asp Thr Asp Thr Gln Lys Ala Asp Val Val Val Val Gly Ser
1               5                   10                  15

```
Gly Val Ala Gly Ala Ile Val Ala His Gln Leu Ala Met Ala Gly Lys
            20                  25                  30
Ser Val Ile Leu Leu Glu Ala Gly Pro Arg Met Pro Arg Trp Glu Ile
        35                  40                  45
Val Glu Arg Phe Arg Asn Gln Val Asp Lys Thr Asp Phe Met Ala Pro
    50                  55                  60
Tyr Pro Ser Ser Ala Trp Ala Pro His Pro Glu Tyr Gly Pro Pro Asn
65                  70                  75                  80
Asp Tyr Leu Ile Leu Lys Gly Glu His Lys Phe Asn Ser Gln Tyr Ile
                85                  90                  95
Arg Ala Val Gly Gly Thr Thr Trp His Trp Ala Ala Ser Ala Trp Arg
            100                 105                 110
Phe Ile Pro Asn Asp Phe Lys Met Lys Thr Val Tyr Gly Val Gly Arg
        115                 120                 125
Asp Trp Pro Ile Gln Tyr Asp Asp Ile Glu His Tyr Tyr Gln Arg Ala
    130                 135                 140
Glu Glu Glu Leu Gly Val Trp Gly Pro Gly Pro Glu Glu Asp Leu Tyr
145                 150                 155                 160
Ser Pro Arg Lys Glu Pro Tyr Pro Met Pro Pro Leu Pro Leu Ser Phe
                165                 170                 175
Asn Glu Gln Thr Ile Lys Ser Ala Leu Asn Gly Tyr Asp Pro Lys Phe
            180                 185                 190
His Val Val Thr Glu Pro Val Ala Arg Asn Ser Arg Pro Tyr Asp Gly
        195                 200                 205
Arg Pro Thr Cys Cys Gly Asn Asn Asn Cys Met Pro Ile Cys Pro Ile
    210                 215                 220
Gly Ala Met Tyr Asn Gly Ile Val His Val Glu Lys Ala Glu Gln Ala
225                 230                 235                 240
Gly Ala Lys Leu Ile Asp Ser Ala Val Val Tyr Lys Leu Glu Thr Gly
                245                 250                 255
Pro Asp Lys Arg Ile Thr Ala Ala Val Tyr Lys Asp Lys Thr Gly Ala
            260                 265                 270
Asp His Arg Val Glu Gly Lys Tyr Phe Val Ile Ala Ala Asn Gly Ile
        275                 280                 285
Glu Thr Pro Lys Ile Leu Leu Met Ser Ala Asn Arg Asp Phe Pro Asn
    290                 295                 300
Gly Val Ala Asn Ser Ser Asp Met Val Gly Arg Asn Leu Met Asp His
305                 310                 315                 320
Pro Gly Thr Gly Val Ser Phe Tyr Ala Asn Glu Lys Leu Trp Pro Gly
                325                 330                 335
Arg Gly Pro Gln Glu Met Thr Ser Leu Ile Gly Phe Arg Asp Gly Pro
            340                 345                 350
Phe Arg Ala Asn Glu Ala Ala Lys Lys Ile His Leu Ser Asn Met Ser
        355                 360                 365
Arg Ile Asn Gln Glu Thr Gln Lys Ile Phe Lys Gly Gly Lys Leu Met
    370                 375                 380
Lys Pro Glu Glu Leu Asp Ala Gln Ile Arg Asp Arg Ser Ala Arg Phe
385                 390                 395                 400
Val Gln Phe Asp Cys Phe His Glu Ile Leu Pro Gln Pro Glu Asn Arg
                405                 410                 415
Ile Val Pro Ser Lys Thr Ala Thr Asp Ala Val Gly Ile Pro Arg Pro
            420                 425                 430
Glu Ile Thr Tyr Ala Ile Asp Asp Tyr Val Lys Arg Gly Ala Val His
```

```
                435                 440                 445
Thr Arg Glu Val Tyr Ala Thr Ala Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Glu Phe Gly Ser Gly
530                 535                 540

Tyr Gly Ser Gly Pro Pro Gly Pro Ile Arg Ala Gly Ala Thr Met Pro
545                 550                 555                 560

His Arg Asp Arg Gly Pro Cys Gly Ala Cys His Ala Ile Ile Gln
                565                 570                 575

<210> SEQ ID NO 12
<211> LENGTH: 586
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (42)..(42)
<223> OTHER INFORMATION: X is R or a non-canonical amino acid.
<220> FEATURE:
<221> NAME/KEY: X
<222> LOCATION: (247)..(247)
<223> OTHER INFORMATION: X is S or a non-canonical amino acid.
<220> FEATURE:
<221> NAME/KEY: X
<222> LOCATION: (395)..(395)
<223> OTHER INFORMATION: X is D or a non-canonical amino acid.
<220> FEATURE:
<221> NAME/KEY: X
<222> LOCATION: (558)..(558)
<223> OTHER INFORMATION: X is T or a non-canonical amino acid.
<220> FEATURE:
<221> NAME/KEY: X
<222> LOCATION: (560)..(560)
<223> OTHER INFORMATION: X is P or a non-canonical amino acid.

<400> SEQUENCE: 12

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Xaa Met Pro Arg Trp Glu Ile
                35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125
```

```
Asp Trp Pro Ile Gln Tyr Asp Asp Ile Glu His Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
            195                 200                 205

Arg Pro Thr Cys Cys Gly Asn Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Xaa Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
    275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
                355                 360                 365

Arg Ile Asn Gln Glu Thr Gln Lys Ile Phe Lys Gly Gly Lys Leu Met
370                 375                 380

Lys Pro Glu Glu Leu Asp Ala Gln Ile Arg Xaa Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Tyr Val Lys Arg Gly Ala Val His
                435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Glu Phe Gly Ser Gly
530                 535                 540
```

-continued

```
Tyr Gly Ser Gly Pro Pro Gly Pro Ile Arg Ala Gly Ala Xaa Met Xaa
545                 550                 555                 560

His Arg Asp Arg Gly Pro Cys Gly Ala Cys His Ala Ile Ile Gln Gly
                565                 570                 575

Ser Gly Ser Gly His His His His His His
            580                 585

<210> SEQ ID NO 13
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (42)..(42)
<223> OTHER INFORMATION: X is R or a non-canonical amino acid
<220> FEATURE:
<221> NAME/KEY: X
<222> LOCATION: (247)..(247)
<223> OTHER INFORMATION: X is S or a non-canonical amino acid
<220> FEATURE:
<221> NAME/KEY: X
<222> LOCATION: (395)..(395)
<223> OTHER INFORMATION: X is D or a non-canonical amino acid
<220> FEATURE:
<221> NAME/KEY: X
<222> LOCATION: (558)..(558)
<223> OTHER INFORMATION: X is T or a non-canonical amino acid
<220> FEATURE:
<221> NAME/KEY: X
<222> LOCATION: (560)..(560)
<223> OTHER INFORMATION: X is P or a non-canonical amino acid

<400> SEQUENCE: 13

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Xaa Met Pro Arg Trp Glu Ile
        35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Asn Cys Met Pro Ile Cys Pro Ile
```

```
                    210                 215                 220
Gly Ala Met Tyr Asn Gly Ile Val His Val Glu Lys Ala Glu Gln Ala
225                 230                 235                 240

Gly Ala Lys Leu Ile Asp Xaa Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
                275                 280                 285

Glu Thr Pro Lys Ile Leu Leu Met Ser Ala Asn Arg Asp Phe Pro Asn
                290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
                355                 360                 365

Arg Ile Asn Gln Glu Thr Gln Lys Ile Phe Lys Gly Gly Lys Leu Met
                370                 375                 380

Lys Pro Glu Glu Leu Asp Ala Gln Ile Arg Xaa Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
                435                 440                 445

Thr Arg Glu Val Tyr Ala Thr Ala Lys Val Leu Gly Gly Thr Glu
                450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Glu Phe Gly Ser Gly
                530                 535                 540

Tyr Gly Ser Gly Pro Pro Gly Pro Ile Arg Ala Gly Ala Xaa Met Xaa
545                 550                 555                 560

His Arg Asp Arg Gly Pro Cys Gly Ala Cys His Ala Ile Ile Gln
                565                 570                 575

<210> SEQ ID NO 14
<211> LENGTH: 1727
<212> TYPE: DNA
<213> ORGANISM: Artificial
<220> FEATURE:
<223> OTHER INFORMATION: Synthetic

<400> SEQUENCE: 14
tggcggatac ggatacccag aaagcggacg tggtcgtggt tggatccggc gtggcaggcg    60
```

| caatcgtggc tcatcaactg gcaatggcag gtaaaagcgt gatcctgctg gaagctggtc | 120 |
| cgtagatgcc gcgttgggaa attgttgaac gtttccgcaa tcaagtcgat aaaaccgact | 180 |
| ttatggcacc gtatccgagc agcgcatggg caccgcatcc ggaatatggt ccgccgaatg | 240 |
| attacctgat cctgaaaggc gaacacaaat ttaactcaca gtacattcgt gcagtgggcg | 300 |
| gcaccacgtg gcattgggca gcctcggcat ggcgcttcat cccgaacgat tttaaaatga | 360 |
| aaaccgtgta tggcgttggt cgtgactggc gattcagta cgatgacatc gaacattatt | 420 |
| accaacgcgc ggaagaagaa ctgggcgtgt ggggtccggg cccggaagaa gacctgtatt | 480 |
| caccgcgtaa agaaccgtac ccgatgccgc cgctgccgct gagtttcaat gaacaaacca | 540 |
| ttaaatccgc tctgaacggc tatgatccga aatttcacgt ggttacggaa ccggtggccc | 600 |
| gtaattcgcg cccgtacgac ggtcgcccga cctgctgtgg caacaataac tgcatgccga | 660 |
| tttgtccgat cggtgcaatg tataacggca tcgtccatgt ggaaaaagct gaacaggcag | 720 |
| gtgctaaact gattgatagt gcggtcgtgt acaaactgga aacgggcccg acaaacgta | 780 |
| ttaccgcagc tgtttataaa gataaaacgg gtgcggacca tcgcgtcgaa ggcaaatact | 840 |
| tcgtgattgc ggccaatggt atcgaaaccc gaaaattct gctgatgagc gcgaaccgtg | 900 |
| attttccgaa tggtgtggcc aacagttccg atatggttgg ccgcaatctg atggaccatc | 960 |
| cgggcaccgg cgtgagcttt tatgcaaacg aaaaactgtg gccgggtcgt ggtccgcagg | 1020 |
| aaatgacctc tctgatcggt ttccgtgatg gcccgtttcg cgcgaatgaa gcagcgaaga | 1080 |
| aaattcatct gtcaaatatg tcgcgtatca accaggaaac ccaaaaaatc tttaaaggcg | 1140 |
| gtaaactgat gaaaccggaa gaactggatg cgcagatccg tgaccgcagt gcccgctttg | 1200 |
| ttcaattcga ttgcttttcac gaaatcctgc cgcagccgga aaatcgtatt gtcccgtcca | 1260 |
| aaaccgcaac ggacgcagtg ggtattccgc gtccggaaat tacgtatgcg atcgatgact | 1320 |
| acgtcaaacg tggcgcagtg catacgcgcg aagtttatgc taccgcgcc aaagtgctgg | 1380 |
| gcggcaccga agtggtcttc aacgatgaat ttgcgccgaa taccacatc accggtgcca | 1440 |
| cgattatggg cgcggatgcc cgtgactcag tggttgataa agactgtcgc gccttcgatc | 1500 |
| atccgaacct gtttattagc agcagcagca ccatgccgac ggttggcacc gttaacgtca | 1560 |
| ccctgacgat tgcagctctg cactgcgta tgtctgatac gctgaaaaaa gaagtcgaat | 1620 |
| tcggttctgg ttatggctct ggtccgccgg gtccgattcg tgcaggtgct accatgccgc | 1680 |
| atcgtgatcg tggtccgtgc ggtgcatgtc acgctattat ccagtaa | 1727 |

<210> SEQ ID NO 15
<211> LENGTH: 1728
<212> TYPE: DNA
<213> ORGANISM: Artificial
<220> FEATURE:
<223> OTHER INFORMATION: Synthetic

<400> SEQUENCE: 15

| atggcggata cggataccca gaaagcggac gtggtcgtgg ttggatccgg cgtggcaggc | 60 |
| gcaatcgtgg ctcatcaact ggcaatggca ggtaaaagcg tgatcctgct ggaagctggt | 120 |
| ccgcgtatgc cgcgttggga aattgttgaa cgtttccgca atcaagtcga taaaaccgac | 180 |
| tttatggcac cgtatccgag cagcgcatgg gcaccgcatc cggaatatgg tccgccgaat | 240 |
| gattacctga tcctgaaagg cgaacacaaa tttaactcac agtacattcg tgcagtgggc | 300 |
| ggcaccacgt ggcattgggc agcctcggca tggcgcttca tcccgaacga ttttaaaatg | 360 |

| | | | |
|---|---|---|---|
| aaaaccgtgt | atggcgttgg tcgtgactgg ccgattcagt acgatgacat cgaacattat | 420 |
| taccaacgcg | cggaagaaga actgggcgtg tggggtccgg cccggaaga agacctgtat | 480 |
| tcaccgcgta | aagaaccgta cccgatgccg ccgctgccgc tgagtttcaa tgaacaaacc | 540 |
| attaaatccg | ctctgaacgg ctatgatccg aaatttcacg tggttacgga accggtggcc | 600 |
| cgtaattcgc | gcccgtacga cggtcgcccg acctgctgtg gcaacaataa ctgcatgccg | 660 |
| atttgtccga | tcggtgcaat gtataacggc atcgtccatg tggaaaaagc tgaacaggca | 720 |
| ggtgctaaac | tgattgatta ggcggtcgtg tacaaactgg aaacgggccc ggacaaacgt | 780 |
| attaccgcag | ctgtttataa agataaaacg ggtgcggacc atcgcgtcga aggcaaatac | 840 |
| ttcgtgattg | cggccaatgg tatcgaaacc ccgaaaattc tgctgatgag cgcgaaccgt | 900 |
| gattttccga | atggtgtggc caacagttcc gatatggttg ccgcaatctg atggaccat | 960 |
| ccgggcaccg | gcgtgagctt ttatgcaaac gaaaaactgt ggccgggtcg tggtccgcag | 1020 |
| gaaatgacct | ctctgatcgg tttccgtgat ggcccgtttc gcgcgaatga agcagcgaag | 1080 |
| aaaattcatc | tgtcaaatat gtcgcgtatc aaccaggaaa cccaaaaaat ctttaaaggc | 1140 |
| ggtaaactga | tgaaaccgga gaactggatg gcgcagatcc gtgaccgcag tgcccgcttt | 1200 |
| gttcaattcg | attgctttca cgaaatcctg ccgcagccgg aaaatcgtat tgtcccgtcc | 1260 |
| aaaaccgcaa | cggacgcagt gggtattccg cgtccggaaa ttacgtatgc gatcgatgac | 1320 |
| tacgtcaaac | gtggcgcagt gcatacgcgc gaagtttatg ctaccgcggc caaagtgctg | 1380 |
| ggcggcaccg | aagtggtctt caacgatgaa tttgcgccga ataaccacat caccggtgcc | 1440 |
| acgattatgg | gcgcggatgc ccgtgactca gtggttgata agactgtcg cgccttcgat | 1500 |
| catccgaacc | tgtttattag cagcagcagc accatgccga cggttggcac cgttaacgtc | 1560 |
| accctgacga | ttgcagctct ggcactgcgt atgtctgata cgctgaaaaa agaagtcgaa | 1620 |
| ttcggttctg | gttatggctc tggtccgccg ggtccgattc gtgcaggtgc taccatgccg | 1680 |
| catcgtgatc | gtggtccgtg cggtgcatgt cacgctatta tccagtaa | 1728 |

<210> SEQ ID NO 16
<211> LENGTH: 1729
<212> TYPE: DNA
<213> ORGANISM: Artificial
<220> FEATURE:
<223> OTHER INFORMATION: Synthetic

<400> SEQUENCE: 16

| | | | |
|---|---|---|---|
| atggcggata | cggataccca gaaagcggac gtggtcgtgg ttggatccgg cgtggcaggc | 60 |
| gcaatcgtgg | ctcatcaact ggcaatggca ggtaaaagcg tgatcctgct ggaagctggt | 120 |
| ccgcgtatgc | cgcgttggga aattgttgaa cgtttccgca atcaagtcga taaaaccgac | 180 |
| tttatggcac | cgtatccgag cagcgcatgg gcaccgcatc cggaatatgg tccgccgaat | 240 |
| gattacctga | tcctgaaagg cgaacacaaa tttaactcac agtacattcg tgcagtgggc | 300 |
| ggcaccacgt | ggcattgggc agcctcggca tggcgcttca tcccgaacga ttttaaaatg | 360 |
| aaaaccgtgt | atggcgttgg tcgtgactgg ccgattcagt acgatgacat cgaacattat | 420 |
| taccaacgcg | cggaagaaga actgggcgtg tggggtccgg cccggaaga agacctgtat | 480 |
| tcaccgcgta | aagaaccgta cccgatgccg ccgctgccgc tgagtttcaa tgaacaaacc | 540 |
| attaaatccg | ctctgaacgg ctatgatccg aaatttcacg tggttacgga accggtggcc | 600 |
| cgtaattcgc | gcccgtacga cggtcgcccg acctgctgtg gcaacaataa ctgcatgccg | 660 |
| atttgtccga | tcggtgcaat gtataacggc atcgtccatg tggaaaaagc tgaacaggca | 720 |

-continued

```
ggtgctaaac tgattgatag tgcggtcgtg tacaaactgg aaacgggccc ggacaaacgt      780
attaccgcag ctgtttataa agataaaacg ggtgcggacc atcgcgtcga aggcaaatac      840
ttcgtgattg cggccaatgg tatcgaaacc ccgaaaattc tgctgatgag cgcgaaccgt      900
gattttccga atggtgtggc caacagttcc gatatggttg ccgcaatcct gatgaccat      960 ccgggcaccg gcgtgagctt ttatgcaaac gaaaaactgt ggccgggtcg tggtccgcag     1020
gaaatgacct ctctgatcgg tttccgtgat ggcccgtttc gcgcgaatga agcagcgaag     1080
aaaattcatc tgtcaaatat gtcgcgtatc aaccaggaaa cccaaaaaat ctttaaaggc     1140
ggtaaactga tgaaaccgga agaactggat gcgcagatcc gttagcgcag tgcccgcttt     1200
gttcaattcg attgctttca cgaaatcctg ccgcagccgg aaaatcgtat tgtcccgtcc     1260
aaaaccgcaa cggacgcagt gggtattccg cgtccggaaa ttacgtatgc gatcgatgac     1320
tacgtcaaac gtggcgcagt gcatacgcgc gaagtttatg ctaccgcggc caaagtgctg     1380
ggcggcaccg aagtggtctt caacgatgaa tttgcgccga ataaccacat caccggtgcc     1440
acgattatgg gcgcggatgc ccgtgactca gtggttgata aagactgtcg cgccttcgat     1500
catccgaacc tgtttattag cagcagcagc accatgccga cggttggcac cgttaacgtc     1560
accctgacga ttgcagctct ggcactgcgt atgtctgata cgctgaaaaa agaagtcgaa     1620
ttcggttctg gttatggctc tggtccgccg ggtccgattc gtgcaggtgc taccatgccg     1680
catcgtgatc gtggtccgtg cggtgcatgt cacgctatta tccaggtaa                 1729
```

```
<210> SEQ ID NO 17
<211> LENGTH: 1728
<212> TYPE: DNA
<213> ORGANISM: Artificial
<220> FEATURE:
<223> OTHER INFORMATION: Synthetic

<400> SEQUENCE: 17
```

```
atggcggata cggatacccca gaaagcggac gtggtcgtgg ttggatccgg cgtggcaggc       60
gcaatcgtgg ctcatcaact ggcaatggca ggtaaaagcg tgatcctgct ggaagctggt      120
ccgcgtatgc cgcgttggga aattgttgaa cgtttccgca atcaagtcga taaaaccgac      180
tttatggcac cgtatccgag cagcgcatgg gcaccgcatc cggaatatgg tccgccgaat      240
gattacctga tcctgaaagg cgaacacaaa tttaactcac agtacattcg tgcagtgggc      300
ggcaccacgt ggcattgggc agcctcggca tggcgcttca tcccgaacga ttttaaaatg      360 aaaccgtgt atggcgttgg tcgtgactgg ccgattcagt acgatgacat cgaacattat      420
taccaacgcg cggaagaaga actgggcgtg tggggtccgg gcccggaaga agacctgtat      480
tcaccgcgta agaaccgta cccgatgccc cgctgccgc tgagtttcaa tgaacaaacc      540
attaaatccg ctctgaacgg ctatgatccg aaatttcacg tggttacgga accggtggcc      600
cgtaattcgc gcccgtacga cggtcgcccg acctgctgtg caacaataa ctgcatgccg      660 atttgtccga tcggtgcaat gtataacggc atcgtccatg tggaaaaagc tgaacaggca      720
ggtgctaaac tgattgatag tgcggtcgtg tacaaactgg aaacgggccc ggacaaacgt      780
attaccgcag ctgtttataa agataaaacg ggtgcggacc atcgcgtcga aggcaaatac      840
ttcgtgattg cggccaatgg tatcgaaacc ccgaaaattc tgctgatgag cgcgaaccgt      900
gattttccga atggtgtggc caacagttcc gatatggttg ccgcaatcct gatgaccat      960 ccgggcaccg gcgtgagctt ttatgcaaac gaaaaactgt ggccgggtcg tggtccgcag     1020
```

| | |
|---|---|
| gaaatgacct ctctgatcgg tttccgtgat ggcccgtttc gcgcgaatga agcagcgaag | 1080 |
| aaaattcatc tgtcaaatat gtcgcgtatc aaccaggaaa cccaaaaaat ctttaaaggc | 1140 |
| ggtaaactga tgaaaccgga agaactggat gcgcagatcc gtgaccgcag tgcccgcttt | 1200 |
| gttcaattcg attgctttca cgaaatcctg ccgcagccgg aaaatcgtat tgtcccgtcc | 1260 |
| aaaaccgcaa cggacgcagt gggtattccg cgtccggaaa ttacgtatgc gatcgatgac | 1320 |
| tacgtcaaac gtggcgcagt gcatacgcgc gaagtttatg ctaccgcggc caaagtgctg | 1380 |
| ggcggcaccg aagtggtctt caacgatgaa tttgcgccga taaccacat caccggtgcc | 1440 |
| acgattatgg gcgcggatgc ccgtgactca gtggttgata agactgtcg cgccttcgat | 1500 |
| catccgaacc tgtttattag cagcagcagc accatgccga cggttggcac cgttaacgtc | 1560 |
| accctgacga ttgcagctct ggcactgcgt atgtctgata cgctgaaaaa agaagtcgaa | 1620 |
| ttcggttctg gttatggctc tggtccgccg ggtccgattc gtgcaggtgc ttagatgccg | 1680 |
| catcgtgatc gtggtccgtg cggtgcatgt cacgctatta ccagtaa | 1728 |

<210> SEQ ID NO 18
<211> LENGTH: 1728
<212> TYPE: DNA
<213> ORGANISM: Artificial
<220> FEATURE:
<223> OTHER INFORMATION: Synthetic

<400> SEQUENCE: 18

| | |
|---|---|
| atggcggata cggataccca gaaagcggac gtggtcgtgg ttggatccgg cgtggcaggc | 60 |
| gcaatcgtgg ctcatcaact ggcaatggca gtaaaagcg tgatcctgct ggaagctggt | 120 |
| ccgcgtatgc cgcgttggga aattgttgaa cgtttccgca atcaagtcga taaaaccgac | 180 |
| tttatggcac cgtatccgag cagcgcatgg gcaccgcatc cggaatatgg tccgccgaat | 240 |
| gattacctga tcctgaaagg cgaacacaaa tttaactcac agtacattcg tgcagtgggc | 300 |
| ggcaccacgt ggcattgggc agcctcggca tggcgcttca tcccgaacga ttttaaaatg | 360 |
| aaaaccgtgt atggcgttgg tcgtgactgg ccgattcagt acgatgacat cgaacattat | 420 |
| taccaacgcg cggaagaaga actgggcgtg tggggtccgg gcccggaaga agacctgtat | 480 |
| tcaccgcgta agaaccgta cccgatgccg ccgctgccgc tgagtttcaa tgaacaaacc | 540 |
| attaaatccg ctctgaacgg ctatgatccg aaatttcacg tggttacgga accggtggcc | 600 |
| cgtaattcgc gcccgtacga cggtcgcccg acctgctgtg gcaacaataa ctgcatgccg | 660 |
| atttgtccga tcggtgcaat gtataacggc atcgtccatg tggaaaaagc tgaacaggca | 720 |
| ggtgctaaac tgattgatag tgcggtcgtg tacaaactgg aaacgggccc ggacaaacgt | 780 |
| attaccgcag ctgttttataa agataaaacg ggtgcggacc atcgcgtcga aggcaaatac | 840 |
| ttcgtgattg cggccaatgg tatcgaaacc ccgaaaattc tgctgatgag cgcgaaccgt | 900 |
| gattttccga atggtgtggc caacagttcc gatatggttg ccgcaatct gatgaccat | 960 |
| ccgggcaccg gcgtgagctt ttatgcaaac gaaaaactgt ggccgggtcg tggtccgcag | 1020 |
| gaaatgacct ctctgatcgg tttccgtgat ggcccgtttc gcgcgaatga agcagcgaag | 1080 |
| aaaattcatc tgtcaaatat gtcgcgtatc aaccaggaaa cccaaaaaat ctttaaaggc | 1140 |
| ggtaaactga tgaaaccgga agaactggat gcgcagatcc gtgaccgcag tgcccgcttt | 1200 |
| gttcaattcg attgctttca cgaaatcctg ccgcagccgg aaaatcgtat tgtcccgtcc | 1260 |
| aaaaccgcaa cggacgcagt gggtattccg cgtccggaaa ttacgtatgc gatcgatgac | 1320 |
| tacgtcaaac gtggcgcagt gcatacgcgc gaagtttatg ctaccgcggc caaagtgctg | 1380 |

-continued

```
ggcggcaccg aagtggtctt caacgatgaa tttgcgccga ataaccacat caccggtgcc    1440
acgattatgg gcgcggatgc ccgtgactca gtggttgata agactgtcg cgccttcgat     1500 catccgaacc tgtttattag cagcagcagc accatgccga cggttggcac cgttaacgtc    1560
accctgacga ttgcagctct ggcactgcgt atgtctgata cgctgaaaaa agaagtcgaa    1620
ttcggttctg gttatggctc tggtccgccg ggtccgattc gtgcaggtgc taccatgtag    1680
catcgtgatc gtggtccgtg cggtgcatgt cacgctatta tccagtaa                1728
```

<210> SEQ ID NO 19
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (42)..(42)
<223> OTHER INFORMATION: X is a non-canonical amino acid

<400> SEQUENCE: 19

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Xaa Met Pro Arg Trp Glu Ile
        35                  40                  45

Val Glu Arg Phe Arg Asn Gln Val Asp Lys Thr Asp Phe Met Ala Pro
    50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
    130                 135                 140

Glu Glu Glu Leu Gly Val Trp Gly Pro Gly Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Val Tyr Lys Asp Lys Thr Gly Ala
            260                 265                 270

Asp His Arg Val Glu Gly Lys Tyr Phe Val Ile Ala Ala Asn Gly Ile
```

```
            275                 280                 285
Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Glu Phe Gly Ser Gly
    530                 535                 540

Tyr Gly Ser Gly Pro Pro Gly Pro Ile Arg Ala Gly Ala Thr Met Pro
545                 550                 555                 560

His Arg Asp Arg Gly Pro Cys Gly Ala Cys His Ala Ile Ile Gln
                565                 570                 575
```

<210> SEQ ID NO 20
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (247)..(247)
<223> OTHER INFORMATION: X is a non-canonical amino acid

<400> SEQUENCE: 20

```
Met Ala Asp Thr Asp Thr Gln Lys Ala Asp Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45
```

Val Glu Arg Phe Arg Asn Gln Val Asp Lys Thr Asp Phe Met Ala Pro
        50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
                115                 120                 125

Asp Trp Pro Ile Gln Tyr Asp Asp Ile Glu His Tyr Tyr Gln Arg Ala
        130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
                180                 185                 190

His Val Val Thr Glu Pro Val Ala Arg Asn Ser Arg Pro Tyr Asp Gly
                195                 200                 205

Arg Pro Thr Cys Cys Gly Asn Asn Asn Cys Met Pro Ile Cys Pro Ile
        210                 215                 220

Gly Ala Met Tyr Asn Gly Ile Val His Val Glu Lys Ala Glu Gln Ala
225                 230                 235                 240

Gly Ala Lys Leu Ile Asp Xaa Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
        370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
450                 455                 460

Val Val Phe Asn Asp Glu Phe Ala Pro Asn Asn His Ile Thr Gly Ala

```
                465                 470                 475                 480
Thr Ile Met Gly Ala Asp Ala Arg Asp Ser Val Val Asp Lys Asp Cys
                485                 490                 495
Arg Ala Phe Asp His Pro Asn Leu Phe Ile Ser Ser Ser Thr Met
                500                 505                 510
Pro Thr Val Gly Thr Val Asn Val Thr Leu Thr Ile Ala Ala Leu Ala
                515                 520                 525
Leu Arg Met Ser Asp Thr Leu Lys Lys Glu Val Glu Phe Gly Ser Gly
530                 535                 540
Tyr Gly Ser Gly Pro Pro Gly Pro Ile Arg Ala Gly Ala Thr Met Pro
545                 550                 555                 560
His Arg Asp Arg Gly Pro Cys Gly Ala Cys His Ala Ile Ile Gln
                565                 570                 575

<210> SEQ ID NO 21
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (395)..(395)
<223> OTHER INFORMATION: X is a non-canonical amino acid

<400> SEQUENCE: 21

Met Ala Asp Thr Asp Thr Gln Lys Ala Asp Val Val Val Gly Ser
1               5                   10                  15
Gly Val Ala Gly Ala Ile Val Ala His Gln Leu Ala Met Ala Gly Lys
                20                  25                  30
Ser Val Ile Leu Leu Glu Ala Gly Pro Arg Met Pro Arg Trp Glu Ile
                35                  40                  45
Val Glu Arg Phe Arg Asn Gln Val Asp Lys Thr Asp Phe Met Ala Pro
            50                  55                  60
Tyr Pro Ser Ser Ala Trp Ala Pro His Pro Glu Tyr Gly Pro Pro Asn
65                  70                  75                  80
Asp Tyr Leu Ile Leu Lys Gly Glu His Lys Phe Asn Ser Gln Tyr Ile
                85                  90                  95
Arg Ala Val Gly Gly Thr Thr Trp His Trp Ala Ala Ser Ala Trp Arg
                100                 105                 110
Phe Ile Pro Asn Asp Phe Lys Met Lys Thr Val Tyr Gly Val Gly Arg
                115                 120                 125
Asp Trp Pro Ile Gln Tyr Asp Asp Ile Glu His Tyr Tyr Gln Arg Ala
            130                 135                 140
Glu Glu Glu Leu Gly Val Trp Gly Pro Gly Pro Glu Glu Asp Leu Tyr
145                 150                 155                 160
Ser Pro Arg Lys Glu Pro Tyr Pro Met Pro Pro Leu Pro Leu Ser Phe
                165                 170                 175
Asn Glu Gln Thr Ile Lys Ser Ala Leu Asn Gly Tyr Asp Pro Lys Phe
                180                 185                 190
His Val Val Thr Glu Pro Val Ala Arg Asn Ser Arg Pro Tyr Asp Gly
                195                 200                 205
Arg Pro Thr Cys Cys Gly Asn Asn Asn Cys Met Pro Ile Cys Pro Ile
            210                 215                 220
Gly Ala Met Tyr Asn Gly Ile Val His Val Glu Lys Ala Glu Gln Ala
225                 230                 235                 240
```

Gly Ala Lys Leu Ile Asp Ser Ala Val Val Tyr Lys Leu Glu Thr Gly
            245                 250                 255

Pro Asp Lys Arg Ile Thr Ala Ala Val Tyr Lys Asp Lys Thr Gly Ala
        260                 265                 270

Asp His Arg Val Glu Gly Lys Tyr Phe Val Ile Ala Ala Asn Gly Ile
    275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
    370                 375                 380

Lys Pro Glu Glu Leu Asp Ala Gln Ile Arg Xaa Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
            420                 425                 430

Glu Ile Thr Tyr Ala Ile Asp Asp Tyr Val Lys Arg Gly Ala Val His
        435                 440                 445

Thr Arg Glu Val Tyr Ala Thr Ala Lys Val Leu Gly Gly Thr Glu
    450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
        515                 520                 525

Leu Arg Met Ser Asp Thr Leu Lys Lys Glu Val Glu Phe Gly Ser Gly
    530                 535                 540

Tyr Gly Ser Gly Pro Pro Gly Pro Ile Arg Ala Gly Ala Thr Met Pro
545                 550                 555                 560

His Arg Asp Arg Gly Pro Cys Gly Ala Cys His Ala Ile Ile Gln
                565                 570                 575

<210> SEQ ID NO 22
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (558)..(558)
<223> OTHER INFORMATION: X is a non-canonical amino acid

<400> SEQUENCE: 22

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ser Val Ile Leu Leu Glu Ala Gly Pro Arg Met Pro Arg Trp Glu Ile
        35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Thr Val Tyr Gly Val Gly Arg
        115                 120                 125

Asp Trp Pro Ile Gln Tyr Asp Asp Ile Glu His Tyr Tyr Gln Arg Ala
130                 135                 140

Glu Glu Glu Leu Gly Val Trp Gly Pro Gly Pro Glu Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
        195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
            260                 265                 270

Asp His Arg Val Glu Gly Lys Tyr Phe Val Ile Ala Ala Asn Gly Ile
        275                 280                 285

Glu Thr Pro Lys Ile Leu Leu Met Ser Ala Asn Arg Asp Phe Pro Asn
290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Asn Glu Ala Ala Lys Lys Ile His Leu Ser Asn Met Ser
        355                 360                 365

Arg Ile Asn Gln Glu Thr Gln Lys Ile Phe Lys Gly Gly Lys Leu Met
370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Asp Ala Val Gly Ile Pro Arg Pro
            420                 425                 430

```
Glu Ile Thr Tyr Ala Ile Asp Asp Tyr Val Lys Arg Gly Ala Val His
            435                 440                 445

Thr Arg Glu Val Tyr Ala Thr Ala Ala Lys Val Leu Gly Gly Thr Glu
450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
                500                 505                 510

Pro Thr Val Gly Thr Val Asn Val Thr Leu Thr Ile Ala Ala Leu Ala
                515                 520                 525

Leu Arg Met Ser Asp Thr Leu Lys Lys Glu Val Glu Phe Gly Ser Gly
530                 535                 540

Tyr Gly Ser Gly Pro Pro Gly Pro Ile Arg Ala Gly Ala Xaa Met Pro
545                 550                 555                 560

His Arg Asp Arg Gly Pro Cys Gly Ala Cys His Ala Ile Ile Gln
                565                 570                 575

<210> SEQ ID NO 23
<211> LENGTH: 575
<212> TYPE: PRT
<213> ORGANISM: Artificial
<220> FEATURE:
<223> OTHER INFORMATION: Synthetic
<220> FEATURE:
<221> NAME/KEY: X
<222> LOCATION: (560)..(560)
<223> OTHER INFORMATION: X is a non-canonical amino acid

<400> SEQUENCE: 23

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
                20                  25                  30

Ser Val Ile Leu Leu Glu Ala Gly Pro Arg Met Pro Arg Trp Glu Ile
            35                  40                  45

Val Glu Arg Phe Arg Asn Gln Val Asp Lys Thr Asp Phe Met Ala Pro
50                  55                  60

Tyr Pro Ser Ser Ala Trp Ala Pro His Pro Glu Tyr Gly Pro Pro Asn
65                  70                  75                  80

Asp Tyr Leu Ile Leu Lys Gly Glu His Lys Phe Asn Ser Gln Tyr Ile
                85                  90                  95

Arg Ala Val Gly Gly Thr Thr Trp His Trp Ala Ala Ser Ala Trp Arg
                100                 105                 110

Phe Ile Pro Asn Asp Phe Lys Met Lys Thr Val Tyr Gly Val Gly Arg
            115                 120                 125

Asp Trp Pro Ile Gln Tyr Asp Asp Ile Glu His Tyr Tyr Gln Arg Ala
        130                 135                 140

Glu Glu Glu Leu Gly Val Trp Gly Pro Gly Pro Glu Asp Leu Tyr
145                 150                 155                 160

Ser Pro Arg Lys Glu Pro Tyr Pro Met Pro Pro Leu Pro Leu Ser Phe
                165                 170                 175

Asn Glu Gln Thr Ile Lys Ser Ala Leu Asn Gly Tyr Asp Pro Lys Phe
            180                 185                 190

His Val Val Thr Glu Pro Val Ala Arg Asn Ser Arg Pro Tyr Asp Gly
            195                 200                 205
```

Arg Pro Thr Cys Cys Gly Asn Asn Cys Met Pro Ile Cys Pro Ile
    210                 215                 220

Gly Ala Met Tyr Asn Gly Ile Val His Val Glu Lys Ala Glu Gln Ala
225                 230                 235                 240

Gly Ala Lys Leu Ile Asp Ser Ala Val Val Tyr Lys Leu Glu Thr Gly
                245                 250                 255

Pro Asp Lys Arg Ile Thr Ala Ala Val Tyr Lys Asp Lys Thr Gly Ala
                260                 265                 270

Asp His Arg Val Glu Gly Lys Tyr Phe Val Ile Ala Ala Asn Gly Ile
            275                 280                 285

Glu Thr Pro Lys Ile Leu Leu Met Ser Ala Asn Arg Asp Phe Pro Asn
            290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Asn Glu Lys Leu Trp Pro Gly
                325                 330                 335

Arg Gly Pro Gln Glu Met Thr Ser Leu Ile Gly Phe Arg Asp Gly Pro
                340                 345                 350

Phe Arg Ala Asn Glu Ala Ala Lys Lys Ile His Leu Ser Asn Met Ser
            355                 360                 365

Arg Ile Asn Gln Glu Thr Gln Lys Ile Phe Lys Gly Gly Lys Leu Met
            370                 375                 380

Lys Pro Glu Glu Leu Asp Ala Gln Ile Arg Asp Arg Ser Ala Arg Phe
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Val Gly Ile Pro Arg Pro
                420                 425                 430

Glu Ile Thr Tyr Ala Ile Asp Asp Tyr Val Lys Arg Gly Ala Val His
            435                 440                 445

Thr Arg Glu Val Tyr Ala Thr Ala Lys Val Leu Gly Gly Thr Glu
            450                 455                 460

Val Val Phe Asn Asp Glu Phe Ala Pro Asn Asn His Ile Thr Gly Ala
465                 470                 475                 480

Thr Ile Met Gly Ala Asp Ala Arg Asp Ser Val Val Asp Lys Asp Cys
                485                 490                 495

Arg Ala Phe Asp His Pro Asn Leu Phe Ile Ser Ser Ser Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val Glu Phe Gly Ser Gly
            530                 535                 540

Tyr Gly Ser Gly Pro Pro Gly Pro Ile Arg Ala Gly Ala Thr Met Xaa
545                 550                 555                 560

His Arg Asp Arg Gly Pro Cys Gly Ala Cys His Ala Ile Ile Gln
                565                 570                 575

<210> SEQ ID NO 24
<211> LENGTH: 18
<212> TYPE: DNA
<213> ORGANISM: Artificial
<220> FEATURE:
<223> OTHER INFORMATION: Synthetic

<400> SEQUENCE: 24

```
catcaccatc accatcac                                              18

<210> SEQ ID NO 25
<211> LENGTH: 15
<212> TYPE: DNA
<213> ORGANISM: Artificial
<220> FEATURE:
<223> OTHER INFORMATION: Synthetic

<400> SEQUENCE: 25
ggcagtggtt ccggc                                                 15

<210> SEQ ID NO 26
<211> LENGTH: 2278
<212> TYPE: DNA
<213> ORGANISM: Artificial
<220> FEATURE:
<223> OTHER INFORMATION: Synthetic

<400> SEQUENCE: 26
ccatggctca caatgacaac accccgcact cccgccgtac cggcgatgcg gccgtgaccg      60
gtattacgcg tcgccagtgg ctgcaaggcg cgctggccct gaccgcagct ggcctgacgg     120
gttccctggc cctgcgcgca ctggctgatg atccgggcac cgcaccgctg gatacctta     180 tgacgctgag cgaagctctg acgggcaaaa aaggtctgtc tcgtgttctg ggccagcgtt     240
ttctgcaagc gctgcaaaaa ggttcattca aaaccgcgga ttcgctgccg cagctggcgg     300
gcgccctggc aagcggttct ctgaacccgg accaagaagc tctggcgctg aaaatcctgg     360
aagcatggta tctgggcatt gttgataatg tggttatcac ctacgaagaa gccctgatgt     420
ttagtgtcgt gtccgacacg ctggtcattc cgagctattg cccgaacaaa ccgggttct     480 gggccgaaaa accgatcgaa cgtcaggcat aatggcggat acggataccc agaaagcgga     540
cgtggtcgtg gttggatccg gcgtggcagg cgcaatcgtg gctcatcaac tggcaatggc     600
aggtaaaagc gtgatcctgc tggaagctgg tccgcgtatg ccgcgttggg aaattgttga     660
acgtttccgc aatcaagtcg ataaaaccga ctttatggca ccgtatccga gcagcgcatg     720
ggcaccgcat ccggaatatg gtccgccgaa tgattacctg atcctgaaag cgaacacaa     780 atttaactca cagtacattc gtgcagtggg cggcaccacg tggcattggg cagcctcggc     840
atggcgcttc atcccgaacg attttaaaat gaaaaccgtg tatggcgttg gtcgtgactg     900
gccgattcag tacgatgaca tcgaacatta ttaccaacgc gcggaagaag aactgggcgt     960
gtggggtccg ggcccggaag aagacctgta ttcaccgcgt aaagaaccgt acccgatgcc    1020
gccgctgccg ctgagtttca tgaacaaac cattaaatcc gctctgaacg ctatgatcc     1080 gaaatttcac gtggttacgg aaccggtggc ccgtaattcg cgcccgtacg acggtcgccc    1140
gacctgctgt ggcaacaata actgcatgcc gatttgtccg atcggtgcaa tgtataacgg    1200
catcgtccat gtggaaaaag ctgaacaggc aggtgctaaa ctgattgata gtgcggtcgt    1260
gtacaaactg gaaacgggcc cggacaaacg tattaccgca gctgtttata agataaaac     1320 gggtgcggac catcgcgtcg aaggcaaata cttcgtgatt gcggccaatg gtatcgaaac    1380
cccgaaaatt ctgctgatga gcgcgaaccg tgattttccg aatggtgtgg ccaacagttc    1440
```

```
cgatatggtt ggccgcaatc tgatggacca tccgggcacc ggcgtgagct tttatgcaaa    1500
cgaaaaactg tggccgggtc gtggtccgca ggaaatgacc tctctgatcg gtttccgtga    1560
tggcccgttt cgcgcgaatg aagcagcgaa gaaaattcat ctgtcaaata tgtcgcgtat    1620
caaccaggaa acccaaaaaa tctttaaagg cggtaaactg atgaaaccgg aagaactgga    1680
tgcgcagatc cgtgaccgca gtgcccgctt tgttcaattc gattgctttc acgaaatcct    1740
gccgcagccg gaaatcgta ttgtcccgtc caaaaccgca acggacgcag tgggtattcc    1800
gcgtccggaa attacgtatg cgatcgatga ctacgtcaaa cgtggcgcag tgcatacgcg    1860
cgaagtttat gctaccgcgg ccaaagtgct gggcggcacc gaagtggtct tcaacgatga    1920
atttgcgccg aataaccaca tcaccggtgc cacgattatg ggcgcggatg cccgtgactc    1980
agtggttgat aaagactgtc gcgccttcga tcatccgaac ctgttttatta gcagcagcag    2040 caccatgccg acggttggca ccgttaacgt caccctgacg attgcagctc tggcactgcg    2100
tatgtctgat acgctgaaaa aagaagtcga attcggttct ggttatggct ctggtccgcc    2160
gggtccgatt cgtgcaggtg ctaccatgcc gcatcgtgat cgtggtccgt gcggtgcatg    2220
tcacgctatt atccagggca gtggttccgg ccatcaccat caccatcact aaaagctt     2278
```

<210> SEQ ID NO 27
<211> LENGTH: 7
<212> TYPE: PRT
<213> ORGANISM: Artificial Sequence
<220> FEATURE:
<223> OTHER INFORMATION: Synthetic

<400> SEQUENCE: 27

Gly Ser Gly Tyr Gly Ser Gly
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

His His His His His His
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic

<400> SEQUENCE: 29

Gly Ser Gly Ser Gly
1               5